United States Patent
Wilson

(10) Patent No.: US 12,264,332 B2
(45) Date of Patent: *Apr. 1, 2025

(54) HIGHLY EFFICIENT GAS PERMEABLE DEVICES AND METHODS FOR CULTURING CELLS

(71) Applicant: Wilson Wolf Manufacturing, LLC, St. Paul, MN (US)

(72) Inventor: John R. Wilson, New Brighton, MN (US)

(73) Assignee: Wilson Wolf Manufacturing, LLC, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/516,773

(22) Filed: Nov. 2, 2021

(65) Prior Publication Data

US 2022/0049215 A1 Feb. 17, 2022

Related U.S. Application Data

(63) Continuation of application No. 15/643,621, filed on Jul. 7, 2017, now Pat. No. 11,377,635, which is a
(Continued)

(51) Int. Cl.
*C12M 1/00* (2006.01)
*C12M 1/04* (2006.01)
(Continued)

(52) U.S. Cl.
CPC ........... *C12N 5/0602* (2013.01); *C12M 23/08* (2013.01); *C12M 23/24* (2013.01); *C12M 23/34* (2013.01)

(58) Field of Classification Search
CPC ....... C12M 23/34; C12M 23/08; C12M 23/24
See application file for complete search history.

(56) References Cited

U.S. PATENT DOCUMENTS 3,459,176 A   8/1969   Leonard
3,839,155 A   10/1974  McAleer et al.
(Continued)

FOREIGN PATENT DOCUMENTS

CA   2105419       3/1994
CN   1441841 A    9/2003
(Continued)

OTHER PUBLICATIONS

US 6,465,252 B1, 10/2002, Toner et al. (withdrawn)
(Continued)

*Primary Examiner* — Nathan A Bowers
(74) *Attorney, Agent, or Firm* — Husch Blackwell LLC

(57) ABSTRACT

This invention relates to methods and devices that improve cell culture efficiency. They include the use of gas permeable culture compartments that reduce the use of space while maintaining uniform culture conditions, and are more suitable for automated liquid handling. They include the integration of gas permeable materials into the traditional multiple shelf format to resolve the problem of non-uniform culture conditions. They include culture devices that use surfaces comprised of gas permeable, plasma charged silicone and can integrate traditional attachment surfaces, such as those comprised of traditional tissue culture treated polystyrene. They include culture devices that integrate gas permeable, liquid permeable membranes. A variety of benefits accrue, including more optimal culture conditions during scale up and more efficient use of inventory space, incubator space, and disposal space. Furthermore, labor and contamination risk are reduced.

2 Claims, 26 Drawing Sheets

Related U.S. Application Data continuation of application No. 14/321,933, filed on Jul. 2, 2014, now Pat. No. 9,732,317, which is a continuation of application No. 11/952,848, filed on Dec. 7, 2007, now Pat. No. 8,809,044.

(60) Provisional application No. 60/873,347, filed on Dec. 7, 2006.

(51) Int. Cl.
    C12M 1/24    (2006.01)
    C12N 5/071   (2010.01)

(56) References Cited

U.S. PATENT DOCUMENTS

| | | |
|---|---|---|
| 3,853,712 A | 12/1974 | House et al. |
| 3,870,602 A | 3/1975 | Froman et al. |
| 3,873,423 A | 3/1975 | Munder et al. |
| 3,941,661 A | 3/1976 | Noteboom |
| 3,941,662 A | 3/1976 | Munder et al. |
| 3,948,732 A | 4/1976 | Haddad et al. |
| 4,142,940 A | 3/1979 | Modolell et al. |
| 4,228,243 A | 10/1980 | Iizuka |
| 4,296,205 A | 10/1981 | Verma |
| 4,317,886 A | 3/1982 | Johnson et al. |
| 4,435,508 A | 3/1984 | Gabridge |
| 4,640,895 A | 2/1987 | Davis |
| 4,649,114 A | 3/1987 | Miltenburger et al. |
| 4,661,455 A | 4/1987 | Hubbard |
| 4,668,632 A | 5/1987 | Young et al. |
| 4,717,668 A | 1/1988 | Keilman et al. |
| 4,734,373 A | 3/1988 | Bartal |
| 4,748,124 A | 5/1988 | Vogler |
| 4,824,787 A | 4/1989 | Serkes et al. |
| 4,829,002 A | 5/1989 | Pattillo et al. |
| 4,829,004 A | 5/1989 | Varani et al. |
| 4,839,292 A | 6/1989 | Cremonese |
| 4,847,462 A | 7/1989 | Soodak et al. |
| 4,897,359 A | 1/1990 | Oakley et al. |
| 4,906,577 A | 3/1990 | Armstrong et al. |
| 4,912,058 A | 3/1990 | Mussi et al. |
| 4,937,194 A | 6/1990 | Pattillo et al. |
| 4,937,196 A | 6/1990 | Wrasidlo et al. |
| 4,939,151 A | 7/1990 | Bacehowski et al. |
| 4,945,203 A | 7/1990 | Soodak et al. |
| 4,960,706 A | 10/1990 | Bliem et al. |
| 5,017,490 A | 5/1991 | Taiariol et al. |
| 5,026,650 A | 6/1991 | Schwarz et al. |
| 5,047,347 A | 9/1991 | Cline |
| 5,068,195 A | 11/1991 | Howell et al. |
| 5,078,755 A | 1/1992 | Tozawa et al. |
| 5,079,168 A | 1/1992 | Amiot |
| 5,139,946 A | 8/1992 | Howell et al. |
| 5,139,951 A | 8/1992 | Butz et al. |
| 5,153,131 A | 10/1992 | Wolf et al. |
| 5,173,225 A | 12/1992 | Range et al. |
| 5,225,346 A | 7/1993 | Matsumiya et al. |
| 5,240,854 A | 8/1993 | Berry et al. |
| 5,310,676 A | 5/1994 | Johansson et al. |
| 5,324,428 A | 6/1994 | Flaherty |
| 5,330,908 A | 7/1994 | Spaulding |
| 5,416,022 A | 5/1995 | Amiot |
| 5,426,037 A | 6/1995 | Pannell et al. |
| 5,437,998 A | 8/1995 | Schwarz et al. |
| 5,449,617 A | 9/1995 | Falkenberg et al. |
| 5,462,874 A | 10/1995 | Wolf et al. |
| 5,503,741 A | 4/1996 | Clark |
| 5,527,705 A | 6/1996 | Mussi et al. |
| 5,576,211 A | 11/1996 | Falkenberg et al. |
| 5,650,325 A | 7/1997 | Spielmann |
| 5,658,797 A | 8/1997 | Bader |
| 5,659,997 A | 8/1997 | Sprehe et al. |
| 5,670,332 A | 9/1997 | Kuhl et al. |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,702,945 A | 12/1997 | Nagels et al. |
| 5,707,869 A | 1/1998 | Wolf et al. |
| 5,714,384 A | 2/1998 | Wilson |
| 5,736,398 A | 4/1998 | Giambernardi et al. |
| 5,759,847 A | 6/1998 | Eden et al. |
| 5,763,267 A | 6/1998 | Kurjan et al. |
| 5,763,275 A | 6/1998 | Nagels et al. |
| 5,783,075 A | 7/1998 | Eddleman et al. |
| 5,786,215 A | 7/1998 | Brown et al. |
| 5,866,400 A | 2/1999 | Palsson et al. |
| 5,866,419 A | 2/1999 | Meder |
| 5,876,604 A | 3/1999 | Nemser et al. |
| 5,902,747 A | 5/1999 | Nemser et al. |
| 5,914,154 A | 6/1999 | Nemser |
| 5,928,936 A | 7/1999 | Ingram |
| 5,935,847 A | 8/1999 | Smith et al. |
| 5,985,653 A | 11/1999 | Armstrong et al. |
| 5,989,913 A | 11/1999 | Anderson et al. |
| 6,063,618 A | 5/2000 | Weuster-Botz et al. |
| 6,130,080 A | 10/2000 | Fuller |
| 6,150,159 A | 11/2000 | Fry |
| 6,190,913 B1 | 2/2001 | Singh |
| 6,228,607 B1 | 5/2001 | Kersten et al. |
| 6,297,046 B1 | 10/2001 | Smith et al. |
| 6,306,491 B1 | 10/2001 | Kram et al. |
| 6,455,310 B1 | 9/2002 | Barbera-Guillem |
| 6,468,792 B1 | 10/2002 | Bader |
| 6,479,252 B1 | 11/2002 | Barbera-Guillem et al. |
| 6,562,616 B1 | 5/2003 | Toner et al. |
| 6,569,675 B2 | 5/2003 | Wall et al. |
| 6,605,463 B1 | 8/2003 | Bader |
| 6,759,245 B1 | 7/2004 | Toner et al. |
| 6,821,772 B2 | 11/2004 | Barbera-Guillem et al. |
| 6,855,542 B2 | 2/2005 | DiMilla et al. |
| 6,900,055 B1 | 5/2005 | Fuller et al. |
| 7,229,820 B2 | 6/2007 | Wilson |
| 7,560,274 B1 | 7/2009 | Fuller et al. |
| 7,745,209 B2 | 6/2010 | Martin et al. |
| 8,158,426 B2 | 4/2012 | Wilson |
| 8,158,427 B2 | 4/2012 | Wilson |
| 8,168,432 B2 | 5/2012 | Wilson |
| 8,518,692 B2 | 8/2013 | Wilson |
| 8,697,443 B2 | 4/2014 | Wilson et al. |
| 8,809,044 B2 | 8/2014 | Wilson |
| 9,441,192 B2 | 9/2016 | Wilson et al. |
| 9,732,317 B2 | 8/2017 | Wilson |
| 11,377,635 B2 | 7/2022 | Wilson |
| 2002/0110905 A1 | 8/2002 | Barbera-Guillem et al. |
| 2002/0119121 A1 | 8/2002 | Vitiello et al. |
| 2002/0197710 A1 | 12/2002 | Yoo et al. |
| 2003/0008388 A1 | 1/2003 | Barbera-Guillem et al. |
| 2003/0017142 A1 | 1/2003 | Toner et al. |
| 2003/0077816 A1 | 4/2003 | Kronenthal et al. |
| 2003/0157709 A1 | 8/2003 | DiMilla et al. |
| 2004/0029266 A1 | 2/2004 | Barbera-Guillem |
| 2004/0043481 A1 | 3/2004 | Wilson |
| 2004/0067585 A1 | 4/2004 | Wang et al. |
| 2004/0072347 A1 | 4/2004 | Schuler |
| 2004/0110199 A1 | 6/2004 | Montemagno et al. |
| 2004/0259239 A1 | 12/2004 | Branson et al. |
| 2005/0032205 A1 | 2/2005 | Smith et al. |
| 2005/0089993 A1 | 4/2005 | Boccazzi et al. |
| 2005/0106717 A1 | 5/2005 | Wilson |
| 2007/0026516 A1 | 2/2007 | Martin et al. |
| 2008/0206857 A1 | 8/2008 | Kenney et al. |
| 2008/0227176 A1 | 9/2008 | Wilson |
| 2010/0255576 A1 | 10/2010 | Wilson et al. |
| 2014/0315296 A1 | 10/2014 | Wilson |
| 2017/0313977 A1 | 11/2017 | Wilson |
| 2018/0355300 A1 | 12/2018 | Martin |

FOREIGN PATENT DOCUMENTS

| | | |
|---|---|---|
| DE | 4229334 | 3/1994 |
| EP | 0155237 A2 | 9/1985 |
| EP | 264464 | 4/1988 |

(56) References Cited

FOREIGN PATENT DOCUMENTS

| | | |
|---|---|---|
| EP | 0280054 A1 | 8/1988 |
| EP | 0647707 | 4/1995 |
| EP | 0700990 | 3/1996 |
| EP | 0725134 A2 | 8/1996 |
| EP | 0866122 A2 | 9/1998 |
| EP | 353893 | 2/1999 |
| EP | 0890636 | 10/2001 |
| EP | 1245670 | 10/2002 |
| FR | 2666094 | 2/1992 |
| GB | 2268187 | 1/1994 |
| JP | 59220182 | 12/1984 |
| JP | 6434283 | 7/1987 |
| JP | 5123182 | 5/1993 |
| JP | 78267 | 1/1995 |
| JP | 734699 | 6/1995 |
| JP | 11028083 A | 2/1999 |
| JP | 2002528567 A | 9/2002 |
| JP | 2002335946 | 11/2002 |
| JP | 2003503022 | 1/2003 |
| JP | 2004129568 A | 4/2004 |
| WO | 9013628 A1 | 11/1990 |
| WO | 1996030497 | 10/1996 |
| WO | 1998017362 | 4/1998 |
| WO | 9831782 A1 | 7/1998 |
| WO | 1998053894 | 12/1998 |
| WO | 0056870 | 9/2000 |
| WO | 2000058437 | 10/2000 |
| WO | 2000078920 | 12/2000 |
| WO | 2000078932 | 12/2000 |
| WO | 0192462 | 12/2001 |
| WO | 0242419 A2 | 5/2002 |
| WO | 0242419 A3 | 5/2002 |
| WO | 0244341 A2 | 6/2002 |
| WO | 200264730 | 8/2002 |
| WO | 2003060061 | 7/2003 |
| WO | 2005035728 | 4/2005 |

OTHER PUBLICATIONS

Reexamination No. 90/014,538, Exhibit 2019 Office Action of Apr. 18, 2011 in U.S. Appl. No. 11/952,848 File History, filed Apr. 19, 2021, 10.
Reexamination No. 90/014,538, Exhibit 2020 Order of Oct. 6, 2020 in 0:20-cv-00700DWF-TNL, filed Apr. 19, 2021, 43.
Reexamination No. 90/014,538, Interview Summary filed Jul. 28, 2021, 10.
Reexamination No. 90/014,540, Transmittal of Exhibit 2016 Second Declaration of Dr. Maury Cosman and Exhibit 2017 Third Declaration of Dr. Maury D. Cosman, filed Jul. 13, 2021, 58.
Reexamination No. 90/014,540 Request for Extension of Time Granted mailed Jun. 7, 2021, 3.
Reexamination No. 90/014,541 Advisory Action mailed Nov. 4, 2021, 4.
Reexamination No. 90/014,541 Applicant Summary of Interview with Examiner filed Jun. 21, 2021, 5.
Reexamination No. 90/014,541 Authorization for Internet Communications filed May 7, 2021, 4.
Reexamination No. 90/014,541 Communication Regarding Power of Attorney mailed Apr. 27, 2021, 2.
Reexamination No. 90/014,541 Decision on Petition for Extension of Time in Reexamination mailed Sep. 13, 2021, 5.
Reexamination No. 90/014,541 Decision on Petition for Extension of Time in Reexamination mailed Sep. 2, 2021, 6.
Reexamination No. 90/014,541 Examiner Interview Summary mailed Jun. 3, 2021, 14.
Reexamination No. 90/014,541 Exhibit 2021 Declaration of Dr. Maury D. Cosman filed Jun. 1, 2021, 37.
Reexamination No. 90/014,541, filed Jun. 1, 2021 Exhibit 2022 Restriction Requirement of Jun. 8, 2006 in U.S. Appl. No. 10/961,814, filed Jun. 1, 2021, 6.
Reexamination No. 90/014,541 Final Rejection mailed Jul. 19, 2021, 35.
Reexamination No. 90/014,541 Information Disclosure Statement filed Jun. 22, 2021, 15.
Reexamination No. 90/014,541 Information Disclosure Statement filed Jun. 28, 2021, 8.
Reexamination No. 90/014,541 Information Disclosure Statement filed Sep. 1, 2021, 6.
Reexamination No. 90/014,541 Non-Final Office Action mailed Apr. 1, 2021, 34.
Reexamination No. 90/014,541 Notice of Appeal filed Dec. 17, 2021, 8.
Reexamination No. 90/014,541 Patent Owner's Response to Final Office Action filed Oct. 19, 2021, 47.
Reexamination No. 90/014,541 Patent Owner's Response to Office Action filed Jun. 1, 2021, 106.
Reexamination No. 90/014,541 Patent Owner's Supplemental Response to Final Office Action filed Oct. 27, 2021, 6.
Reexamination No. 90/014,541 Petition for Extension of Time filed Aug. 25, 2021, 8.
Reexamination No. 90/014,541 Petition for Extension of Time filed Sep. 2, 2021, 9.
Reexamination No. 90/014,541 Power of Attorney filed Apr. 22, 2021, 7.
Reexamination No. 90/014,540 EXH, "Large-Scale Ex Vivo Expansion and Characterization of Natural Killer Cells for Clinical Applications", Cytotherapy, 2012:14-1131-1143, filed Jul. 12, 2021, 14.
Reexamination No. 90/014,540 EXH, "Optimizing the production of suspension cells using the G-Rex "M" Series", Molecular Therapy-Methods & Clinical Development (2014) 1, 14015; doi: 10.1038/mtm2014.15, published Online May 14, 2014, filed Jul. 12, 2021, 10.
U.S. Appl. No. 12/753,573, filed Apr. 2, 2010, Wilson et al., Utility application.
U.S. Appl. No. 14/810,071, filed Jul. 27, 2015, Wilson et al., Utility application.
U.S. Appl. No. 60/509,651, filed Oct. 8, 2003, Wilson et al.
U.S. Appl. No. 60/873,347, filed Dec. 7, 2006, Wilson et al.
Barbera-Guillem, E., "Overcoming Cell Culture Barriers to Meet the Demands of Cell Biology and Biotechnology," Am. Biotech. Lab., May 2001 (3 pages).
CLINIcell 250® commercial product and User Instructions V-2 listed as Exhibit 4 in Corning Incorporated's Prior Art Statement in Civil No. 13-210(DWF/AJB) D. Minn. dated Sep. 5, 2013 (5 pages).
Corning CellCUBE® Systems URL:<https://ecatalog.corning.com/life-sciences/b2c/US/en/Bioprocess-and-Scale-up/CellCube%C2%AE/CellCube-System/Corning%C2%AE-CellCube%C2%AE-Systems/p/corningCellCubeSystems> Accessed on the Internet Mar. 1, 2021 (9 pages).
Corning CellSTACK® Culture Chambers URL :<https://ecatalog.corning.com/life-sciences/b2c/US/en/Browse-Products-by-Application/Cell-Therapy-and-Vaccines/CellSTACK%C2%AE/Corning%C2%AE-CellSTACK%C2%AE-Culture-Chambers/p/corningCellSTACKCultureChambers>. Accessed on the Internet on Mar. 1, 2021 (14 pages).
Corning E-CUBE™ Culture System Kit URL :<https://ecatalog.corning.com/life-sciences/b2c/US/en/Bioprocess-and-Scale-up/CellCube%C2%AE/E-Cube-System/E-Cube%E2%84%A2-Culture-System-Kit-%28without-CellCube%C2%AE-Module%29/p/3286> Accessed on the Internet Mar. 1, 2021 (6 pages).
Corning Hyperflask Cell Culture Vessel Instructions for Use ©2008 (4 pages).
Corning Hyperflask Cell Culture Vessels dated Jul. 1, 2013 (2 pages).
Corning Hyperstack Cell Culture Vessel Closed System Protocol Guide ©2011 (4 pages).
Corning Hyperstack Cell Culture Vessel dated Jul. 1, 2013 (1 page).
Pardo, Ana Maria P. et al. "A Comparative Study Examining Corning's Hyperstack Cell Culture Vessel Technology", submitted with Plaintiffs' Claim Charts in Civil No. 13-210(DWF/AJB) (D. Minn.) dated Jul. 1, 2013 (1 page).

(56) References Cited

OTHER PUBLICATIONS

Pardo, Ana Maria P. et al. "Corning Hyperstack Cell Culture Vessel: Performance Analysis", ©2011 (8 pages).
Pardo, Ana Maria P. et al. "Expansion of Human Mesenchymal Stem Cells Using Coming Hyper Technology Cell Culture Vessels", ©2012 (6 page).
Pardo, Pilar et al. "Bioprocess Scale-Up Using Coming Hyperstack Vessels", Bioprocess International Industry Yearbook 2011-2012 pp. 22-23.
Petaka™ Cell Culturing System URL: <https://www.neuromics.com/petaka-cell-culturing-system> Accessed on the Internet Mar. 1, 2021 (3 pages).
Ryan, John A. "Growing More Cells: A Simple Guide to Small Volume Cell Culture Scale-Up" ©2010, 2012 (16 pages).
Stang, B.V. "Monoclonal Antibody Production in Gas-Permeable Flexible Flasks, Using Serum-Free Media," Contemporary Topics, 37(6) 55-60 (1999).
Titus, Kim et al. "Closed System Cell Culture Protocol Using HYPERStack Vessels with Gas Permeable Material Technology", Journal of Visualized Experiments, Nov. 29, 2010 (5 pages).
Veliz, R.V. "Alternative Techniques to Obtain Monoclonal Antibodies at a Small Scale: Current State and Future Goals," Biotecnologia Aplicada, 19, 119-131 (2002).
U.S. Ex Parte Reexamination No. 90/014,538, Non-Final Office Action dated Feb. 19, 2021 (21 pages).
U.S. Ex Parte Reexamination No. 90/014,538, Exhibit 1037 *Mobile Tech, Inc. v. Invue Security Prods., Inc.*, IPR2018-01138, Paper 28 (PTAB Dec. 5, 2019) (56 pages).
U.S. Ex Parte Reexamination No. 90/014,538, Exhibit 1038 *Alphatec Holdings, Inc. v. Nuvasive, Inc.*, IPR2019-00361, Paper 59 (PTAB Jul. 8, 2020) (83 pages).
U.S. Ex Parte Reexamination No. 90/014,538, Exhibit 1039 *Adama Makhteshim Ltd. V. Finchimica S.P.A.*, IPR2016-00577, Paper 7 (PTAB May 24, 2016) (19 pages).
U.S. Ex Parte Reexamination No. 90/014,538, Exhibit 1033 Reply Declaration of Charles L. Crespi, Ph.D. Pursuant to 37 C.F.R. § 1.132 (27 pages).
U.S. Ex Parte Reexamination No. 90/014,538, Reply of Third-Party Requester Corning Incorporated to Patent Owner's Statement under 35 U.S.C. § 304, filed Dec. 2, 2020 (71 pages).
U.S. Ex Parte Reexamination No. 90/014,538, Exhibit 2001 Declaration of Dr. Maury D. Cosman (23 pages).
U.S. Ex Parte Reexamination No. 90/014,538, Exhibit 2002 Declaration of Dr. Emilio Barbera-Guillem (29 pages).
U.S. Ex Parte Reexamination No. 90/014,538, Exhibit 2006 Response of Jul. 6, 2020 in U.S. Appl. No. 15/671,485 (7 pages).
U.S. Ex Parte Reexamination No. 90/014,538, Exhibit 2009 Declaration of John Wilson dated Oct. 2, 2020 (36 pages).
U.S. Ex Parte Reexamination No. 90/014,538, Exhibit 2010 Wilson Spreadsheet Showing Diligence (24 pages).
U.S. Ex Parte Reexamination No. 90/014,538, Exhibit 2013 Corning Guide for Identifying and Correcting Common Cell Growth Patterns (13 pages).
U.S. Ex Parte Reexamination No. 90/014,538, Exhibit 2014 Closed System Cell Culture Protocol Using HYPERStack Vessel with Gas Permeable Material Technology (6 pages).
U.S. Ex Parte Reexamination No. 90/014,538, Exhibit 2015 Biographical Sketch of John Wilson (6 pages).
U.S. Ex Parte Reexamination No. 90/014,538 Patent Owner's Statement Under 35 U.S.C. 304, filed Oct. 2, 2020 (64 pages).
U.S. Ex Parte Reexamination No. 90/014,538 Order Granting Request for Ex Parte Reexamination mailed Aug. 4, 2020 (21 pages).
U.S. Ex Parte Reexamination No. 90/014,538 Examiner Interview Summary mailed Jul. 16, 2020 (3 pages).
U.S. Ex Parte Reexamination No. 90/014,538 Litigation Search Report dated Jul. 7, 2020 (40 pages).
U.S. Ex Parte Reexamination No. 90/014,538 Notice of Assignment of Reexamination Request mailed Jun. 30, 2020 (1 page).

U.S. Ex Parte Reexamination No. 90/014,538 Notice of Reexamination Request Filing Date mailed Jun. 30, 2020 (1 page).
U.S. Ex Parte Reexamination No. 90/014,538 Patent Assignment Abstract of Title dated Jun. 26, 2020 (1 page).
U.S. Ex Parte Reexamination No. 90/014,538 Third Party Requester Power of Attorney dated Apr. 29, 2020 (5 pages).
U.S. Ex Parte Reexamination No. 90/014,538 Request for Ex Parte Reexamation dated Jun. 26, 2020 (107 pages).
U.S. Ex Parte Reexamination No. 90/014,538 Exhibit 1001 Declaration of Charles L. Crespi, Ph.D. Pursuant ot 37 C.F.R. § 1.132 (184 pages).
U.S. Ex Parte Reexamination No. 90/014,538 Exhibit 1002 Curriculum Vitae of Charles L. Crespi (11 pages).
U.S. Ex Parte Reexamination No. 90/014,538 Exhibit 1007 Complaint filed in *Wilson Wolf Mfg. Corp. v. Brammer Bio, LLC*, Case No. 1:19-cv-02315-RGA (D. Del.) (185 pages).
U.S. Ex Parte Reexamination No. 90/014,538 Exhibit 1008 Complaint filed in *Wilson Wolf Mfg. Corp. v. Nationwide Children's Hosp. Inc et al.*, Case No. 2:20-cv-00192-MWH-CMV (S.D. Ohio) (21 pages).
U.S. Ex Parte Reexamination No. 90/014,538 Exhibit 1013 Office Action in U.S. Appl. No. 14/321,933, dated Nov. 30, 2015 (14 pages).
U.S. Ex Parte Reexamination No. 90/014,538 Exhibit 1014 Office Action in U.S. Appl. No. 14/321,933, dated Jun. 8, 2016 (19 pages).
U.S. Ex Parte Reexamination No. 90/014,538 Exhibit 1015 Amendment in U.S. Appl. No. 14/321,933, dated Dec. 8, 2016 (12 pages).
U.S. Ex Parte Reexamination No. 90/014,538 Exhibit 1024 Declaration of John R. Wilson Pursuant to 37 C.F.R. 1.131 in U.S. Appl. No. 14/321,933, dated Dec. 8, 2016 (14 pages).
U.S. Ex Parte Reexamination No. 90/014,538 Exhibit 1025 Computer-based Comparison of U.S. Patent Application Publication No. 2007/0026516 A1 to Martin et al. to U.S. Appl. No. 60/702,896 to Martin et al. (19 pages).
U.S. Ex Parte Reexamination No. 90/014,538 Exhibit 1028 Notice of Allowance in U.S. Appl. No. 14/321,933, mailed Apr. 7, 2017 (9 pages).
U.S. Ex Parte Reexamination No. 90/014,538 Exhibit 1032 Declaration of Carla M. Ford Pursuant to 37 C.F.R. § 1.132 (5 pages).
U.S. Ex Parte Reexamination No. 90/014,538 Information Disclosure Statement filed by Third Party Requester, Jun. 26, 2020 (1 page).
U.S. Ex Parte Reexamination No. 90/014,540 Reply of Third-Party Requester Corning Incorporated to Patent Owner's Statement under 35 U.S.C. § 304, filed Nov. 30, 2020 (56 pages).
U.S. Ex Parte Reexamination No. 90/014,540 Exhibit 1030 Reply Declaration of Charles L. Crespi, Ph.D. Pursuant to 37 C.F.R. § 1.132 (21 pages).
U.S. Ex Parte Reexamination No. 90/014,540 Exhibit 1034 Bognar et al., "Large Scale Propagation of BHK21 Cells Using the Opticell Culture System," J. Tissue Culture Methods 8(4): 147-154 (1983) (9 pages).
U.S. Ex Parte Reexamination No. 90/014,540 Patent Owner's Statement Under 35 U.S.C. 304 filed Sep. 30, 2020 (48 pages).
U.S. Ex Parte Reexamination No. 90/014,540 Examiner Interview Summary mailed Aug. 21, 2020 (2 pages).
U.S. Ex Parte Reexamination No. 90/014,540 Order Granting Request for Ex Parte Reexamination mailed Jul. 31, 2020 (23 pages).
U.S. Ex Parte Reexamination No. 90/014,540 Litigation Search Report dated Jul. 9, 2020 (8 pages).
U.S. Ex Parte Reexamination No. 90/014,540 Notice of Reexamination Request Filing Date mailed Jul. 6, 2020 (1 page).
U.S. Ex Parte Reexamination No. 90/014,540 Notice of Assignment of Reexamination Request mailed Jul. 6, 2020 (1 page).
U.S. Ex Parte Reexamination No. 90/014,540 Patent Assignment Abstract of Title dated Jul. 6, 2020 (1 page).
U.S. Ex Parte Reexamination No. 90/014,540 Third Party Requester Power of Attorney dated Apr. 29, 2020 (5 pages).
U.S. Ex Parte Reexamination No. 90/014,540 Exhibit 1008 First Amended Complaint filed in *Wilson Wolf Mfg. Corp. v. Sarpeta Therapeutics, Inc.*, Case No. 1:19-cv-02316-RGA (D. Del.) (202 pages).

(56) References Cited

OTHER PUBLICATIONS

U.S. Ex Parte Reexamination No. 90/014,540 Exhibit 1023 Application as filed in U.S. Appl. No. 14/810,071, filed Jul. 27, 2015 (124 pages).
U.S. Ex Parte Reexamination No. 90/014,540 Exhibit 1024 Preliminary Amendment in U.S. Appl. No. 14/810,071, filed Dec. 15, 2015 (12 pages).
U.S. Ex Parte Reexamination No. 90/014,540 Office Action in U.S. Appl. No. 14/810,071, mailed Dec. 16, 2015 (12 pages).
U.S. Ex Parte Reexamination No. 90/014,540 Exhibit 1027 Amendment in U.S. Appl. No. 14/810,071, filed Jan. 25, 2016 (13 pages).
U.S. Ex Parte Reexamination No. 90/014,540 Exhibit 1028 Notice of Allowance and Notice of Allowability in U.S. Appl. No. 14/810,071, mailed May 5, 2016 (9 pages).
U.S. Ex Parte Reexamination No. 90/014,540 Exhibit 1029 Declaration of Carla M. Ford Pursuant ot 37 C.F.R. § 1.132 (5 pages).
U.S. Ex Parte Reexamination No. 90/014,540 Request for Ex Parte Reexamination dated Jun. 26, 2020 (109 pages).
U.S. Ex Parte Reexamination No. 90/014,540 Information Disclosure Statement by Third Party Requester filed Jun. 26, 2020 (1 page).
U.S. Ex Parte Reexamination No. 90/014,540 Request for Ex Parte Reexamination Transmittal dated Jun. 26, 2020 (4 pages).
U.S. Ex Parte Reexamination No. 90/014,540 Exhibit 1002 Declaration of Charles L. Crespi, Ph.D. Pursuant to 37 C.F.R. § 1.132 (153 pages).
U.S. Ex Parte Reexamination No. 90/014,541 Reply of Third-Party Requester Corning Incorporated to Patent Owner's Statement under 35 U.S.C. § 304, filed Nov. 30, 2020 (62 pages).
U.S. Ex Parte Reexamination No. 90/014,541 Exhibit 1030 Reply Declaration of Charles L. Crepsi, Ph.D. Pursuant to 37 C.F.R. § 1.132 (21 pages).
U.S. Ex Parte Reexamination No. 90/014,541 Order Granting Request for Ex Parte Reexamination mailed Jul. 31, 2020 (13 pages).
U.S. Ex Parte Reexamination No. 90/014,541 Examiner Interview Summary mailed Jul. 30, 2020 (3 pages).
U.S. Ex Parte Reexamination No. 90/014,541 Notice of Assignment of Reexamination Request mailed Jul. 30, 2020 (1 page).
U.S. Ex Parte Reexamination No. 90/014,541 Notice of Reexamination Request Filing Date mailed Jul. 30, 2020 (1 pages).
U.S. Ex Parte Reexamination No. 90/014,541 Patent Assignment Abstract of Title dated Jun. 30, 2020 (1 page).
U.S. Ex Parte Reexamination No. 90/014,541 Litigation Search Report dated Jun. 29, 2020 (76 pages).
U.S. Ex Parte Reexamination No. 90/014,541 Third Party Requester Power of Attorney dated Apr. 29, 2020 (5 pages).
U.S. Ex Parte Reexamination No. 90/014,541 Request for Ex Parte Reexamination dated Jun. 26, 2020 (123 pages).
U.S. Ex Parte Reexamination No. 90/014,541 Information Disclosure Statement filed by Third Party Requester filed Jun. 26, 2020 (1 page).
U.S. Ex Parte Reexamination No. 90/014,541 Exhibit 1002 Declaration of Charles L. Crepsi, Ph.D. Pursuant ot 37 C.F.R. § 1.132 (173 pages).
U.S. Ex Parte Reexamination No. 90/014,541 Exhibit 1024 Office Action in U.S. Appl. No. 12/753,573, mailed Jun. 18, 2013 (12 pages).
U.S. Ex Parte Reexamination No. 90/014,541 Exhibit 1025 Amendment in U.S. Appl. No. 12/753,573, filed Sep. 20, 2013 (20 pages).
U.S. Ex Parte Reexamination No. 90/014,541 Exhibit 1026 Application as filed in U.S. Appl. No. 12/753,573, filed Apr. 2, 2010 (113 pages).
U.S. Ex Parte Reexamination No. 90/014,541 Exhibit 1027 Declaration of Carla M. Ford Pursuant to 37 C.F.R. § 1.132 (5 pages).
Decision of U.S. Court of Appeals for the Federal Circuit in Appeal 2018-1980, entered Oct. 21, 2019 (21 pages).
U.S. Interference 106,060 Exhibit 1001 Transcript of Telephone Conference before APJ Sally Gardner Lane on Dec. 14, 2016 (19 pages).
U.S. Interference 106,060 Exhibit 1003 First Declaration of Charles L. Crepsi, Ph.D. (49 pages).
U.S. Interference 106,060 Exhibit 1004 Curriculum vitae of Charles L. Crespi, Ph.D. (10 pages).
U.S. Interference 106,060 Exhibit 1006 Detailed drawings (Figs. A-D) depicting the HYPERFlask™ cell culture vessel identical to the one on display and demonstrated at the SBS 12th Annual Conference & Exhibition in Seattle, Washington, Sep. 17-21, 2006 (4 pages).
U.S. Interference 106,060 Exhibit 1010 Webster's Third New International Dictionary of the English Language, Unabridged, Merriam-Webster Inc., Springfield, MA (2002), pp. 66, 552, 1133, 1146, 1173-74, 1375-76, 1655, 1683, 1771, 2092, 2572.
U.S. Interference 106,060 Exhibit 1011 Second Declaration of Charles L. Crespi, Ph.D. (172 pages).
U.S. Interference 106,060 Exhibit 1013 Freshney, R.I., Culture of Animal Cells: A Manual of Basic Technique, 4th ed. (Wiley-Blackwell 2000), pp. 24-27, 31-34, 89-104, 182.
U.S. Interference 106,060 Exhibit 1014 Notice of Allowance in U.S. Appl. No. 11/952,848, mailed Jun. 11, 2014 (8 pages).
U.S. Interference 106,060 Exhibit 1015 Interview Summary in U.S. Appl. No. 11/952,848, dated May 27, 2014 (3 pages).
U.S. Interference 106,060 Exhibit 1016 Amendment in U.S. Appl. No. 11/952,848, filed Apr. 30, 2012 (12 pages).
U.S. Interference 106,060 Exhibit 1017 First Declaration of Todd M. Upton, Ph.D. (182 pages).
U.S. Interference 106,060 Exhibit 1018 Curriculum vitae of Todd M. Upton, Ph.D. (8 pages).
U.S. Interference 106,060 Exhibit 1019 Upton et al. "A Novel Flask Design for High Density Cell Culture" poster as presented at the SBS 12th Annual Conference & Exhibition in Seattle, Washington, Sep. 17-21, 2006 (1 page).
U.S. Interference 106,060 Exhibit 1020 Certificate of Merit from the Society for Biomolecular Sciences at the SBS Conference in recognition for the best presenation in the Cell and Protein Production Poster Session entitled "A Novel Flask Design for High Density Cell Culture" (1 page).
U.S. Interference 106,060 Exhibit 1021 Society Updates, Awards, Poster Awards, J. Biomolecular Screening 11(8): 887-901, 894-895 (Dec. 1, 2006) (15 pages).
U.S. Interference 106,060 Exhibit 1022 SLAS Discovery, Table of Contents 11(8), Articles, Society Updates (Dec. 1, 2006), http://journals.sagepub.com/toc/jbxb/11/8 (last visited Janaury 24, 2017) (9 pages).
U.S. Interference 106,060 Exhibit 1023 First Declaration of Jeanne (Phillips) Anthony (15 pages).
U.S. Interference 106,060 Exhibit 1024 First Declaration of Kimberly Titus (8 pages).
U.S. Interference 106,060 Exhibit 1025 Brochure mailed to conference attendees in advance of the SBS 12th Annual Conference & Exhibition in Seattle, Washington, Sep. 17-21, 2006 (2 pages).
U.S. Interference 106,060 Exhibit 1026 Color photograph of a copy of the HYPERFlask™ cell culture vessel identical to the one on display and demonstrated at the SBS 12th Annual Conference & Exhibition in Seattle, Washington (1 page).
U.S. Interference 106,060 Exhibit 1027 Color copies of the back wall posters on display at the Corning Booth at the SBS 12th Annual Conference & Exhibition in Seattle, Washington, Sep. 17-21, 2006 (7 pages).
U.S. Interference 106,060 Exhibit 1028 2006 Prospectus for the SBS 12th Annual Conference & Exhibition in Seattle, Washington, Sep. 17-21, 2006 (16 pages).
U.S. Interference 106,060 Exhibit 1029 Copies of the stand-alone poster boards on display at the Corning Booth at the SBS 12th Annual Conference & Exhibition in Seattle, Washington, Sep. 17-21, 2006 (2 pages).
U.S. Interference 106,060 Exhibit 1030 Conception document for priority statement (10 pages).
U.S. Interference 106,060 Exhibit 1031 Excel worksheet "Sheet1" in Excel spreadsheet entitled "Central Region HYPERFlask Leads" and accompanying screen shot of the Microsoft Excel File Information (2 pages).

(56) References Cited

OTHER PUBLICATIONS

U.S. Interference 106,060 Exhibit 1032 Excel worksheet "Sheet1" in Excel spreadsheet entitled "East Region HYPERFlask Leads" and accompanying screen shot of the Microsoft Excel File Information (3 pages).
U.S. Interference 106,060 Exhibit 1033 Excel worksheet "Sheet1" in Excel spreadsheet entitled "NE Region HYPERFlask Leads" and accompanying screen shot of the Microsoft Excel File Information (2 pages).
U.S. Interference 106,060 Exhibit 1034 Excel worksheet "Sheet1" in Excel spreadsheet entitled "SE Region HYPERFlask Leads" and accompanying screen shot of the Microsoft Excel File Information (2 pages).
U.S. Interference 106,060 Exhibit 1035 Excel worksheet "Sheet1" in Excel spreadsheet entitled "West Region HYPERFlask Leads" and accompanying screen shot of the Microsoft Excel File Information (3 pages).
U.S. Interference 106,060 Exhibit 1036 Excel worksheet "Sheet1" in Excel spreadsheet entitled "Canada Region HYPERFlask Leads" and accompanying screen shot of the Microsoft Excel File Information (2 pages).
U.S. Interference 106,060 Exhibit 1037 First Declaration of Carla M. Ford (7 pages).
U.S. Interference 106,060 Exhibit 1038 Figure 1 excerpted from Upton et al. "A Novel Flask Design for High Density Cell Culture", poster as presented at the SBS 12th Annual Conference & Exhibition in Seattle, Washington, Sep. 17-21, 2006 (1 page).
U.S. Interference 106,060 Exhibit 1039 Applicant Initiated Interview Request Form in U.S. Appl. No. 11/952,848, dated Apr. 16, 2012 (8 pages).
U.S. Interference 106,060 Exhibit 1040 Excel worksheet entitled "Alphabetically" in Excel spreadsheet entitled "SBS 2006 Leads" and accompanying screen shot of the Microsof Excel File Information (9 pages).
U.S. Interference 106,060 Exhibit 1041 Excel worksheet entitled "Sheet 1" in Excel spreadsheet entitled "SBS Poster Leads" and accompanying screen shot of the Microsof Excel File Information (3 pages).
U.S. Interference 106,060 Exhibit 1042 Redline comparison of the Declaration of John R. Wilson (WX 2004) to the Declaration of Matthew S. Croughan, Ph.D. (WX 2002) (59 pages).
U.S. Interference 106,060 Exhibit 1043 Enlarged Figure 6 (from MX 1002) (2 pages).
U.S. Interference 106,060 Exhibit 1048 Response to Notice and Statement of Opposition in European Patent No. 2336293 dated Apr. 24, 2017 (26 pages).
U.S. Interference 106,060 Exhibit 1049 Statement of Opposition dated Nov. 10, 2026 in European Patent No. 2336293 (41 pages).
U.S. Interference 106,060 Exhibit 1050 Filing Receipt in U.S. Appl. No. 14/321,933 dated Jul. 17, 2014 (3 pages).
U.S. Interference 106,060 Exhibit 1051 Amendment and Response to Non-Final Office Action in U.S. Appl. No. 14/321,933 mailed May 26, 2016 (9 pages).
U.S. Interference 106,060 Exhibit 1052 Second Declaration of Kimberly Titus (4 pages).
U.S. Interference 106,060 Exhibit 1053 Second Declaration of Carla M. Ford (5 pages).
U.S. Interference 106,060 Exhibit 1054 Transcript of the Deposition of Matthew S. Croughan, Ph.D. taked May 23, 2017 (103 pages).
U.S. Interference 106,060 Exhibit 1055 Transcript of the Deposition of John R. Wilson taken May 31, 2017 (92 pages).
U.S. Interference 106,060 Exhibit 1056 Transcript of the Deposition of Timothy Holland taken Jun. 1, 2017 (64 pages).
U.S. Interference 106,060 Exhibit 1057 Martin Objections to Wilson Exhibits dated May 12, 2017 (7 pages).
U.S. Interference 106,060 Exhibit 1058 *Pharmacia AB* v. *Ventrex Labs., Inc.*, Appeal Nos. 86-1551, 76-1622, 1987 WL 36131 (Fed. Cir. Jun. 18, 1987) (3 pages).
U.S. Interference 106,060 Exhibit 1059 *TriTek Techs., Inc.* v. *United States*, 67 Fed. Cl. 727 (Fed. Cl. 2005) (8 pages).
U.S. Interference 106,060 Exhibit 2001 SBIR Grant Application, submitted by Wilson Wolf Manufacturing Corporation, received Feb. 19, 2004 (partially redacted) (41 pages).
U.S. Interference 106,060 Exhibit 2002 Declaration of Matthew S. Croughan, Ph.D. (43 pages).
U.S. Interference 106,060 Exhibit 2003 Curriculum Vitae of Matthew S. Croughan, Ph.D. (7 pages).
U.S. Interference 106,060 Exhibit 2004 Declaration of John R. Wilson (58 pages).
U.S. Interference 106,060 Exhibit 2005 Biographical Sketch of John R. Wilson (4 pages).
U.S. Interference 106,060 Exhibit 2006 Jianjian Jin et al., Simplified Method of the Growth of Human Tumor Infiltrating Lymphocytes in Gas-Permeable Flasks to Nos. Needed for Patient Treatment, 35 J. Immunotherapy 283 (2012) (10 pages).
U.S. Interference 106,060 Exhibit 2007 Declaration of Tim S. Holland (28 pages).
U.S. Interference 106,060 Exhibit 2008 Transcript of Cross Examination of Jeanne Anthony on Apr. 11, 2017 (88 pages).
U.S. Interference 106,060 Exhibit 2009 Transcript of Cross Examination of Kimberly Titus on Apr. 11, 2017 (50 pages).
U.S. Interference 106,060 Exhibit 2010 Transcript of Cross Examination of Todd M. Upton, Ph.D. on Apr. 12, 2017 (96 pages).
U.S. Interference 106,060 Exhibit 2011 Transcript of Cross Examination of Charles L. Crespi, Ph.D. on Apr. 13, 2017 (100 pages).
U.S. Interference 106,060 Exhibit 2012 Fig. B of Exhibit 1006, colored by Todd M. Upton, Ph.D. (1 page).
U.S. Interference 106,060 Exhibit 2013 Fig B of Exhibit 1006, colored by Kimberly Titus (1 page).
U.S. Interference 106,060 Exhibit 2014 Annotated Fig. B of Exhibit 1006 (1 page).
U.S. Interference 106,060 Exhibit 2015 Annotated Fig. C of Exhibit 1006 (1 page).
U.S. Interference 106,060 Exhibit 2016 Non-Final Office Action in U.S. Appl. No. 11/433,859, mailed Jun. 15, 2009 (10 pages).
U.S. Interference 106,060 Exhibit 2017 Amendment and Response in U.S. Appl. No. 11/433,859 dated Oct. 14, 2009 (14 pages).
U.S. Interference 106,060 Exhibit 2018 Final Office Action in U.S. Appl. No. 11/433,859 mailed Jan. 15, 2010 (6 pages).
U.S. Interference 106,060 Exhibit 2019 Amendment and Response in U.S. Appl. No. 11/433,859 dated Mar. 15, 2010 (18 pages).
U.S. Interference 106,060 Exhibit 2020 U.S. Appl. No. 11/433,859 as filed on May 11, 2008 (33 pages).
U.S. Interference 106,060 Exhibit 2021 Declaration of Nathan J. Witzany (4 pages).
U.S. Interference 106,060 Exhibit 2022 *Penda Corp.* v. *U.S.*, 29 Fed. Cl. 533 (Fed. Cl. 1993) (54 pages).
U.S. Interference 106,060 Exhibit 2023 *Herman* v. *Barnes*, 2003 WL 1867350 (Bd. Pat. App. & Int.) (16 pages).
U.S. Interference 106,060 Exhibit 2024 *Industrial Tech. Res. Inst. & Ti-Shiue Biotech., Inc.* v. *Pac Biosciences of Cal., Inc.*, 2016 WL 4159336 (Pat. Tr. & App. Bd. Aug. 3, 2016) (13 pages).
U.S. Interference 106,060 Exhibit 2025 Ex Parte Brocade Commc'ns Sys., Inc., 2013 WL 6700331 (Pat. Tr. & App. Bd. Dec. 19, 2013) (21 pages).
U.S. Interference 106,060 Exhibit 2026 Ex Parte Williams, 2002 WL 851848 (Bd. Pat. App. & Int.) (5 pages).
U.S. Interference 106,060 Exhibit 2027 *Intellectual Concepts, LLC* v. *Zannier, Inc.*, 2008 WL 8967846 (Bd. Pat. App. & Int. Sep. 19, 2008) (9 pages).
U.S. Interference 106,060 Exhibit 2028 *Intelligent Digital Syst., LLC* v. *Beazley Ins. Co., Inc.*, 906 F. Supp.2d 80 (E.D.N.Y. 2012) (14 pages).
U.S. Interference 106,060 Exhibit 2029 Declaration of Sri K. Sankaran (3 pages).
U.S. Interference 106,060 Exhibit 2030 Correspondence with counsel for Senior Party Martin (2 pages).
U.S. Interference 106,060 Exhibit 2031 Wilson Objections to Admissibility of Evidence (for exhibits submitted with Martin Motions 1, 2, and 3), served to Senior Party Martin on Feb. 23, 2017 (9 pages).
U.S. Interference 106,060 Exhibit 2032 Wilson Objections to Admissibility of Evidence (for exhibits submitted with Martin Motions 1, 2, and 3), served to Senior Party Martin on Jun. 21, 2017 (4 pages).

(56) References Cited

OTHER PUBLICATIONS

U.S. Interference 106,060 Exhibit 2033 *Carroll* v. *LeBoeuf, Lamb, Greene & MacRae, L.L.P.*, 614, F.Supp.2d 481 (S.D.N.Y. 2009) (5 pages).
U.S. Interference 106,060 Exhibit 2034 *Davis* v. *Carroll*, 937 F.Supp.2d 390 (S.D.N.Y. 2013) (38 pages).
U.S. Interference 106,060 Exhibit 2035 *Mallettier* v. *Dooney & Bourke, Inc.* 525 F.Supp.2d 558 (S.D.N.Y. 2007) (106 pages).
U.S. Interference 106,060 Exhibit 2036 *Am. Med. Sys., Inc.* v. *Laser Peripherals, LLC*, 712 F.Supp.2d 885 (D. Minn. 2010) (34 pages).
U.S. Interference 106,060 Exhibit 2037 *Boswell* v. *Jasperson*, 266 F.Supp.2d 1314 (D. Utah 2003) (8 pages).
U.S. Interference 106,060 Exhibit 2038 Complaint of Nautilus Motor Tanker Co., Ltd., 862 F. Suppp. 1251 (D.N.J. 1994) (8 pages).
U.S. Interference 106,060 Exhibit 2039 *Facebook, Inc.* v. *Rembrant Social Media, L.P.*, IPR2014-00415, 2014 WL 3368963 (PTAB 2014) (12 pages).
U.S. Interference 106,060 Exhibit 2040 *Semiconductor Energy Lab. Co.* v. *Chi Mei Optoelectronics Corp.*, 485 F. Supp. 2d 1089 (N.D. Cal. 2007) (23 pages).
U.S. Interference 106,060 Exhibit 2041 *Coll. Park Holdings, LLC* v. *Racetrac Petroleum, Inc.*, 239 F. Supp. 2d 1334 (N.D. Ga. 2002) (12 pages).
U.S. Interference 106,060 Exhibit 2042 *Orthoarm, Inc.* v. *Forestadent USA, Inc.*, 682 F. Supp. 2d 978 (E.D. Mo. 2008) (12 pages).
U.S. Interference 106,060 Exhibit 2043 *ActiveVideo Networks, Inc.* v. *Verizon Commc'ns Inc.*, 801 F. Supp. 2d 465 (E.D. Va. 2011) (23 pages).
U.S. Interference 106,060 Document No. 1 Notice to Declare an Interference dated Oct. 31, 2016 (7 pages).
U.S. Interference 106,060 Document No. 2 Standing Order Entered Mar. 8, 2011 (81 pages).
U.S. Interference 106,060 Document No. 3 Wilson Notice of Real Party-in-Interest dated Nov. 14, 2016 (3 pages).
U.S. Interference 106,060 Document No. 4 Wilson Notice of Related Proceedings dated Nov. 14, 2016 (3 pages).
U.S. Interference 106,060 Document No. 5 Wilson Notice of Lead and Backup Lead Counsel dated Nov. 14, 2016 (4 pages).
U.S. Interference 106,060 Document No. 6 Wilson Clean Copy of Claims dated Nov. 14, 2016 (15 pages).
U.S. Interference 106,060 Document No. 7 Martin Notice of Real Party-in-Interest dated Nov. 14, 2016 (3 pages).
U.S. Interference 106,060 Document No. 8 Martin Notice of Related Proceedings dated Nov. 14, 2016 (3 pages).
U.S. Interference 106,060 Document No. 9 Martin Notice of Lead and Backup Counsel dated Nov. 14, 2016 (3 pages).
U.S. Interference 106,060 Document No. 10 Martin Clean Copy of Claims dated Nov. 14, 2016 (11 pages).
U.S. Interference 106,060 Document No. 11 Martin Request for File Copies dated Nov. 14, 2016 (7 pages).
U.S. Interference 106,060 Document No. 12 Order Authorizing Copies of Office Records dated Nov. 21, 2016 (3 pages).
U.S. Interference 106,060 Document No. 13 Wilson Annotated Copy of Claims dated Nov. 28, 2016 (19 pages).
U.S. Interference 106,060 Document No. 14 Martin Annotated Copy of Claims dated Nov. 28, 2016 (13 pages).
U.S. Interference 106,060 Document No. 15 Wilson List of Proposed Motions dated Dec. 8, 2016 (4 pages).
U.S. Interference 106,060 Document No. 16 Martin Submission of Motions List dated Dec. 8, 2016 (5 pages).
U.S. Interference 106,060 Document No. 17 Order re: Motion Times dated Dec. 16, 2016 (10 pages).
U.S. Interference 106,060 Document No. 18 Martin Notice of Filing Transcript dated Dec. 23, 2016 (3 pages).
U.S. Interference 106,060 Document No. 20 Joint Stipulation Extending Time Period 1 dated Jan. 26, 2017 (4 pages).
U.S. Interference 106,060 Document No. 21 Martin Statement Regarding Settlement Discussions dated Jan. 31, 2017 (3 pages).
U.S. Interference 106,060 Document No. 22 Joint Stipulation Extending Time Periods 1, 3, and 4 dated Feb. 6, 2017 (4 pages).

U.S. Interference 106,060 Document No. 23 Order dated Feb. 13, 2017 (5 pages).
U.S. Interference 106,060 Document No. 24 Wilson Priority Statement dated Feb. 15, 2017 (4 pages).
U.S. Interference 106,060 Document No. 26 Wilson Notice of Filing of Priority Statement dated Feb. 15, 2017 (3 pages).
U.S. Interference 106,060 Document No. 27 Martin Priority Statement dated Feb. 15, 2017 (4 pages).
U.S. Interference 106,060 Document No. 29 Martin Notice of Filing of Martin Priority Statement dated Feb. 15, 2017 (3 pages).
U.S. Interference 106,060 Document No. 69 Martin Substantive Motion 3 dated Feb. 15, 2017 (99 pages).
U.S. Interference 106,060 Document No. 70 Martin Substantive Motion 1 dated Feb. 15, 2017 (31 pages).
U.S. Interference 106,060 Document No. 73 Wilson Notice of Sering Priority Statement dated Feb. 16, 2017 (3 pages).
U.S. Interference 106,060 Document No. 74 Martin Notice of Service of Martin Priority Statement dated Feb. 16, 2017 (3 pages).
U.S. Interference 106,060 Document No. 75 Martin Substantive Motion 2 dated Feb. 15, 2017 (136 pages).
U.S. Interference 106,060 Document No. 76 Martin Notice of Filing Martin Second Corrected Motion 2 dated Feb. 16, 2017 (3 pages).
U.S. Interference 106,060 Document No. 77 Martin Exhibit List 1 dated Feb. 16, 2017 (6 pages).
U.S. Interference 106,060 Document No. 78 Order dated Feb. 16, 2017 (6 pages).
U.S. Interference 106,060 Document No. 79 Order dated Mar. 8, 2017 (4 pages).
U.S. Interference 106,060 Document No. 80 Joint Stipulation Extending Time Periods 3-6 dated Apr. 18, 2017 (4 pages).
U.S. Interference 106,060 Document No. 81 Wilson Opposition 1 dated May 5, 2017 (33 pages).
U.S. Interference 106,060 Document No. 82 Wilson Opposition 2 dated May 5, 2017 (41 pages).
U.S. Interference 106,060 Document No. 108 Wilson Current Exhibit List dated May 5, 2017 (4 pages).
U.S. Interference 106,060 Document No. 109 Wilson Opposition 3 dated May 5, 2017 (34 pages).
U.S. Interference 106,060 Document No. 112 Wilson Miscellaneous Motion 1 dated May 16, 2017 (8 pages).
U.S. Interference 106,060 Document No. 113 Wilson Amended Notice of Lead and Backup Counsel dated May 16, 2017 (4 pages).
U.S. Interference 106,060 Document No. 114 Wilson Current Exhibit List dated May 16, 2017 (4 pages).
U.S. Interference 106,060 Document No. 117 Order dated May 26, 2017 (4 pages).
U.S. Interference 106,060 Document No. 118 Joint Stipulation Extending Time Period 4 dated Jun. 8, 2017 (4 pages).
U.S. Interference 106,060 Document No. 119 Decision on Motion dated Jun. 12, 2017 (12 pages).
U.S. Interference 106,060 Document No. 120 Martin Reply 1 dated Jun. 14, 2017 (18 pages).
U.S. Interference 106,060 Document No. 121 Martin Reply 2 dated Jun. 14, 2017 (24 pages).
U.S. Interference 106,060 Document No. 122 Martin Reply 3 dated Jun. 14, 2017 (29 pages).
U.S. Interference 106,060 Document No. 123 Martin Exhibit List 2 dated Jun. 14, 2017 (7 pages).
U.S. Interference 106,060 Document No. 136 Order dated Jun. 20, 2017 (4 pages).
U.S. Interference 106,060 Document No. 137 Wilson Miscellaneous Motion 2 dated Jul. 7, 2017 (23 pages).
U.S. Interference 106,060 Document No. 138 Wilson Request for Oral Argument dated Jul. 7, 2017 (4 pages).
U.S. Interference 106,060 Document No. 139 Wilson Surreply 2 dated Jul. 7, 2017 (15 pages).
U.S. Interference 106,060 Document No. 140 Wilson Current Exhibit List dated Jul. 21, 2017 (5 pages).
U.S. Interference 106,060 Document No. 148 Martin Request for Oral Argument and Statement of Issues dated Jul. 7, 2017 (4 pages).
U.S. Interference 106,060 Document No. 149 Martin Miscellaneous Motion 4 dated Jul. 7, 2017 (15 pages).

(56) References Cited

OTHER PUBLICATIONS

U.S. Interference 106,060 Document No. 150 Martin Exhibit List 3 dated Jul. 7, 2017 (7 pages).
U.S. Interference 106,060 Document No. 152 Wilson Opposition 4 dated Jul. 14, 2017 (19 pages).
U.S. Interference 106,060 Document No. 153 Wilson Current Exhibit List dated Jul. 21, 2017 (5 pages).
U.S. Interference 106,060 Document No. 157 Martin Opposition 2 dated Jul. 14, 2017 (25 pages).
U.S. Interference 106,060 Document No. 158 Wilson Miscellaneous Reply 2 dated Jul. 21, 2017 (15 pages).
U.S. Interference 106,060 Document No. 159 Wilson Current Exhibit List dated Jul. 21, 2017 (5 pages).
U.S. Interference 106,060 Document No. 163 Martin Reply 4 dated Jul. 21, 2017 (15 pages).
U.S. Interference 106,060 Document No. 164 Martin Exhibit List 4 dated Jul. 21, 2017 (7 pages).
U.S. Interference 106,060 Document No. 167 Decision dated Dec. 26, 2017 (26 pages).
U.S. Interference 106,060 Document No. 168 Judgement dated Dec. 26, 2017 (3 pages).
U.S. Interference 106,060 Document No. 169 Wilson's Miscellaneous Motion 3 dated Jan. 25, 2018 (20 pages).
U.S. Interference 106,060 Document No. 170 Order Authorizing Opposition dated Feb. 1, 2018 (2 pages).
U.S. Interference 106,060 Document No. 171 Martin Opposition 3 dated Feb. 22, 2018 (21 pages).
U.S. Interference 106,060 Document No. 172 Decision on Rehearing dated Mar. 15, 2018 (9 pages).
U.S. Interference 106,060 Document No. 173 Wilson's Notice of Appeal dated May 11, 2018 (46 pages).
U.S. Interference 106,060 Document No. 174 Mandate dated Nov. 27, 2019 (1 page).
Civil Docket for Case #: 0:13-cv-00210-DWF-TNL dated Jun. 8, 2021 (53 pages).
Civil Docket for Case #: 0:20-cv-00700-DWF-TNL dated Jun. 8, 2021 (10 pages).
Case No. 20-cv-00700 (DWF/TNL) Corning Data filed by Corning with its Amended Complaint on Feb. 19, 2021 (4 pages).
Corning Incorporated's Prior Art Statement, Civil No. 13-210(DWF/AJB) filed Sep. 5, 2013 (253 pages).
Plaintiffs' Prior Art Statement, Civil No. 13-210(DWF/AJB) filed Sep. 5, 2013 (70 pages).
Corning Incorporated's Responsive Prior Art Statement, Civil No. 13-210(DWF/AJB) filed Oct. 8, 2013 (5 pages).
Plaintiffs' Response to Prior Art Statement, Civil No. 13-210(DWF/AJB) filed Oct. 8, 2013 (101 pages).
Application and File History for U.S. Appl. No. 10/961,814, filed Oct. 8, 2004, inventor Wilson.
Application and File History for U.S. Appl. No. 11/505,122, filed Aug. 16, 2006, inventor Wilson.
Application and File History for U.S. Appl. No. 12/753,573, filed Apr. 2, 2010, inventor Wilson.
Application and File History for U.S. Appl. No. 11/952,856, filed Dec. 7, 2007, inventor Wilson.
Application and File History for U.S. Appl. No. 12/499,633, filed Jul. 8, 2009, inventor Wilson.
Application and File History for U.S. Appl. No. 13/029,762, filed Feb. 17, 2011 inventors Wilson et al.
Application and File History for U.S. Appl. No. 13/194,298, filed Jul. 29, 2011, inventor Wilson.
Application and File History for U.S. Appl. No. 13/194,363, filed Jul. 29, 2011, inventor Wilson.
European Search Report for European Application No. 11/158,157 dated Dec. 15, 2011.
File Wrapper for EP Publication No. 1687400 published Aug. 9, 2006. 225 pages.
Publication re: VueLife(TM) Culture bags distributed by CellGeniz, known to applicant at least as early as Sep. 18, 2004. 4 pages.

Genetic Engineering News "OptiCell Concept for Cell Culture Operations". vol. 20, No. 21. Dec. 2000. 4 pages.
Budhiono et al., "Kinetic Aspects of Bacterial Cellulose Formation in natade-coco Culture System", Carbohydrate Polymers. vol 40. pp. 137-143 (1999).
Pulvertaft et al., "Activiation of Lymphocytes" J. Clin. Path . Vol. 20 pp. 795-805 (1967).
Machine Translation of JP-05123182 (May 13, 93).
Papas et al., "High Density Culture of Human Islets on top of Silicone Rubber Membranes," Transplantation Proceedings, vol. 37 (2005), pp. 3412-3414.
Written Opinion of the International Searching Authority for International Application No. PCT/US07/25110 dated May 20, 2008.
Giarratana et al., Cell culture bags allow a large extent of ex vivo expansion of LTC-IC and functional mature cells which can subsequently be frozen: interest for large-scale clinical applications. Bone Marrow Transplantation, Oct. 1998, vol. 22, No. 7, pp. 707-715.
CLINIcell®250 commercial product and related User Instructions V-2, date unknown.
LifeCell® X-FoldTM Culture Bag commercial product and related literature, ©2000.
Opticell® commercial product and related literature, ©2000.
OriGen PermaLife(TM) commercial product and related literature, at least as of Sep. 17, 2004.
VectraCell(TM) commercial product and related literature, at least as of Sep. 18, 2004.
VueLife(TM) Culture Bag commercial product and related literature, at least as of Oct. 28, 2003.
PetriPERM commercial product and related literature, ©2003.
English Translation of Japanese Office Action (Notice of Reasons for Rejection) for Japanese Application No. 2006-534398 dated Nov. 9, 2010.
Written Opinion from International Application No. PCT/US2009/049944 dated Jan. 20, 2011.
Nagel et al., Membrane-based cell culture systems—an alternative to in vivo production of monoclonal antibodies. Dev Biol Stand, 1999, vol. 101, pp. 57-64.
Secker et al., Gas-permeable lifecell tissue culture flasks give improved growth of Helicobacter pylori in a liquid medium., J Clin Microbial, May 1991, vol. 29, No. 5, pp. 1060-1061.
Canadian Office Action for Canadian Application No. 2,671,812 dated Feb. 28, 2011.
Canadian Office Action for Canadian Application No. 2,671,967 dated Mar. 1, 2011.
Jensen Mona D., et al., "Diffusion in Tissue Cultures on Gas-permeable and Impermeable Supports", J. Theor,. Biol. 56, 443-458 (1976).
Jensen, Mona D., "Mass cell culture in a controlled environment", Cell Culture and its Applications, Academic Press (1977).
Jensen, Mona D., "Production of Anchorage-Dependent Cells-Problems and their Possible Solutions," Biotechnology and Bioengineering, vol. XXIII, pp. 2703-2716 (1981).
Vogler, E. A., "A Compartmentalized Device for the Culture of Animal Cells", Biomat., Art. Cells, Art. Org., 17(5), 597-610 (1989).
Techno Plastics, Web Catalog (Jan. 2003) http://web.achive.org/web/20031209110901/http://www.tpp.ch/tis.
BabbleFish translation of FR2666094 (Feb. 28, 1992).
Mathiot et al., "Increase of hybridoma productivity using an original dialysis culture system,", Cytotechnology, vol. 11 (1993), pp. 41-48.
Case No. 20-cv-00700 (DWF/TNL), Exhibit 1 Table of Contents for Corning's Prior Art Statement to Defendants' Responsive Prior Art Statement (4 pages).
Case No. 20-cv-00700 (DWF/TNL), Defendants' Responsive Prior Art Statement filed Mar. 15, 2021 (667 pages).
Case No. 20-cv-00700 (DWF/TNL), Plaintiff Corning Incorporated's Prior Art Statement filed Feb. 1, 2021 (697 pages).
Amended Complaint & Exhibits, Docket No. 73, 73-1, 73-2 & 73-3 in *Corning* v. *Wilson Wolf Manufacturing Corp.*, 0:20-cv-00700-DWF-TNL (D. Minn.), ¶¶ 59-110, 182-86, 202-206 regarding test data and a declaration of Dr. Juan Vera and allegations relating to U.S. Pat. No. 9,441,192 and U.S. Pat. No. 8,697,443, and ¶¶ 111-71,

(56) References Cited

OTHER PUBLICATIONS 222-25 and Exhibits K and L, regarding interference proceedings and a declaration of John Wilson and allegations relating to U.S. Pat. No. 9,732,317.
Declaration of John Wilson, Docket No. 187 in *Wilson v Corning*, 0:13-cv-00210-DWF-TNL (D. Minn.), addressing Dr. Juan Vera and Dr. Vera's declaration.
Joint Claim Construction Statement & Exhibits, Docket No. 105 & 105-1 in *Corning v. Wilson Wolf Manufacturing Corp.*, 0:20-cv-00700-DWF-TNL (D. Minn.), addressing construction of claims in U.S. Pat. No. 9,441,192, U.S. Pat. No. 8,697,443 and U.S. Pat. No. 9,732,317.
Joint Claim Construction Statement & Exhibits, Docket No. 83, 83-1, 83-2 & 83-3 in *Wilson v Corning*, 0:13-cv-00210-DWF-TNL (D. Minn.), addressing construction of claims in U.S. Pat. No. 8,158,426 and U.S. Pat. No. 8,158,427.
Claim Construction Briefs, Docket Nos. 121, 124, 129, 134, 135 & 136 in *Wilson v Corning*, 0:13-cv-00210-DWF-TNL (D. Minn.), addressing construction of claims in U.S. Pat. No. 8,158,426 and U.S. Pat. No. 8,158,427.
*Corning v. Wilson Wolf Manufacturing Corp.*, 0:20-cv-00700-DWF-TNL, Opening claim construction briefs and accompanying declarations and exhibits for U.S. Pat. Nos. 9,441,192, 8,697,443, and 9,732,317, Docket Nos. 112, 113, 114, 115, and 116.
*Corning v. Wilson Wolf Manufacturing Corp.*, 0:20-cv-00700-DWF-TNL, Defendants' Responsive Claim Construction Memorandum, Docket No. 121.
*Corning v. Wilson Wolf Manufacturing Corp.*, 0:20-cv-00700-DWF-TNL, Declaration of Sri K. Sankaran, Docket No. 122.
*Corning v. Wilson Wolf Manufacturing Corp.*, 0:20-cv-00700-DWF-TNL, Corning Incorporated's Responsive Claim Construction Brief, Docket No. 125.
*Corning v. Wilson Wolf Manufacturing Corp.*, 0:20-cv-00700-DWF-TNL, Defendants' Reply Claim Construction Memo, Docket No. 135.
*Corning v. Wilson Wolf Manufacturing Corp.*, 0:20-cv-00700-DWF-TNL, Declaration of Sri K. Sankaran, Docket No. 136.
*Corning v. Wilson Wolf Manufacturing Corp.*, 0:20-cv-00700-DWF-TNL, Corning Incorporated's Reply Claim Construction Brief, Docket No. 137.
*Corning v. Wilson Wolf Manufacturing Corp.*, 0:20-cv-00700-DWF-TNL, Declaration of Ivan Poullaos in Support of Plaintiff Corning Incorporated's Reply Claim Construction Brief, Docket No. 138.
Case 0:20-cv-00700-DWF-TNL, Transcript of the oral argument on claim construction held on Dec. 16, 2021, 249.
Court File No. 13-210(DWF/TNL) Pleading Register, 55.
Court File No. 20-cv-00700(WMW/KMM) Pleading Register, 11.
Interference No. 106,060 (*Wilson v.Martin*, 11952848 v. 14814267, Declaration Date Oct. 31, 2016, Judgment Date Dec. 27, 2017).
Reexamination No.90/014,538, Exhibit 2018 Response in Restriction Requirement in U.S. Appl. No. 11/952,848 File History, filed Apr. 19, 2021, 5.
Reexamination No. 90/014,538, Exhibit 2017 Office Action of Oct. 5, 2010, in U.S. Appl. No. 11/952,848 File History, filed Apr. 19, 2021, 8.
Reexamination No. 90/014,538, Advisory Action mailed Aug. 19, 2021, 58.
Reexamination No. 90/014,538, Appeal Brief filed Dec. 1, 2021, 58.
Reexamination No. 90/014,538, Authorization for Internet Communications filed Jun. 8, 2021, 4.
Reexamination No. 90/014,538, Examiner Interview Summary mailed Jul. 1, 2021, 22.
Reexamination No. 90/014,538, Exhibit 2016 Second Declaration of Dr. Maury Cosman, filed Apr. 19, 2021, 17.
Reexamination No. 90/014,538, Final Rejection mailed Jun. 2, 2021, 19.
Reexamination No. 90/014,538, Information Disclosure Statement filed Jun. 28, 2021, 8.
Reexamination No. 90/014,538, Information Disclosure Statement filed Jun. 8, 2021, 13.
Reexamination No. 90/014,538, Information Disclosure Statement filed Sep. 1, 2021, 6.
Reexamination No. 90/014,538, Notice of Appeal filed Oct. 1, 2021, 9.
Reexamination No. 90/014,538, Patent Owners Response to Office Action filed Apr. 19, 2021, 52.
Reexamination No. 90/014,538, Response to Final Rejection filed Aug. 2, 2021, 104.
Reexamination No. 90/014,540 Applicant Initialed Interview Request filed Jun. 18, 2021, 5.
Reexamination No. 90/014,540 Applicant Summary of Interview with Examiner filed Jul. 28, 2021, 8.
Reexamination No. 90/014,540 Authorization for Internet Communications filed Jun. 8, 2021, 4.
Reexamination No. 90/014,540 Certificate of Service filed Jun. 3, 2021, 6.
Reexamination No. 90/014,540 Communication Regarding Power of Attorney mailed May 26, 2021, 2.
Reexamination No. 90/014,540 Examiner Interview Summary mailed Jun. 30, 2021, 21.
Reexamination No. 90/014,540 Exhibit 2022, "Accelerated Production of Antigen-Specific T-Cells for Pre-Clinical and Clinical Application Using Gas-Permeable Rapid Expansion Cultureware", Journal of Immunotherapy, 33:3 305-15, Apr. 2010 filed Jul. 12, 2021, 20.
Reexamination No. 90/014,540 Exhibit 2023, "Large-Scale Ex Vivo Expansion and Characterization of Natural Killer Cells for Clinical Applications", Cytotherapy, 2012:14-1131-1143 filed Jul. 12, 2021, 14.
Reexamination No. 90/014,540 Exhibit 2024, "Optimizing the production of suspension cells using the G-Rex "M" Series", Molecular Therapy-Methods & Clinical Development (2014) 1, 14015; doi: 10.1038/mtm2014.15, published Online May 14, 2014 filed Jul. 12, 2021, 10.
Reexamination No. 90/014,540 Exhibit 2025, "Simplified Method of the Growth of Human Tumor Infiltrating Lymphocytes in Gas-Permeable Flasks to Nos. Needed for Patient Treatment", Journal of Immunotherapy, vol. 35, No. 3, 283-292 (Apr. 2012) filed Jul. 12, 2021, 11.
Reexamination No. 90/014,540 Information Disclosure Statement filed Jun. 22, 2021, 15.
Reexamination No. 90/014,540 Information Disclosure Statement filed Jun. 28, 2021, 6.
Reexamination No. 90/014,540 Information Disclosure Statement filed Sep. 1, 2021, 6.
Reexamination No. 90/014,540 Litigation Search Report dated Aug. 11, 2021, 85.
Reexamination No. 90/014,540 Non-Final Office Action mailed Apr. 12, 2021, 30.
Reexamination No. 90/014,540 Notice of Intent to Issue a Reexamination Certificate mailed Oct. 15, 2021, 13.
Reexamination No. 90/014,540 Patent Owner's Response to Office Action, filed Jul. 12, 2021, 95.
Reexamination No. 90/014,540 Power of Attorney filed May 21, 2021, 6.
Reexamination No. 90/014,540 Reexamination Certificate for U.S. Pat. No. 9,441,192 issued Oct. 29, 2021, 2.
Reexamination No. 90/014,540 Request for Extension of Time filed Jun. 2, 2021, 7.
Reexamination U.S. Appl. No. 90/019,042 Notice of Intent to Issue Ex Parte Reexamination Certificate mailed Mar. 7, 2023 (4 pages).
Civil Docket for Case # 0:13-cv-00210-DWF-TNL, Jul. 20, 2023 (95 pages).
Civil Docket for Case # 0:20-cv-00700-DWF-TNL, Jul. 20, 2023 (36 pages).
Docket No. 293, Letter seeking reconsideration re '192 "more than 2.0 cm" limitations, *Corning Incorporated v. Wilson Wolf Manufacturing Corp. and John R. Wilson*, Civil File No. 20-cv-00070 (DWF/TNL) (D. Minn.), Feb. 8, 2023 (3 pages).
Docket Nos. 306 and 306-1, Letter seeking reconsideration re '192 and whether it encompasses scaffolded embodiments and accompanying Exhibit A, *Corning Incorporated v. Wilson Wolf Manufac-*

(56) References Cited

OTHER PUBLICATIONS

*turing Corp. and John R. Wilson*, Civil File No. 20-cv-00070 (DWF/TNL) (D. Minn.), Mar. 16, 2023 (7 pages).

Docket Nos. 307 and 307-1, Letter seeking reconsideration re '443 construction of scaffolds/shelves limitations and accompanying Exhibit A, *Corning Incorporated v. Wilson Wolf Manufacturing Corp. and John R. Wilson*, Civil File No. 20-cv-00070 (DWF/TNL) (D. Minn.), Mar. 16, 2023 (13 pages).

Docket No. 347, Memorandum Opinion and Order, *Corning Incorporated v. Wilson Wolf Manufacturing Corp. and John R. Wilson*, Civil File No. 20-cv-00070 (DWF/TNL) (D. Minn.), May 8, 2023 (14 pages).

Docket Nos. 335 and 335-1 through 335-7, Declaration of Maury D. Cosman in support of defendants' memorandum in response to plaintiff's motion for partial summary judgment and accompanying Exhibit A through G, *Corning Incorporated v. Wilson Wolf Manufacturing Corp. and John R. Wilson*, Civil File No. 20-cv-00070 (DWF/TNL) (D. Minn.), Apr. 14, 2023 (59 pages).

Docket No. 323, Declaration of Jeffrey J. Chalmers, Ph.D. in support of Corning Incorporated's Motion for Partial Summary Judgment of Non-Infringement of the '192 and '443 patents, *Corning Incorporated v. Wilson Wolf Manufacturing Corp. and John R. Wilson*, Civil File No. 20-cv-00070 (DWF/TNL) (D. Minn.), Mar. 24, 2023 (49 pages).

Report of Dr. Maury D. Cosman on Infringement of the Asserted Claims of U.S. Pat. No. 9,732,317 by Corning's Hyperstack Product, submitted in regard to *Corning Incorporated v. Wilson Wolf Manufacturing Corp. and John R. Wilson*, Civil File No. 20-cv-00070 (DWF/TNL) (D. Minn), Jan. 30, 2023 (45 pages).

Defendants' Rule 26(a)(2)(C) Expert Disclosure, *Corning Incorporated v. Wilson Wolf Manufacturing Corp. and John R. Wilson*, Civil File No. 20-cv-00070 (DWF/TNL) (D. Minn.), Jan. 30, 2023 (11 pages).

Memorandum Opinion and Order from Civil case No. 20-700-DWF-TNL, dated May 27, 2022, 28 pgs.

Memorandum Opinion and Order from Civil Case No. 20-700 (DWF/TNL), filed Aug. 7, 2024, 69 pgs.

Office Action in ExParte Reexamination 90019274 dated Aug. 7, 2024, 42 pgs.

Electronic Acknowledgement Receipt from Information Disclosure Statement Submission in Reexamination U.S. Appl. No. 90/019,274, filed May 28, 2024, 9 pgs.

Reply of Third-Party Requester Corning Incorporated to Patent Owner's Statement Under 35 U.S.C. 304 in Reexamination U.S. Appl. No. 90/019,274, filed May 7, 2024, 26 pgs.

Exhibit 1040 Reply Declaration of Charles L. Crespi, Ph. D. Pursuant to 37 C.F.R. 1.132, Reexam U.S. Appl. No. 90/019,274, dated May 3, 2024, filed May 8, 2024, 7 pgs.

Exhibit 1041 Thermo Electron Corporation (Marietta, Ohio), Model 3110 Series, Forma Series II Water Jacketed CO2 Incubator, Operating and Maintenance Manual, Manual No. 703310, Rev. 14, Nov. 7, 2003, 61 pgs.

Electronic Acknowledgement Receipt from Reexamination U.S. Appl. No. 90/019,274, filed May 8, 2024, 3 pgs.

Exhibit 1042 Notice of Intent to Issue Ex Parte Reexamination Certificate in Reexamination Control No. U.S. Appl. No. 90/019,274, mailed Mar. 7, 2023, filed in Reexamination U.S. Appl. No. 90/019,274 on May 8, 2024, 5 pgs.

Certificate of Service filed in Reexam U.S. Appl. No. 90/019,274 on May 8, 2024, 1 pg.

Certificate of Service filed in Reexam U.S. Appl. No. 90/019,274 on May 7, 2024, 1 pg.

Electronic Acknowledgement Receipt from Reexamination U.S. Appl. No. 90/019,274, filed May 7, 2024, 2 pgs.

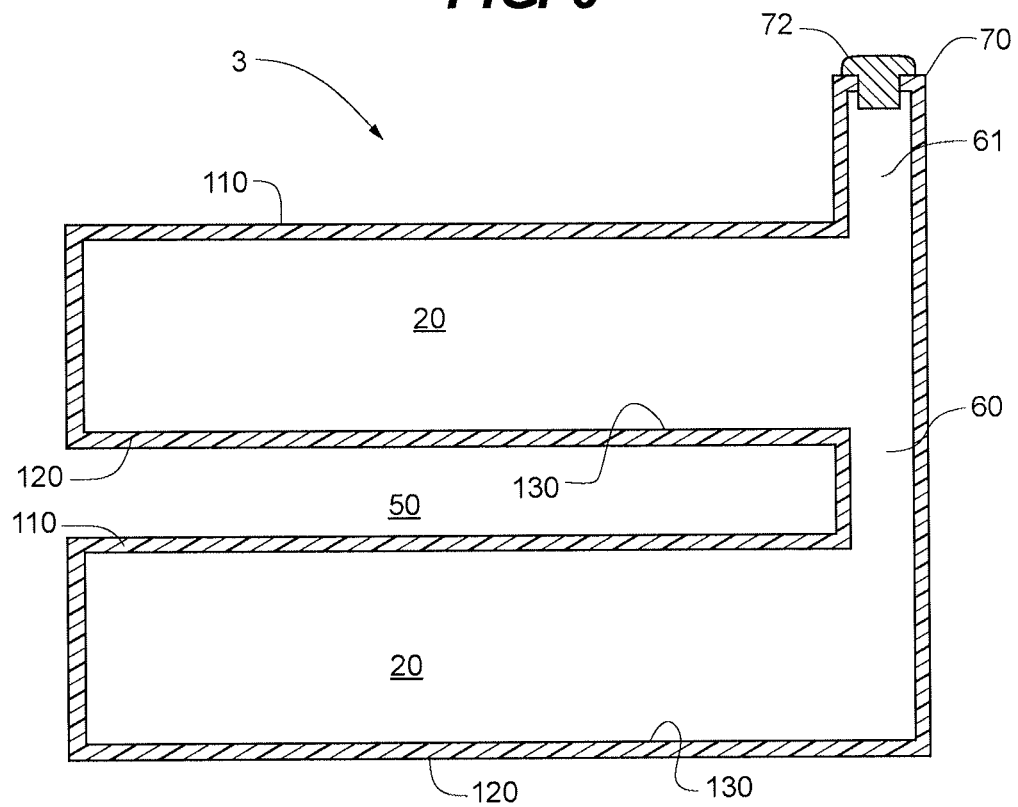

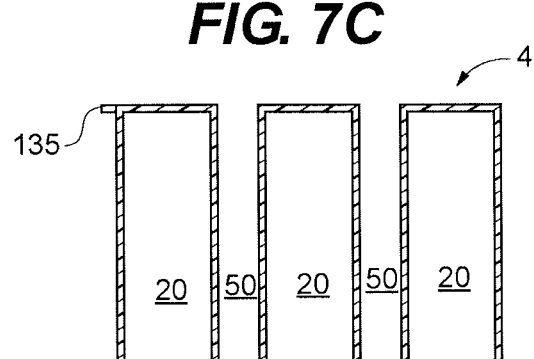
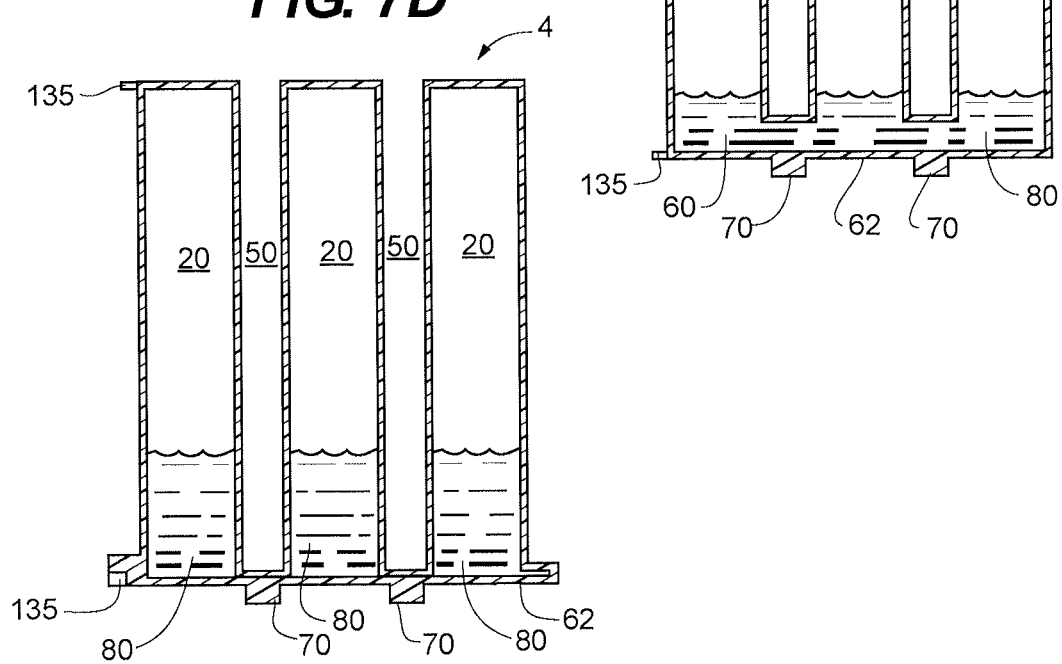
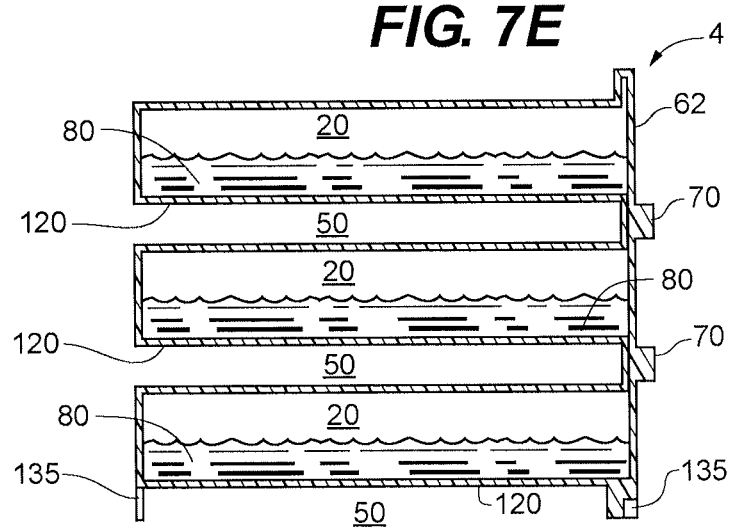

A HUMIDIFIER CAN BE ADDED BETWEEN GAS SUPPLIER AND CELL FACTORY IF REQUESTED (E.G DURING CONTINUOUS GASSING)

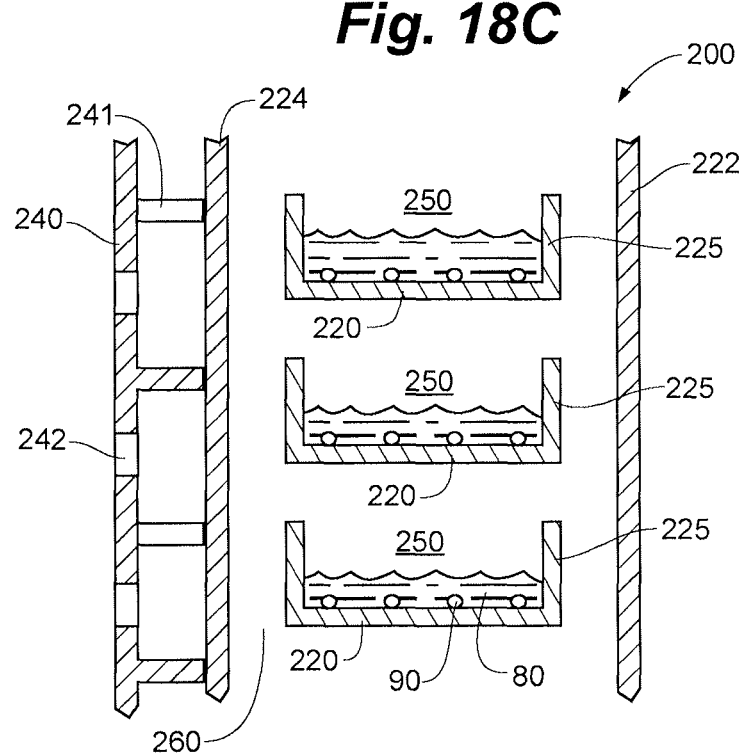

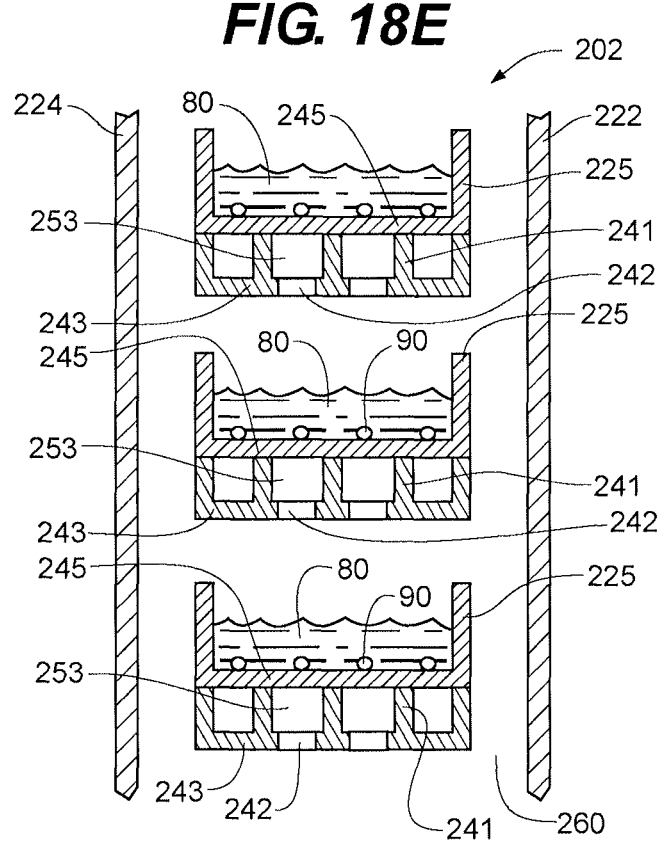

HIGHLY EFFICIENT GAS PERMEABLE DEVICES AND METHODS FOR CULTURING CELLS

RELATED APPLICATION

The present application is a continuation of U.S. application Ser. No. 15/643,621 filed Jul. 7, 2017, which is a continuation of U.S. application Ser. No. 14/321,933 filed Jul. 2, 2014, issued as U.S. Pat. No. 9,732,317, which is a continuation of U.S. application Ser. No. 11/952,848 filed Dec. 7, 2007, issued as U.S. Pat. No. 8,809,044, which claims the benefit of U.S. Provisional Application No. 60/873,347 filed Dec. 7, 2006, all of which are incorporated herein in their entirety by reference.

GOVERNMENT INTERESTS

This invention was made in part with U.S. Government support under National Institutes of Health Small Business Innovative Research Grant DK0659865 "Islet culture, shipping, and infusion device". The U.S. Government may have certain rights in this invention.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, and all of the patents and applications naming John Wilson as an inventor, are hereby expressly incorporated herein by reference. More generally, documents or references are cited in this text, and, each of these documents or references ("herein-cited references"), as well as each document or reference cited in each of the herein-cited references (including any manufacturer's specifications, instructions, etc.), is hereby expressly incorporated herein by reference.

1. Technical Field

This invention relates to methods and devices that improve cell culture efficiency. They include the use of gas permeable culture compartments that reduce the use of space while maintaining uniform culture conditions, and are more suitable for automated liquid handling. They include the integration of gas permeable materials into the traditional multiple shelf format to resolve the problem of non-uniform culture conditions. They include culture devices that use surfaces comprised of gas permeable, plasma charged silicone and can integrate traditional attachment surfaces, such as those comprised of traditional tissue culture treated polystyrene. They include culture devices that integrate gas permeable, liquid permeable membranes.

2. Discussion of Limitations of Conventional Technologies Described in Related Art The culture of cells is a central element of biotechnology. Tissue culture flasks are devices commonly used for cell culture because they allow adherent and non-adherent cell types to be cultured in them, are disposable, and can function in a static mode without need for equipment to perfuse medium. Traditional flasks have one culture compartment. Their design requires a gas-liquid interface to be present within the device for gas exchange of the culture. Culture medium must reside at a very low height so that oxygen delivery to the cells is not compromised. The height of medium that is recommended for tissue culture flasks is between 2 mm and 3 mm. However, the body of the flask must be large enough to hold gas and allow access to the medium, typically by use of a pipette. Thus, flasks have a large device volume relative to the amount of medium they contain. For example, the body of a typical T-175 flask has a footprint approximately 23 cm long by 11 cm wide, is about 3.7 cm tall, and therefore occupies about 936 $cm^3$ of space. However, it typically operates with about 50 ml of medium. Thus, the medium present in the flask body (50 ml), relative to the space occupied by the flask body (936 $cm^3$) demonstrates that only about 5% of the flask's volume is occupied by medium. Furthermore, dividing the volume of space occupied by the body of the flask (936 $cm^3$) by the surface area for cells to reside upon (175 $cm^2$) shows that the volume of space occupied by the flask is over 5 times the surface area it provides for cells to reside upon. Flasks are manufactured with various amounts of surface area for cells to reside upon, typically ranging from 25 $cm^2$ to 225 $cm^2$ in area, and therefore only have a small culture capacity. As more and more flasks are used during culture scale up, the overall amount of space they occupy relative to the small medium volume and limited culture surface area they provide creates an inherently inefficient use of space that burdens the culture process with excess cost related to shipping, sterilization, storage, incubator space, and disposal. This problem is compounded by the substantially increased labor and contamination risk.

Multi-shelved flasks, such as the NUNC Cell Factory (U.S. Pat. No. 5,310,676) and CORNING® CELLSTACK® (U.S. Pat. No. 6,569,675), attempt to address inefficient flask scale up by stacking shelves in the vertical direction to create multiple culture compartments within one flask. This creates more surface area within one device and therefore allows more cells to reside in the multi-shelved flask than the traditional flask. In this manner, one multi-shelved flask can replace numerous traditional flasks. The multi-shelved flask can be configured so that medium can be accessed through a common collection point, precluding the need for pipette access to each culture compartment. That allows the distance between each shelf of the multi-shelved flask to be reduced relative to the height of the traditional flask. For example, the space between shelves of the NUNC Cell Factory is about 1.4 cm, as opposed to the 3.7 cm distance between the bottom and top of a typical T-175 flask creating some improvement in the use of storage, shipping, sterilization, culture, and disposal space. A vent in the multi-shelved flask allows gas exchange with the ambient atmosphere in order to adjust pH, provide oxygen, and to help maintain temperature control. However, gas at any given location within the multi-shelved flask resides at a different distance from the vent location. Since the distance between gas at the farthest point and gas at the closest point to the vent increases as the number of culture compartments within the multi-shelved flask is increased during scale up, gradients in $CO_2$ and $O_2$ concentrations can develop throughout the gas within the multi-shelved flask. Therefore, the multi-shelved flask design has an inherent potential for non-uniform culture conditions to exist throughout the device and the problem is compounded during scale up.

There are a number of static cell culture devices that perform gas transfer by making the lower wall of the device gas permeable. Gas diffuses through the gas permeable lower wall in response to concentration gradients that develop between the culture medium and the ambient gas.

This approach eliminates the gas-liquid interface as the sole source of gas exchange. Since the surface that cells reside upon is gas permeable, more uniform culture conditions can exist throughout the culture than the multi-shelved flask. Bags are static gas permeable devices that integrate a single culture compartment. To scale a culture up, the bag must elongate in the horizontal direction to create more surface area for cells to reside upon. Thus, they quickly become unwieldy and outsize cell culture incubators during scale up. Bags are commercially available from OriGen Biomedical Group (ORIGEN PERMALIFE Bags), Baxter (LIFE-CELL® X-FOLD related to U.S. Pat. Nos. 4,829,002, 4,937,194, 5,935,847, 6,297,046 B1), Medtronic (SI-CULTURE, U.S. Pat. No. 5,686,304), Biovectra (VECTRA-CELL), and American Fluoroseal (VUELIFE Culture Bag System, covered by U.S. Pat. Nos. 4,847,462 and 4,945,203). Gas permeable cartridges are devices that operate in the same manner as bags, except they have rigid sidewalls. Commercially available gas permeable cartridges include CLINICELL® Culture Cassettes provided by Laboratories MABIO-INTERNATIONAL® and OPTICELL® gas permeable cartridges (U.S. Pat. Nos. 6,455,310 and 6,410,309) provided by BioChrystal Ltd. As with bags, in order to provide more surface area for cells to reside upon, these devices must elongate in the horizontal direction. In U.S. Pat. No. 6,821,772, the inventor of OPTICELL® has proposed multiple gas permeable compartments. Unfortunately, the proposal merely increases the number of culture compartments in the horizontal direction. Thus, regardless of the number of culture compartments, increasing the culture capacity of these devices requires that they be made larger in the horizontal direction. None of these gas permeable devices are capable of scaling in the vertical direction.

In an attempt to utilize space more efficiently, U.S. Pat. No. 6,673,595 describes the scale up of OPTICELL® gas permeable cartridges by stacking individual, physically distinct, cartridges in the vertical direction and handling each individual cartridge with a very complex automated system. This scale up approach deviates markedly from the simplicity afforded by the traditional multi-shelved flask.

U.S. Pat. No. 6,759,245 described a multilayered gas permeable culture device that separates oxygen delivery from medium delivery by use of a gas permeable, liquid impermeable membrane. This invention is based on the discovery that if the flows of liquid medium and oxygenated fluid are separated by a gas permeable, liquid impermeable membrane, and the cells are grown attached to the liquid side of the membrane, the device can be used to culture cells with the transport of oxygen through the membrane without regard for the flow rate of liquid medium passing through the device. The advantage being that the flow rate of liquid medium is no longer dependent on the need to carry oxygen to the cells. However, although the flow of medium is substantially lowered, as it is only needed to carry substrates such as glucose, it precludes the ability to culture suspension cells since they will be washed from the device during use. In this approach, cells must be attached to a collagen matrix. Another disadvantage is the need to perfuse the gas space and/or the liquid space. This requires pumps, fluid lines, and a greatly elevated level of complexity relative to traditional multiple shelf flasks. Thus, this approach has not been commercialized.

Gas permeable devices that make more efficient use of space are described in co-pending U.S. patent application Ser. No. 10/961,814 (Wilson et al.). Among the gas permeable devices described in Wilson et al. '814 are those that allow culture scale up in the vertical direction while retaining the simplicity of the traditional multi-shelved flask. For example, Wilson et al. '814 describe the vertical scale up of gas permeable devices comprised of shelves stacked one above the other for cells to reside upon. Gas transfer occurs through the walls of the device. Unlike the scale up of traditional gas permeable devices, increasing culture size can be achieved by increasing the size of the device in the vertical direction as opposed to the horizontal direction. Since there is no need for a gas-liquid interface, this allows optimal space efficiency during vertical scale up of a culture. A more compact device is attained relative to the multi-shelved flask. Attributes not possible in the traditional multi-shelved flask are present. For example, the device can be inverted to allow adherent cells to be cultured on the upper and lower surfaces of the stacked shelves to further optimize space efficiency. The invention described herein expands upon the gas permeable advantages described in co-pending Wilson et al. '814 to create new geometry that provides a superior alternative to the traditional multiple shelf flask.

It is an object of the present invention to provide improved cell culture devices and methods that minimize the potential for non-uniform culture conditions to exist throughout the device, allow space efficient culture scale up of adherent or suspension cells, are easy to use, can function without need to perfuse medium or gas, and allow the user to make effective use of the upper, lower, or sidewall surfaces of each culture compartment. Still further objects and advantages will become apparent from consideration of the ensuing description and drawings.

SUMMARY OF THE INVENTION

The present invention overcomes many of the disadvantages of existing static cell culture devices by integrating at least two gas permeable culture compartments that, at least in part, maintain a gas space between them in order to allow gas to contact the gas permeable area of the culture compartments. This allows each culture compartment to exchange gas directly with the gas space adjacent to the culture compartment, minimizing the potential for non-uniform culture conditions. Selected surfaces of the culture compartments can be made gas permeable to provide gas exchange on the surface opposite cells and/or adjacent to cells. Surfaces inside the culture compartments can be comprised of various materials to provide optimal surfaces for cells to reside upon. Surface area inside the culture compartments can be increased if desired, such as may be the case when adherent cells or cells that thrive in a three dimensional matrix are cultured. It is also possible for cells to reside directly upon the gas permeable material of the culture compartments. Scaling the device can be accomplished by adding culture compartments such that, at least in part, a gas space exists between each culture compartment in order to allow gas to contact the gas permeable area of the culture compartments. Access to the culture compartments can occur by way of a common manifold, common manifolds, or by discrete access to each compartment. With this configuration, it is possible to scale cultures in a simple format that is easy to use, makes efficient use of space, and minimizes the potential for non-uniform culture conditions to occur. Various features can be included, and configurations can be structured, to provide additional benefits including the ability for the device to be operated in more than one position, allow the culture of adherent cells, allow the culture of suspension cells, allow co-culture, prevent cells from exiting their respective culture compartments during routine handling, minimizing feeding frequency, replicate traditional flask protocols, allow the surface area for cells to reside upon to be increased or decreased during culture, allow the ratio of medium volume to the surface area for cells to reside upon to be increased or decreased during culture, and/or to allow the cells to reside on or in proximity of alternative materials.

In one aspect of the present invention, each culture compartment includes a first wall and an opposing second wall, the first wall and/or the second wall being comprised of gas permeable material, and a gas space is present between at least a portion of each culture compartment.

In another aspect of the present invention, each culture compartment includes several walls, including but not limited to a first wall and an opposing second wall, a third wall and an opposing fourth wall, and a fifth wall, the first wall and/or second wall and/or third wall and/or fourth wall and/or fifth wall being comprised of gas permeable material, and a gas space is adjacent to at least the gas permeable portion of each culture compartment.

In another aspect of the present invention, the culture compartments are connected in parallel by one manifold. The manifold can be configured to prevent gas from displacing medium held within the culture compartments, and/or can be configured to retain cells in the culture compartments during handling, and/or can be configured to retain medium and gas in the culture compartments.

In another aspect of the present invention, the culture compartments are connected in parallel by more than one manifold.

In another aspect of the present invention, the height of the culture compartments can change.

In another aspect of the present invention, a culture compartment support resides between culture compartments to maintain the culture compartments in a substantially horizontal position and/or allow gas to contact the gas permeable surfaces of the culture compartments.

In another aspect of the present invention, walls of the culture compartments include projections that make contact with at least one of its neighboring culture compartments in order to maintain the culture compartments in a substantially horizontal position and allow gas to contact the gas permeable surfaces of the culture compartments.

In another aspect of the present invention, structure is provided to prevent walls of the culture compartments from making contact with neighboring walls of the culture compartment.

In another aspect of the present invention, the culture compartments are connected in series.

In another aspect of the present invention, direct access to each of the culture compartments is possible.

In another aspect of the present invention, contact between ambient gas and the gas space of the gas permeable multi-shelf device can be selectively terminated, restricted, or unrestricted.

In another aspect of the present invention, a method of expanding cells from one culture compartment to multiple culture compartments is possible.

In another aspect of the present invention, when the gas permeable multi-shelf culture device is oriented such that cells are residing on the lower most culture surfaces of the culture compartments, at least a portion of one culture compartment does not have a culture compartment directly above it in order to facilitate microscopic evaluation.

In another aspect of the present invention, when the gas permeable multi-shelf culture device is oriented such that cells are residing on the lower most culture surfaces of the culture compartments, the gas space between the lowest culture compartment and the culture compartment residing above it allows light to be present above the lowest culture compartment to facilitate inverted microscopic evaluation of the lowest culture compartment.

In another aspect of the present invention, a method of co-culturing cells is possible by seeding cells to a culture surface and repositioning the device to allow another inoculum of cells to gravitate to a different culture surface.

In another aspect of the present invention, a method of culturing cells on a particular surface, at a particular oxygen tension, and a particular medium height, and/or at a particular medium volume to surface area ratio is available by merely rotating the device to reposition the cells from surface to surface. It is also possible to culture at least five different cell lines, each residing on a different wall of the culture compartment.

In another aspect of the present invention, culture compartments are fabricated as an integral unit to minimize the number of seals.

In another aspect of the present invention, the gas permeable multi-shelf device can be configured to retain the features of commercially available, traditional multiple shelf flasks while resolving the problems of non-uniform culture conditions.

In another aspect of the present invention, the use of gas permeable, liquid permeable materials are disclosed for use in a gas permeable cell culture device that includes a culture compartment support and a sterility barrier between the gas space and the ambient gas.

In another aspect of the present invention, structuring gas permeable devices with plasma charged silicone for the purpose of minimizing migration to other surfaces is disclosed.

BRIEF DESCRIPTION OF THE DRAWINGS

FIG. 6 shows a cross-sectional view of a gas permeable multi-shelf device that is configured with a gas trap to prevent gas from displacing medium from within the culture compartments.

FIG. 7C, FIG. 7D, and FIG. 7E show a cross-sectional view of one embodiment of a gas permeable multi-shelf device that is configured to allow medium and gas to reside in the culture compartments at predetermined volumes.

FIG. 18C, FIG. 18D, and FIG. 18E show embodiments of gas permeable multi-shelf devices configured to resolve the problem of non-uniform culture conditions while integrating the features of commercially available, traditional multiple shelf flasks. In one embodiment, gas transfer occurs directly through the walls of the device, allowing direct gas exchange between the gas above each culture compartment and that of the ambient environment. In another embodiment, a gas space resides within the device, allowing gas exchange of the gas within the device through the walls of the gas space. The upper wall of the gas space can be adapted to allow gas transfer independent of a gas-liquid interface and/or the lower wall of the gas space can be adapted to allow gas transfer to the culture by way of a gas-liquid interface. In another embodiment, the gas space is in communication with ambient gas by way of a gas permeable device wall, and a gas permeable upper wall of the gas space acts as the lower wall of the culture compartment, allowing gas transfer to occur to the culture independent of the gas-liquid interface.

DETAILED DESCRIPTION OF THE INVENTION

Figure 1A:
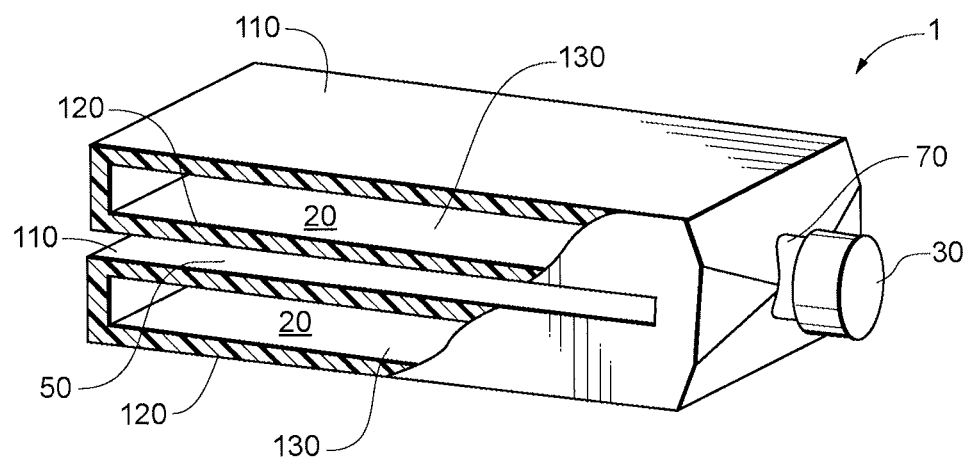
FIG. 1A and FIG. 1B illustrate an embodiment of a gas permeable multi-shelf device that is configured for gas exchange to occur directly through the walls of the culture compartments. The culture compartments are connected in parallel with a manifold to form an integral unit, including the presence of a gas space between the culture compartments. An access port allows fluid to move into and out of the gas permeable multi-shelf device.
Figure 1B:
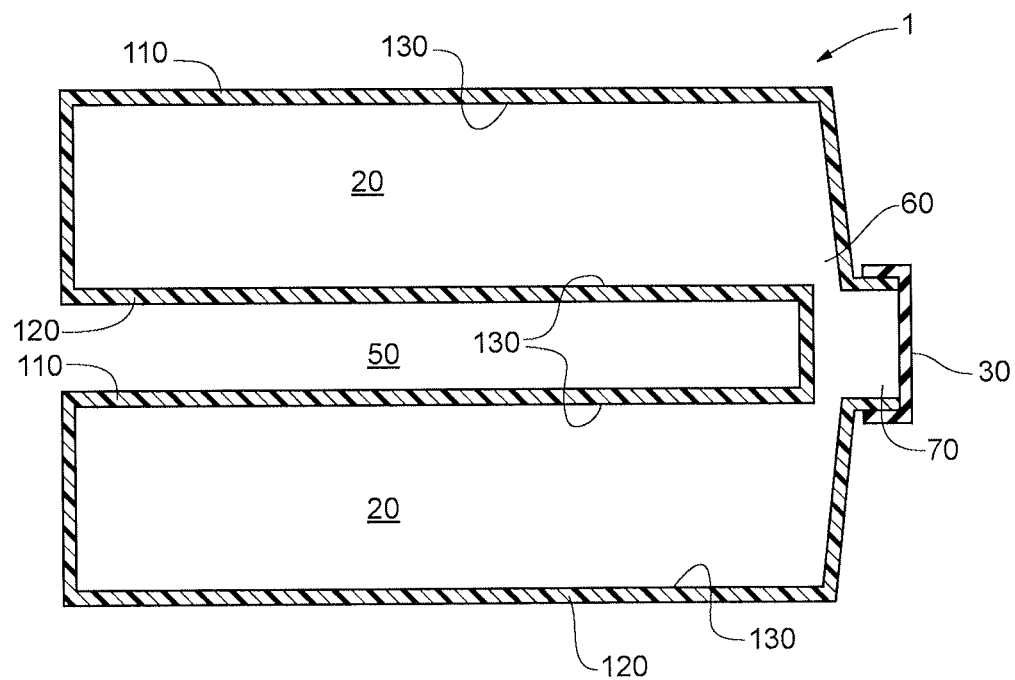

FIG. 1A and FIG. 1B are useful for illustrating some of the basic attributes of the invention. In these illustrations, gas permeable multi-shelved device 1 integrates two gas permeable culture compartments 20 separated in part by gas space 50. Although two culture compartments are shown to allow a description of some of the basic gas permeable multi-shelf device attributes, any additional number can be provided. FIG. 1A shows a perspective view with a sidewall removed to expose the inside of culture compartments 20. FIG. 1B shows a cross-sectional view of gas permeable multi-shelf device 1. Culture compartments 20 are comprised of a first wall 110 and an opposing second wall 120. First wall 110, second wall 120, or both first wall 110 and second wall 120 can be comprised of gas permeable material. First wall 110 and second wall 120 can be secured together without need of a sidewall, such as is the case with traditional cell culture bags. However, a sidewall is preferred to allow a uniform distance between the first and second walls of the culture compartments to exist throughout the culture compartments. Furthermore, when selected walls and sidewalls are comprised of gas permeable material, the gas permeable multi-shelf culture device can be oriented such that it functions in a variety of positions including first wall down, second wall down, or any of the sidewalls down. This allows cells to reside on, in proximity of, any of the walls. When the length, height, and width of the culture compartments differ in dimension, the gas permeable multi-shelf culture device can provide a unique medium height above cells and/or a unique medium to surface area ratio by altering its position during inoculation and/or culture. Depending on orientation during inoculation, cells can gravitate to any surfaces within the culture compartments. For example, in the position of FIG. 1B, cells gravitate toward second wall 120. The surface that cells contact can simply be the inner surface of the culture compartment wall. However, the desired material composition and the geometry of material that cells reside upon may not be that presented by the inner surface of the culture compartment walls. In this event, any component, insert, matrix, or the like that provides the desired material and geometry can be structured into the gas permeable multi-shelf device. Thus, culture surface 130 can simply be the inner surface of a given culture compartment wall, or can be any component, insert, matrix, and the like that resides within the culture compartment. Although not limiting the scope of the invention, but merely for convenience, throughout this application culture surface 130 is depicted on the inner surface of the device walls.

As shown in FIG. 1B, manifold 60 creates a fluid pathway between culture compartments 20. Access port 70 allows fluid and cells to be added and removed. In this illustration, access port 70 includes a neck and cap 30 covers access port 70 in the manner of a traditional flask. However, the access port(s) can be any configuration(s), and can be located in any location(s), that meet the objective of moving fluid into and out of the gas permeable multi-shelved device. Those skilled in the art of cell culture device design will recognize that there are many ways to achieve that objective, including many closed system configurations which may include the use of septums, quick disconnect fittings, or tubing configured for sterile splicing.

Gas space 50 need not be an enclosed aspect of the device. It need not have forced gas flow, or be adapted for forced gas flow, in order for the device to function. In the simplest and preferred form, it is just ambient gas in contact with any or all of the gas permeable portions of the device. However, one or more walls can surround it.

In a simple method of operation, medium and cells are delivered into the gas permeable multi-shelf device, and gas permeable multi-shelf device is placed into a standard cell culture incubator, oriented such that cells gravitate to the desired surface. In a more complex mode of operation, additional inoculations can be undertaken to allow cells to gravitate to additional surfaces. For example, by periodically repositioning the device during inoculation, cells can reside on all culture surfaces.

Each culture surface 130 can be any suitable material, and any shape, that is useful for culturing cells and may be or may not be integral to the walls of the culture compartments. For example, the culture surface could simply be the inner surface of the wall that comprises the culture compartment, and may be tissue culture treated or not. It could be material that is laminated to the wall of the culture compartment such as described in U.S. Pat. No. 5,935,847. It could be a material that is physically separate from the wall of the culture compartment, such as a separate part fabricated of polystyrene that resides upon the wall, and may or may not be affixed to the wall, such as a fibronectin or a collagen matrix insert. There is no restriction on the use of any culture surface that is known to those skilled in the art of cell and tissue culture.

Figure 2:
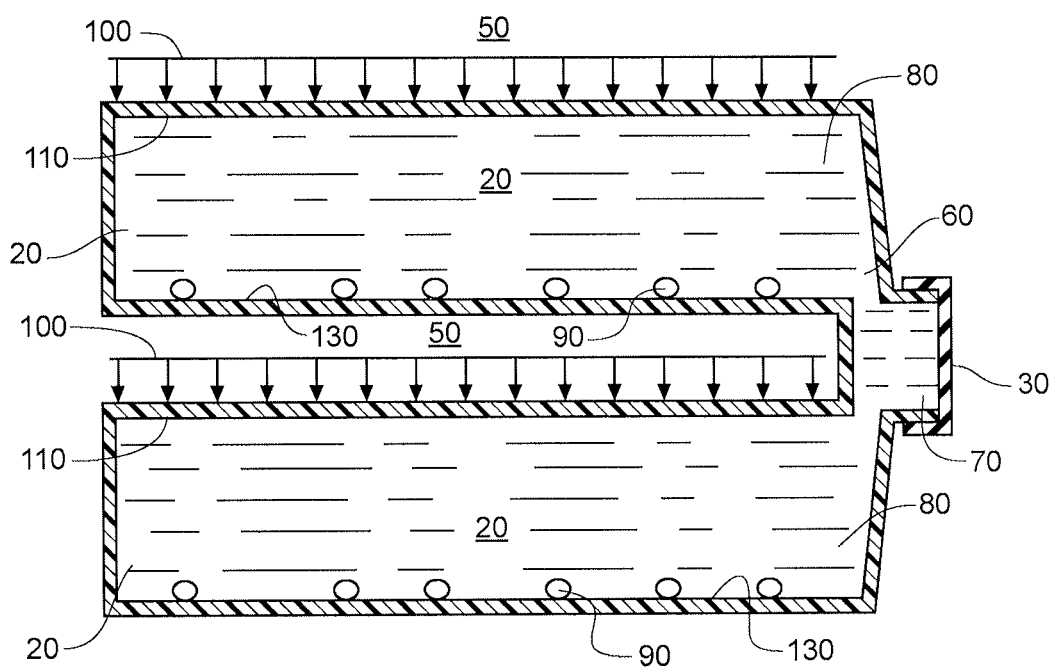
FIG. 2 shows a cross-sectional view of one embodiment of a gas permeable multi-shelf device that is configured to allow gas transfer through a first wall of the culture compartments in order to allow gas exchange via the surface of the medium that resides the furthest distance from cells.

FIG. 2 illustrates how uniform culture conditions can be established with gas exchange across gas permeable first wall 110 of culture compartments 20. Oxygen flux arrows 100 show how, as a result of an oxygen concentration gradient between medium 80 and gas space 50, oxygen is delivered across gas permeable first walls 110 to cells 90 residing on culture surface 130 by way of medium 80. Depending on how much of first wall 110 is gas permeable, up to virtually the entire upper surface of the medium can be simultaneously exposed to the ambient gas surrounding the device, unlike the traditional multiple shelf flask in which ambient gas enters the device at a single gas permeable location(s) that resides at a different distance from every medium location within the device. As described herein, in some embodiments, the gas permeable multi-shelf device is structured with the ability for gas and medium to reside in the culture compartments. Thus, gas can reside on both sides of the gas permeable first wall 110 during operation. In general, gas moves into and out of the culture compartments due to the partial pressure differential between the gas space and the fluid within the culture compartment.

Figure 3:
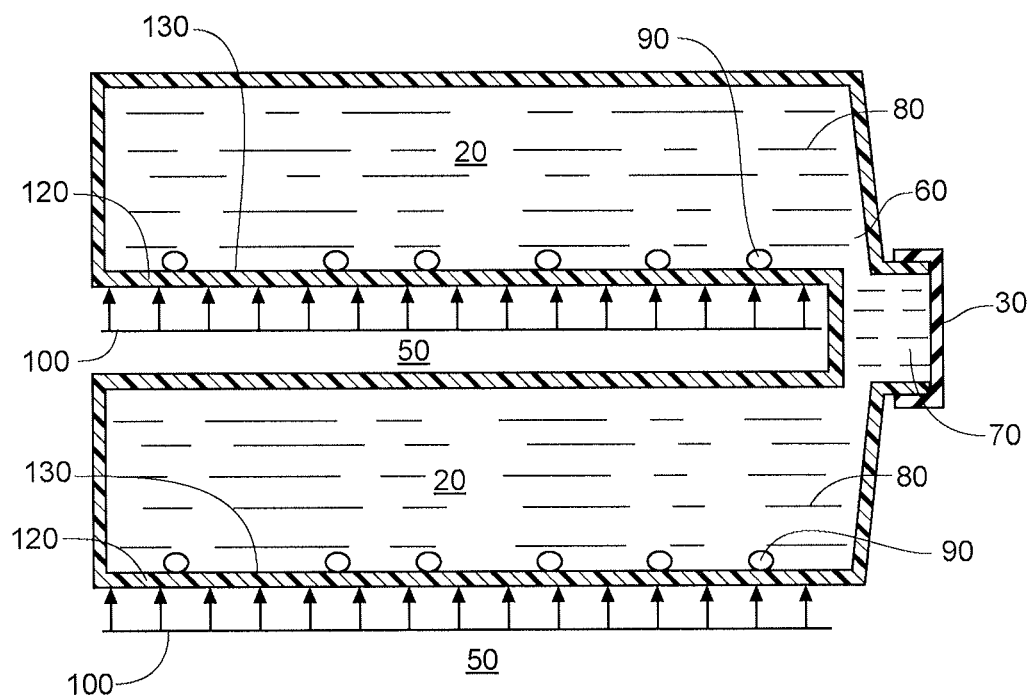
FIG. 3 shows a cross-sectional view of one embodiment of a gas permeable multi-shelf device that is configured to allow gas transfer through a second wall of the culture compartments in order to allow gas exchange in proximity of the cells.

FIG. 3 illustrates gas exchange across gas permeable second walls 120 of the culture compartments. Oxygen flux arrows 100 show how, as a result of a concentration gradient between medium 80 and gas space 50, oxygen is delivered through gas permeable second walls 120 to cells 90 residing in culture compartments 20. In this manner, cells in each cell compartment are closer to the ambient gas than is possible in the traditional multi-shelved flask. Care should be taken to ensure that the materials that comprise culture surface 130 do not impede gas transfer beyond what is needed to oxygenate desired number of cells and maintain proper pH. For example, if gas permeable second walls 120 are constructed of a material with high gas transmission, such as dimethyl silicone, and a less gas permeable culture surface such as polystyrene resides upon the silicone, gas transfer to the cells will be impeded. In general, the material most resistant to gas transmission that resides between the cells and the ambient gas source will be rate limiting. Thus, to optimize the function of the gas permeable multi-shelf device, the design should contemplate the gas transmission of the materials used to construct gas permeable walls, the gas transmission of any additional culture surfaces that are used, and the oxygen demand of the culture. The gas permeable multi-shelf device allows many options for providing acceptable gas exchange and acceptable materials for cells to reside upon. However, if a material is desired for the culture surface that will restrict gas exchange of the culture, it is possible to enhance gas exchange by way of the opposing wall, and/or the sidewalls of the culture compartment.

Figure 4:
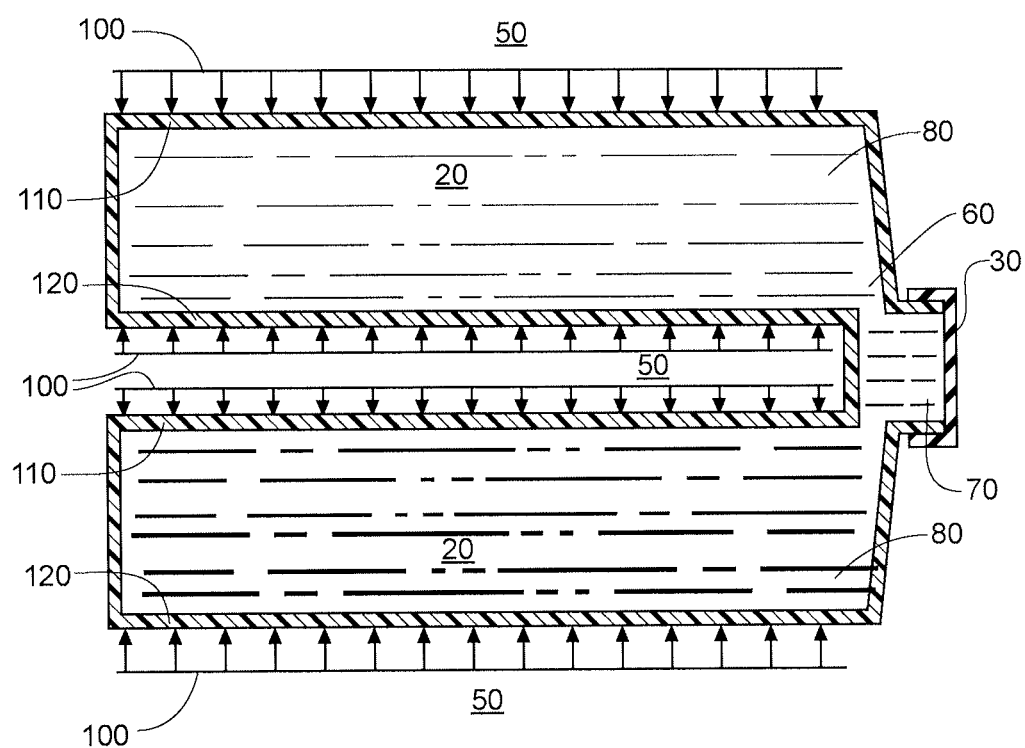
FIG. 4 shows a cross-sectional view of one embodiment of a gas permeable multi-shelf device that is configured to allow gas transfer through a first wall and through a second wall of the culture compartments in order to increase the surface area available for gas exchange.

FIG. 4 illustrates gas exchange across gas permeable second walls 120 and across gas permeable first walls 110 of the culture compartments. Oxygen flux arrows 100 show how, as a result of a concentration gradient between medium 80 and gas space 50, oxygen is delivered to culture compartments 20 by way of gas permeable second walls 120 and gas permeable first walls 110. In this manner, a high level of gas transfer is available to each culture compartment.

Although FIG. 2, FIG. 3, and FIG. 4 show gas transfer through specific walls, any wall of the gas permeable multi-shelf device can be gas permeable. A variety of advantages become available because oxygen can be delivered to cells directly through the surface they reside upon, and/or through the sidewalls of the culture compartments, and/or through the manifold wall(s). Wilson et al. '814 describe the advantages that can be obtained by increasing the height of medium that can reside in a gas permeable culture compartment. Medium height in the gas permeable multi-shelf device can increase far beyond the 2 mm to 3 mm limits of traditional flasks, thereby minimizing the frequency of medium exchange, reducing labor, and reducing contamination risk. Thus, when gas transfer occurs across a gas permeable wall of a culture compartment, it may be beneficial to structure the culture compartment so that the distance between the gas permeable wall and the opposing wall allows medium height to increase. The optimum distance will depend upon the metabolic demand of the culture and the desired frequency of medium exchange.

Figure 5A:
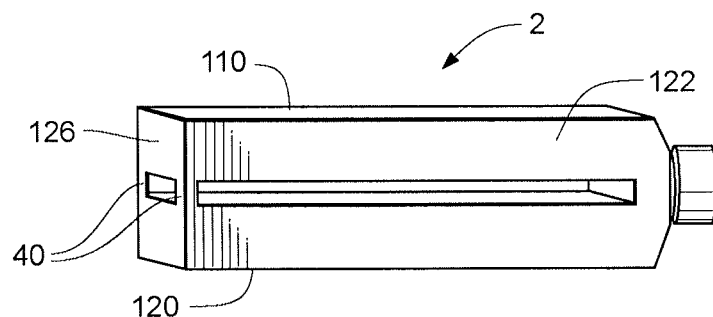
FIG. 5A, FIG. 5B, and FIG. 5C show a perspective view of a gas permeable multi-shelf device that is configured with a first wall and an opposing second wall, a third wall and an opposing fourth wall, and a fifth wall. By selectively fabricating each wall with a predetermined length, width, surface area, and material composition, and each culture surface of a predetermined material and surface area, the user can select from a variety of culture protocols. Thus, by merely altering the orientation of the gas permeable multi-shelf device, the user can expose cells, various types of culture surfaces, culture surface areas, oxygen tension, and medium volume to surface area ratios. For example, when the gas permeable multi-shelf device is oriented as shown in FIG. 5B, medium can reside at a greater height than when the gas permeable multi-shelf device is oriented as shown in FIG. 5A. When the gas permeable multi-shelf device is oriented as shown in FIG. 5C, medium can reside at a height that exceeds what is possible when the device is oriented as shown in FIG. 5A or FIG. 5B.
Figure 5B:
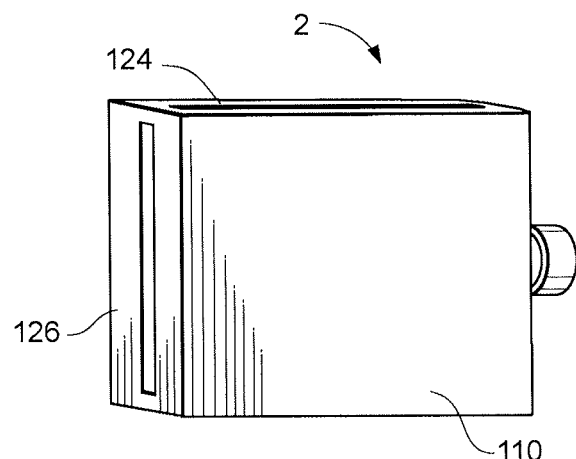
Figure 5C:
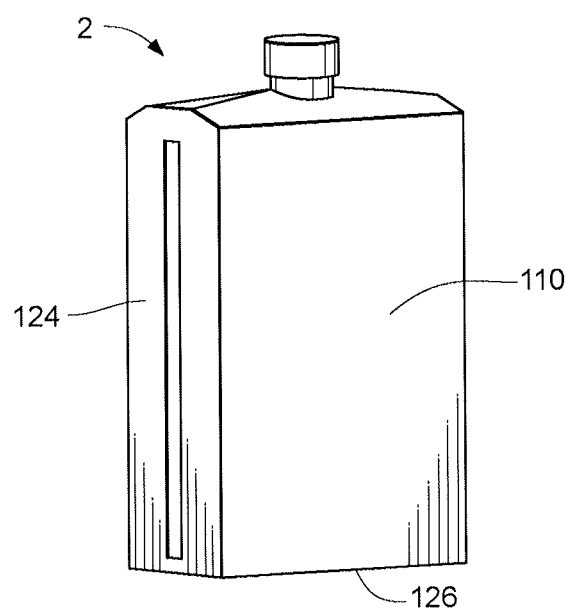

FIG. 5A, FIG. 5B, and FIG. 5C illustrate an example of how a gas permeable multi-shelf device can be positioned to allow many culture options. For example, when first wall 110, and/or second wall 120, and/or third wall 122, and/or fourth wall 124, and/or fifth wall 126 are comprised of material of differing gas permeability, cells can come to reside upon at a different oxygen tension by orienting gas permeable multi-shelf device 2 to a given position. However, the gas permeable material need not differ to allow robust operating protocols. The culture surface, integral or non-integral, in proximity of first wall 110, and/or second wall 120, and/or third wall 122, and/or fourth wall 124, and/or fifth wall 126 can differ in material and/or surface area. When the dimensions of first wall 110, third wall 122, and fifth wall 126 differ, orienting gas permeable multi-shelf device 2 in any position also allows the maximum height of medium to change at any point before or during culture. Altering the shape of the cell compartments can create even more options. For example, an octagonal shape allows additional surfaces for cells to reside upon, as the device is reoriented.

To advance the objective of establishing uniform culture conditions in the gas permeable multi-shelf device, the design should include the objective of placing an approximately equal number of cells within each culture compartment, and facilitating an approximately uniform distribution of those cells throughout each culture compartment. Making the geometry of each culture compartment virtually identical, structuring the opposing walls of each culture compartment to be approximately parallel, and allowing the culture compartments to reside in a horizontal position so that cells can gravitate uniformly upon the culture surface can help achieve that objective. Then, when cells are in a uniform suspension during inoculation, and the culture surface is of uniform geometry, the inoculum will reside at a uniform volume above the culture surface of each culture compartment and cells will settle in a uniform distribution upon the culture surface of each culture compartment. In the case where culture surfaces are not flat, such as when corrugated surfaces are present, configuring the culture compartments to have an equal volume of space above each unit of culture surface area can assist uniform cell distribution during inoculation. For example, if the culture surface was corrugated and the opposing wall was also corrugated, the volume of space between the corrugated opposing wall and the culture surface would remain constant along the length of the culture compartment. Regardless of culture surface geometry, configuring the culture compartments so that an approximately equal volume of inoculum is present at any given section within the culture compartment can help achieve uniform cell distribution.

Preferably, when a manifold is used to deliver medium to the culture compartments, the manifold should be structured to allow inoculum to distribute evenly into each culture compartment and to minimize the number of cells that settle within the manifold. Making the volume of manifold no larger than needed to allow medium to quickly and easily fill the culture compartments is beneficial, since cells residing in the volume of medium retained in manifold will settle to the bottom of manifold and not be at the identical culture conditions as cells residing in the culture compartments. Although manifold volume should be minimized during inoculation to prevent cells from gravitating to undesired areas, it can be useful to allow excess volume of medium to reside in the manifold to reduce device height, since that medium can contribute to the ratio of medium volume to surface area within each culture compartment. Stated differently, medium volume in the manifold can make substrates available to cells residing in the cell compartments.

FIG. 6 shows a cross-sectional view of gas permeable multi-shelf culture device 3 configured to locate gas that may become present within the device into an area where it does not disrupt the establishment of uniform culture conditions. Manifold 60 includes gas trap 61. At least a portion of gas trap 61 is elevated higher than the uppermost culture compartment 20. In this illustration, access port 70 is covered by septum 72. Excess gas in the device rises to gas trap 61, thereby avoiding displacement of medium from any of the culture compartments.

Figure 7A:
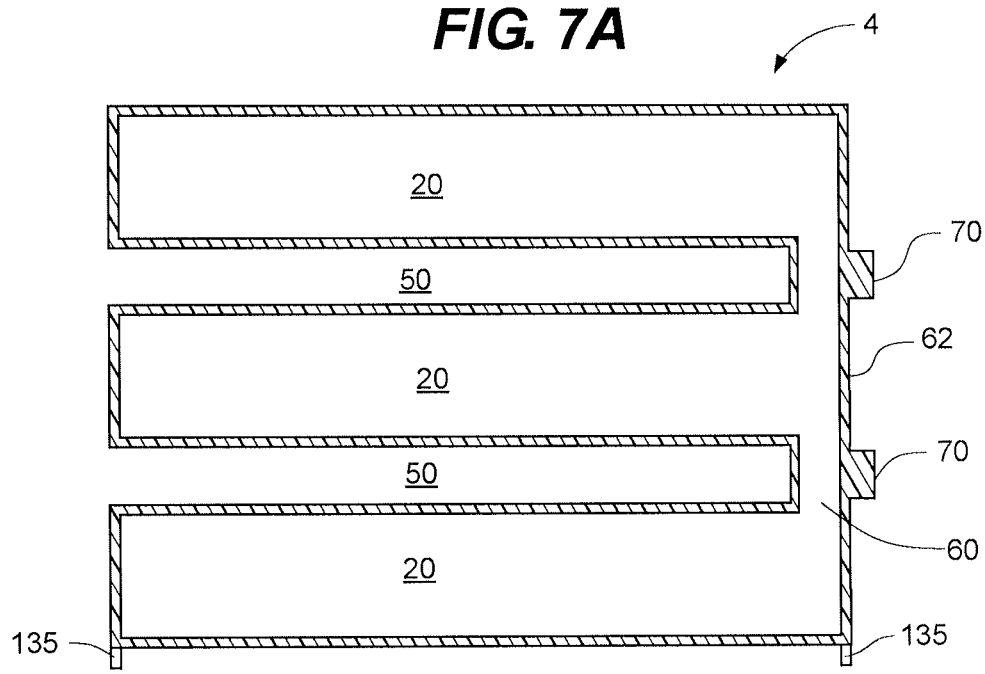
FIG. 7A and FIG. 7B show a cross-sectional view of one embodiment of a gas permeable multi-shelf device that is configured to prevent cells from exiting the culture compartments during routine handling.
Figure 7B:
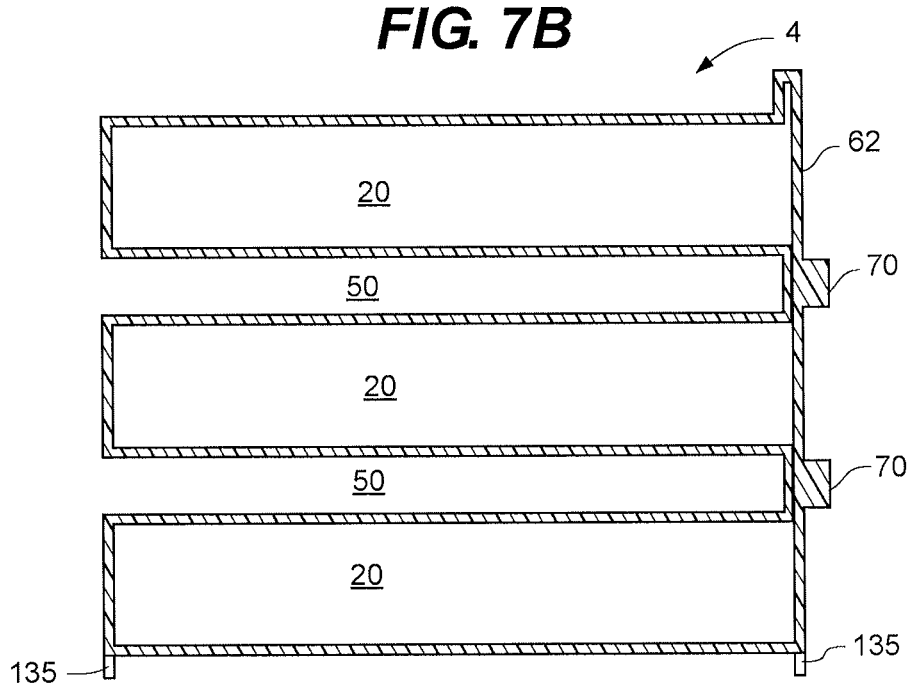

In some applications, it may be desirable to alter the shape or volume of the manifold during use. Structuring the manifold to change shape or volume should be done in a manner that does not allow contamination, such as may be achieved by flexible walls or the use of gaskets or o-rings. For example, it may be desirable to deliver cells to culture compartments by way of a common manifold and prevent cells from moving from one culture compartment to another, or from a culture compartment into the manifold. When the device is to be handled in a manner that may orient the culture compartments in a position that would inadvertently allow cells to exit the culture compartment. Blocking the opening, or openings, of the culture compartments can prevent that. As another example, it may be helpful to alter the volume of medium residing in the manifold at some point during use, as may be the case when cells have attached within the culture compartments and more medium volume is useful for minimizing the feeding frequency. In this case, the manifold can be structured to increase in volume. In other applications, not filling the culture compartment entirely with medium may be advantageous, as may be the case when the desired culture surface area to medium volume ratio dictates that medium should reside at a height that is lower than the height of the culture compartment. FIG. 7A and FIG. 7B show an illustration of how these objectives may be accomplished. In FIG. 7A, manifold wall 62 of gas permeable multi-shelf device 4 is in a first position that allows cells and medium to be introduced into culture compartments 20 by way of manifold 60 via access ports 70. FIG. 7B shows manifold wall in a second position in which manifold 60 has collapsed to block the opening of culture compartments 20, preventing cells or medium from exiting culture compartments 20. Culture compartments 20 can be partially filled with medium so that medium and gas reside in the culture compartments 20, and manifold wall 62 can be moved into the position of FIG. 7B to prevent loss of medium into manifold 60. However, this embodiment also allows gas permeable multi-shelf device 4 to be entirely filled with medium without need of moving manifold wall 62.

FIG. 7C, FIG. 7D, and FIG. 7E show an example of how to partially fill the culture compartments with medium. FIG. 7C shows how gas permeable multi-shelf device 4 can be positioned with manifold 60 oriented below culture compartments 20 and residing in a first open position with a predetermined volume of medium 80 residing in it. The predetermined volume of medium is less than the combined volume of the culture compartments. FIG. 7D shows manifold 60 compressed to drive medium 80 from manifold 60 and into culture compartments 20. FIG. 7E shows gas permeable multi-shelf device 4 oriented horizontally, such that medium 80 and gas reside in each culture compartment. When the manifold is closed, the internal volume of the gas permeable multi-shelf device is reduced, increasing pressure. The pressure increase is related to the ratio of gas to liquid in the culture compartments, the compliance of the culture compartment walls, and the volume of the manifold to the volume of the device. The pressure can eventually be reduced depending on which surfaces of the culture compartments are gas permeable. However, sterile venting of the manifold as it is reduced in volume will relieve pressure more quickly. Those skilled in the art will recognize that there are many ways to structure the manifold to meet these objectives including the use of flexible walls, rigid walls structured with an o-ring in a radial seal arrangement, and other approaches including methods described in Wilson U.S. Pat. No. 7,229,820.

Movement of manifold wall 62 can also be useful when medium is reduced in temperature during use. For example, the culture of islets is often initiated at 37 C and then reduced to 22 C. When the gas permeable multi-shelf device is a closed body and filled with medium, medium will contract as temperature drops. Many gas permeable materials are highly flexible. Thus, the walls of the device can move to maintain contact with the medium when medium contracts. When the walls move, and cells are uniformly distributed on the walls, cells can be displaced from a uniform position to uncontrolled density and thus the viability of the culture can be compromised. Therefore, the ability to alter the volume of the manifold to accommodate a reduction in medium volume can prevent the displacement of the cells from their uniform position.

If desired, feet 135 can elevate the gas permeable multi-shelf device. Feet 135 allow gas to access the underside of the device and/or prevent scratches to the second wall 120. Feet 135 can be present in any embodiment and the upper wall of the device can be adapted to allow one device to reside above the other in an interlocking manner.

Figure 8A:
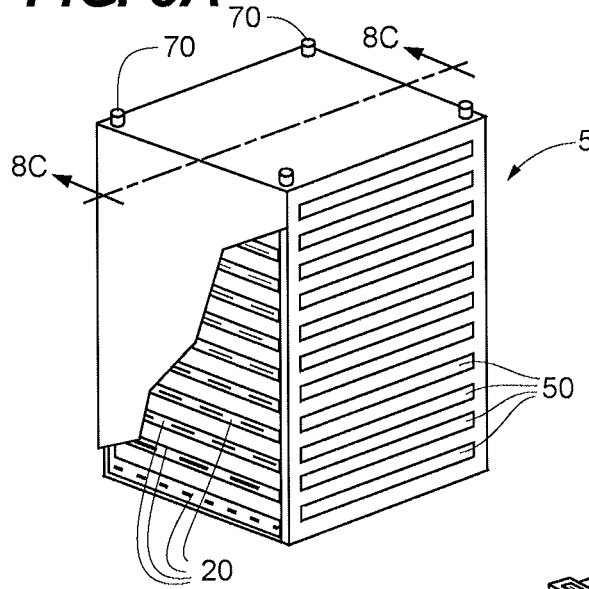
FIG. 8A, FIG. 8B, FIG. 8C and FIG. 8C-1 show a cross-sectional view of one embodiment of a gas permeable multi-shelf device that is configured with two manifolds. Culture compartments are connected in parallel between manifolds, forming an integral unit that includes a gas space adjacent to each culture compartment.
Figure 8B:
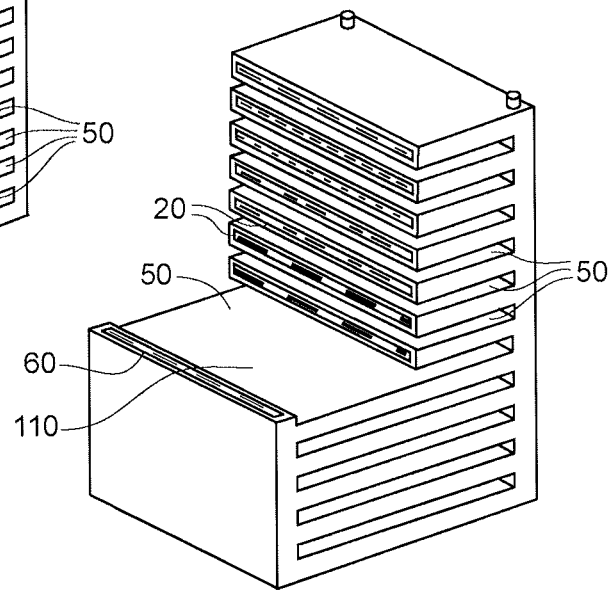
Figure 8C:
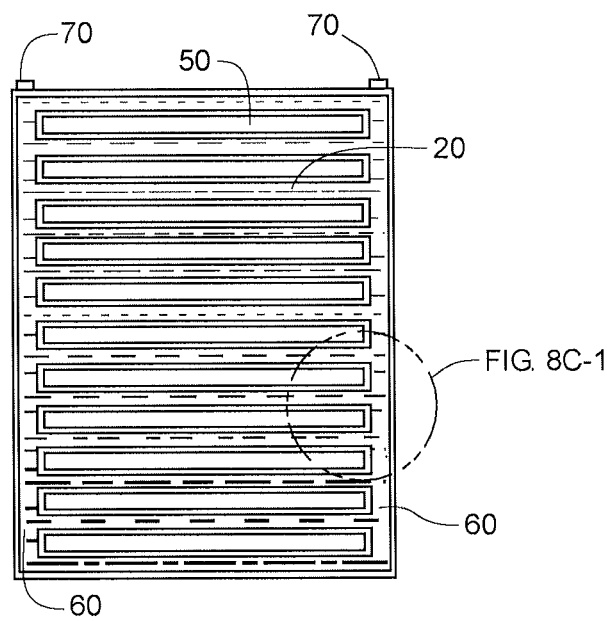
Figures 1, 8C:
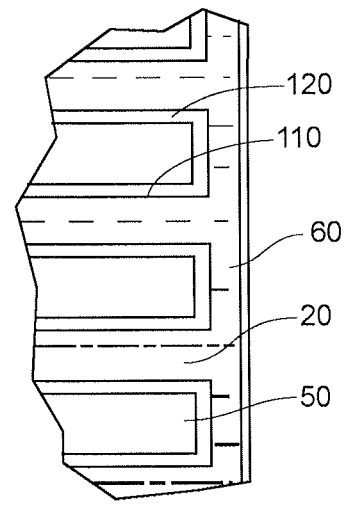

Connecting the culture compartments in parallel with more than one manifold can allow gas to be more easily displaced by liquid entering the device. For example, when one manifold is used, gas is displaced in the opposite direction of medium entering the manifold. As the height of culture compartments is reduced in a gas permeable multi-shelved device with one manifold, tilting the gas permeable multi-shelved device can become necessary to expedite the displacement of gas. Creating an additional manifold can allow the gas to displace in a direction other than that at which medium is entering the device and can reduce or eliminate the need for tilting, thereby simplifying automated fluid handling. In test fixture evaluations intended to determine if culture compartments can be primed without need of tilting the device, priming without tilting was achieved when the volume of medium in the manifolds was about 7.0% of the total volume in the test fixture. FIG. 8A, FIG. 8B, and FIG. 8C show one embodiment that utilizes two manifolds. FIG. 8A shows gas permeable multi-shelf device 5 with a wall removed to expose culture compartments 20. Gas space 50 resides between culture compartments 20. In this illustration, gas space 50 is an opening through the entire body of gas permeable multi-shelf device 5. FIG. 8B shows gas permeable multi-shelf device 5 with a section removed to expose culture compartments 20, first wall 110, and manifold 60. FIG. 8C and FIG. 8C-1 show cross-sectional view 8C-8C of FIG. 8A, exposing culture compartments 20, gas space 50, and manifold 60. In this embodiment, as liquid enters access port 70 and primes manifold 60 and culture compartments 20, gas is displaced via another manifold 60, on the distal end of culture compartments 20, and a secondary access port 70.

Figure 8D:
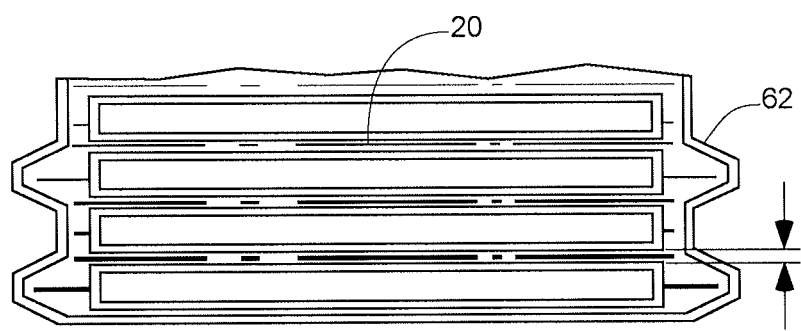
FIG. 8D and FIG. 8E show how the volume of medium and/or the gas permeable surface area to culture compartment volume ratio can be altered before or during the culture process.
Figure 8E:
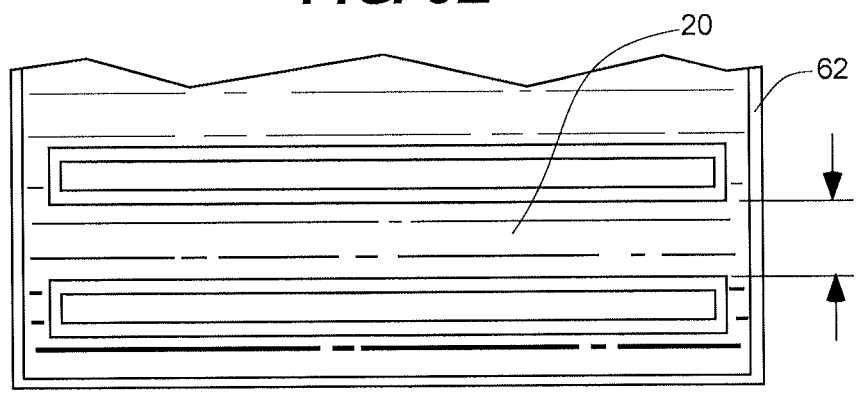

The height of the culture compartments can vary to allow a wider variety of protocols. For example, it may be beneficial if the volume of trypsin used is minimized, or medium height is increased. FIG. 8D and FIG. 8E illustrate one configuration for how that can be accomplished by simply making the device of flexible material that is pleated so that the culture compartment(s) 20 can rise or collapse in height. For example the housing and/or material bounding gas spaces can be flexible. In this manner, the gas permeable multi-shelf device can be expanded to accommodate more, or less, volume in each culture compartment, which may be desired to allow a reduction in feeding frequency, reduced use of trypsin and/or PBS, and/or a change in the gas permeable surface area to culture compartment volume. In this depiction, manifold walls 62 are pleated, but the device can be adapted to allow a change in culture compartment height by a variety other means, including those described in U.S. Pat. No. 7,229,820. Skilled artisans will recognize a variety of ways to allow this attribute.

A factor in optimal performance of the gas permeable multi-shelf device is the orientation of the culture compartments during use. During use, the gas permeable multi-shelf device should preferably be in a substantially horizontal position for uniform cell distribution onto the cell culture surface. The culture compartment support may be as simple as culture compartment support 40, shown in FIG. 5A. In this case, culture compartment support 40 merely provides simple structural support to prevent culture compartments from collapsing upon each other. However, depending on the stiffness of the materials that comprise the walls of the culture compartments, it may be advantageous to form a more elaborate culture compartment support. For example, some important cell culture applications are best conducted in very controlled geometry that is directed at the deposit of cells in very uniform distribution, such as the culture of islets, hepatocytes, and multipotent adult progenitor cells. For example, islets will aggregate when in contact at high surface density, and multipotent adult progenitor cells can differentiate if they are too close to one another. Hepatocytes and islets also have a need for a high rate of gas transmission to retain health. Thus, the most robust culture compartment support will allow a uniform distribution by maintaining the wall that cells are gravitating to in a substantially horizontal position, and not overly restrict gas transmission. To obtain these benefits, the culture compartment support will make contact with the culture compartment walls. The number of contact points, distance between contact points, and amount of surface area of the gas permeable material in direct contact with the culture compartment support are among the design factors to consider. Example 1 and Example 2 provide additional guidance.

Figure 9A:
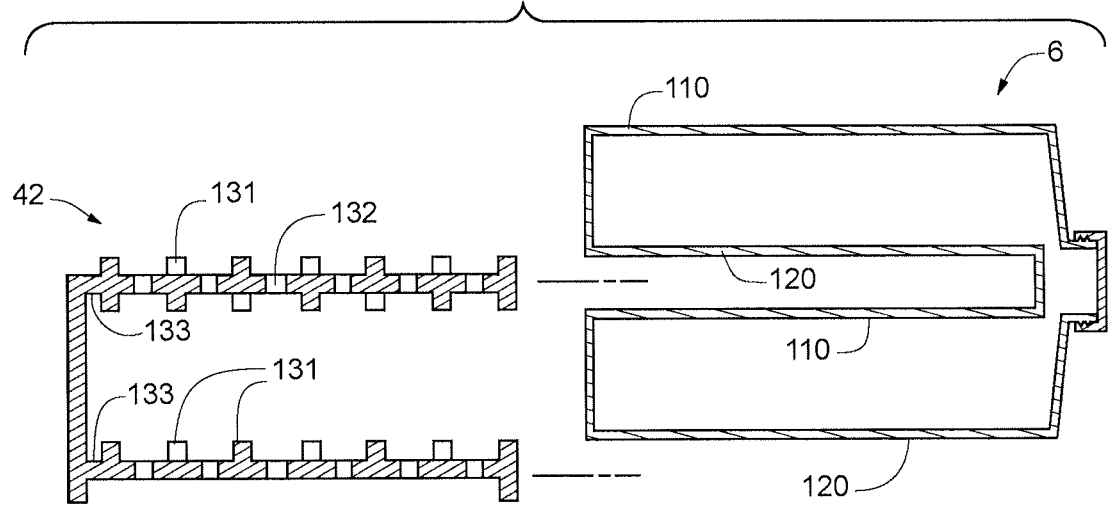
FIG. 9A and FIG. 9B illustrate the use of a culture compartment support for the purpose of allowing gas to contact the gas permeable material of the culture compartments and/or for the purpose of maintaining the culture compartments in a substantially horizontal position in order to allow cells to distribute uniformly within the culture compartments.
Figure 9B:
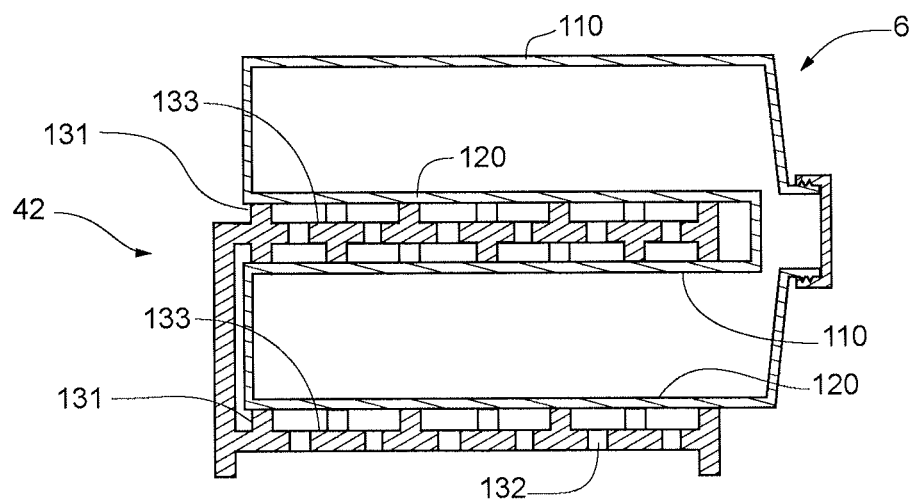

Although it can be permanently affixed to the gas permeable multi-shelf device, the culture compartment support does not need to be. This may be desirable when a user has a need to convert the device for a more controlled application, or to reduce manufacturing cost. FIG. 9A and FIG. 9B show an embodiment in which the culture compartment support is reusable, and the body of the gas permeable multi-shelved device is disposable. In FIG. 9A, culture compartment support 42 is shown detached from gas permeable multi-shelf device 6. In FIG. 9B, culture compartment support 42 has been placed in contact with gas permeable multi-shelf device 6. Projections 131 emanate from culture compartment support 42. The height and distance between projections 131 should be designed with the objective of making enough contact with the culture compartments of the gas permeable multi-shelved device to hold the cell culture compartments in a substantially horizontal state such that a uniform cell deposit can be achieved during inoculation. However, contact with the gas permeable surfaces diminishes gas transfer capacity. Therefore, a balance between the desire for a horizontal state and the degree of desired gas transfer must be considered. Depending on the type of cells being cultured, there can be more than one optimum design. Gas access openings 132 can be present when more access to ambient conditions is desired. In the absence of gas access openings 132, gas will move between the surface that projections 131 emanate from, such as surface(s) 133, and the culture compartment resistance to gas exchange is a function of the number of projections, the height of the projections, and the width of the device. In this illustration, to demonstrate the versatile range of design options, the first wall of the uppermost culture compartment has not been held in position by culture compartment support 42. That is possible if the culture compartment comes to a horizontal state if filled with a fluid, or a pressurized fluid, or if it is comprised of a stiff material. Also, second wall 120 of the culture compartment need not make contact with the culture compartment support if it is comprised of a stiff enough material to retain its shape when medium resides within it.

Figure 10:
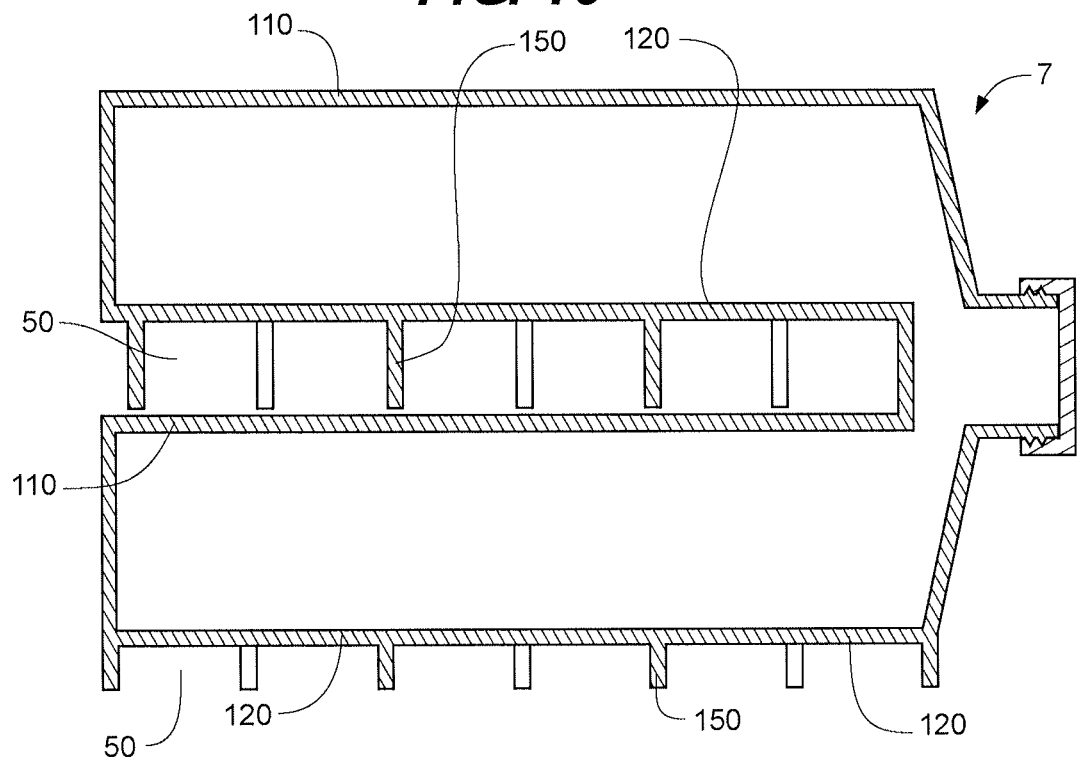
FIG. 10 illustrates the use of a culture compartment support in the form of external projections emanating from the walls of the culture compartments for the purpose of allowing gas to contact the gas permeable material of the culture compartments and/or for the purpose of maintaining the culture compartments in a substantially horizontal position in order to allow cells to distribute uniformly within the culture compartments.

The culture compartments themselves can be structured to perform the role of allowing ambient gas to communicate with the neighboring culture compartment while maintaining desired geometry. Wilson et al. U.S. Pat. No. 5,693,537 describe how a wall with projections can be used to provide support for an adjacent wall of the culture compartment. FIG. 10 shows a cross-sectional view that provides one example of how the desired shape can be maintained. In this example, first wall 110 of gas permeable multi-shelf device 7 is formed of a rigid material and the gas permeable second wall 120 is comprised of a flexible material such as dimethyl silicone. Wall projections 150 emanate from the surface of second wall 120 in order to maintain gas space 50. Wilson et al. U.S. Pat. No. 5,714,384 show how the projections can be used to increase the surface area for gas transfer. It will be understood by skilled artisans that the projections could emanate from the surface of the second wall to make contact with the first wall of the neighboring culture compartment, or from the upper and second walls. Alternatively, projections emanating from the outside surfaces of the walls of the culture compartments could interlock with each other, or with the culture compartments supports. As another approach, all walls can be flexible, and they can take the desired shape when medium fills the culture compartments.

Figure 11:
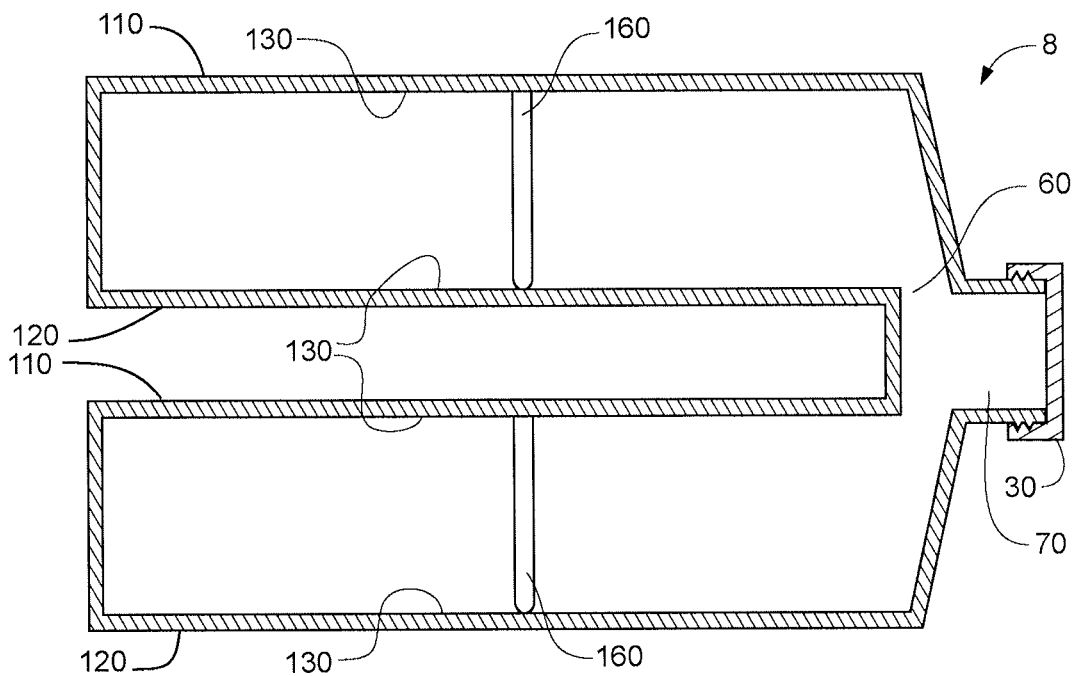
FIG. 11 illustrates the use of an internal spacer situated within the culture compartments for the purpose of preventing walls, and/or culture surfaces from contacting each other.

The upper and lower walls, and/or upper and lower culture surface, of a given culture compartment should not make contact with each other. For example, when one culture surface is tissue culture treated and contact with the opposing wall can potentially affect the tissue culture treated surface, an internal spacer can be placed within the culture compartments to ensure contact is prevented. The internal spacer can be any biocompatible material and should be configured to allow medium and fluid to easily move into and out of the culture compartment. The internal spacer need not be a separate part, as maintaining the desired space between any walls and/or culture surfaces, can be achieved by projections emanating from the upper and/or lower walls, and/or upper and/or lower culture surfaces. FIG. 11 shows an illustrative example in which internal spacer 160 of gas permeable multi-shelf device 8 is a boss that emanates from culture surface 130 or wall 110. Those skilled in the art will recognize that the internal spacer can be constructed in a wide variety of ways, provided that those ways do not prevent medium from entering or exiting the culture compartments.

The ability to microscopically observe cells in culture can be impeded when the culture compartments are stacked vertically, as the light is diminished. Thus, offsetting a culture compartment from the stack, as described in co-pending Wilson et al. '814 can be useful in allowing the use of an inverted microscope. Another option is to make the gas space capable of receiving light so that inverted microscopic observation is possible. To do so, the distance between the culture compartments should be great enough to allow a light source to illuminate the contents of the lowest culture compartment. The intensity of the light will depend upon the materials of the culture compartment and the height of the medium. Optically clear materials are preferred.

Figure 12:
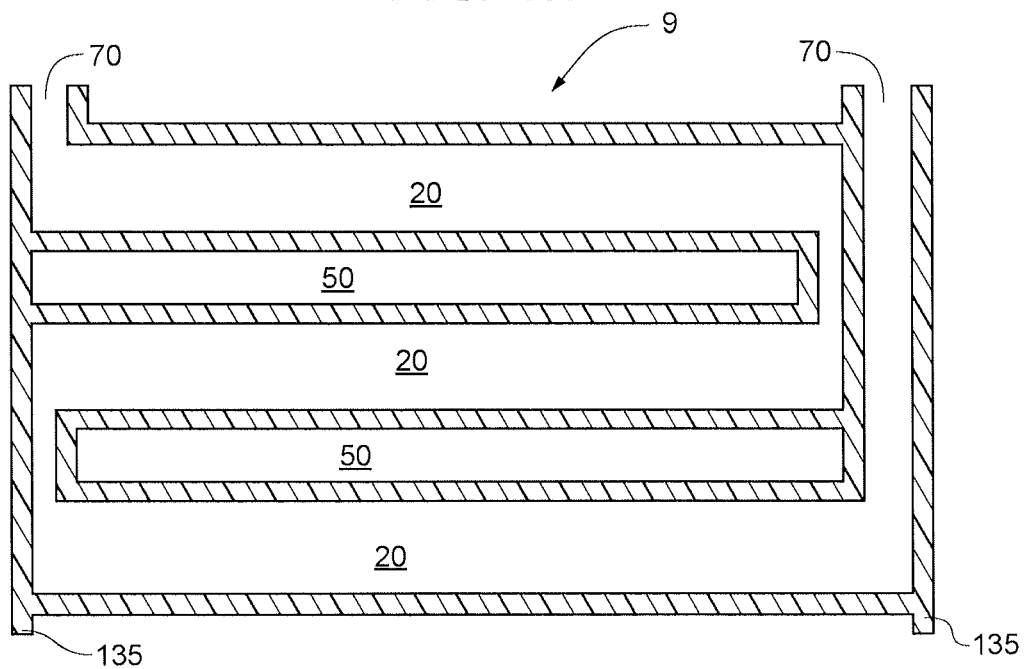
FIG. 12 shows a cross-sectional view of one embodiment of a gas permeable multi-shelf device wherein culture compartments are connected in series with inlet and outlet ports. The culture compartments form an integral unit and include a gas space adjacent to each culture compartment.

FIG. 12 illustrates an embodiment that connects culture compartments 20 in series. Liquid delivered into gas permeable multi-shelved device 9 by way of access port 70 displaces gas by way of another access port 70 and comes to reside in any desired number of culture compartments 20. A gas space 50, in communication with ambient gas, is present between culture compartments 20 and adjacent to gas permeable materials. In this illustration, gas space 50 is present in openings through the entire body of gas permeable multi-shelf device 9.

Figure 13:
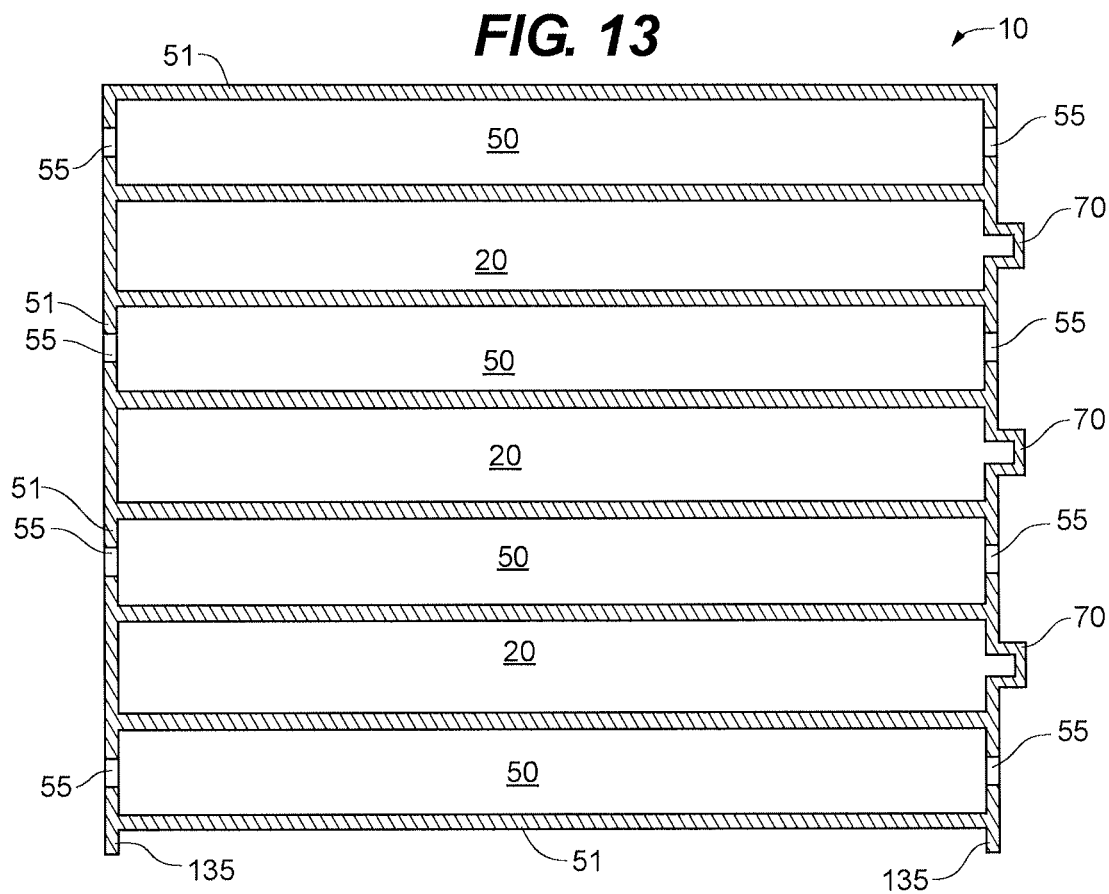
FIG. 13 shows a cross-sectional view of one embodiment of a gas permeable multi-shelf device that is configured with individual culture compartment and with a gas space residing adjacent to each culture compartment. It also shows how ambient gas access to the gas space can be selectively controlled.

In some cases there may be a desire to access each culture compartment individually, even though they are integral to a common device, such as when each culture compartment contains different cell types, or a different medium composition for a common cell type. Doing so can be accomplished by a variety of configurations. Preferably, the access to each culture compartment is structured so that it can be accomplished by standard liquid handling approaches such as pipetting or pouring, or aseptic or closed system approaches like septums or sterile tubing connections. One option is shown in FIG. 13. Culture compartments 20 of gas permeable multi-shelf device 10 can be individually accessed by way of access ports 70, in this illustration shown in a septum format. One or more access ports 70 can be connected to each culture compartment 20. In this illustration, gas space 50 is structured so that a user can allow it to be in communication with ambient gas, or prevent its communication with ambient gas. Gas space 50 is enclosed by gas space housing 51. Gas space access openings 55 in gas space housing 51 allow gas space 50 to communicate with the ambient environment. Gas space access openings 55 can be structured to be open and closed as desired. The ability to selectively terminate, restrict, or open gas movement between gas space 50 and ambient gas can be useful. This feature can be present in any embodiment. For example, when the gas permeable multi-shelf device is temporarily removed from a $CO_2$ environment, closing or restricting gas space access openings 55 can prevent or delay a shift in pH. As another example, cells of a given cell line can be placed in each compartment, the gas space in communication with a given compartment can be primed with a predetermined oxygen concentration, the gas space can be closed, and the effect of each oxygen concentrations on cell growth and/or function can be studied. Those skilled in the art will recognize that a wide variety of methods for opening and closing gas space access openings 55 are available, including luer openings and plugs, ports and caps, and the like.

Figure 14:
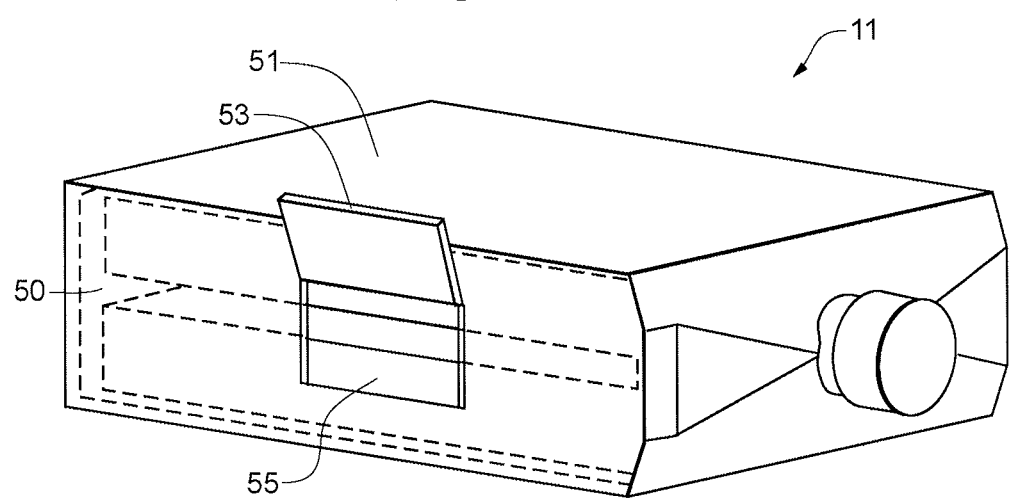
FIG. 14 shows another embodiment of a gas permeable multi-shelf device that is configured to control ambient gas access to the gas space.

FIG. 14 shows another embodiment of the gas permeable multi-shelf device configured to limit the rate of pH change when the device is removed from a standard tissue culture incubator for liquid handling in a flow hood. Gas space housing 51 encloses gas space 50 of gas permeable multi-shelf device 11. Gas space 50 can be isolated from the ambient gas by closing gas access cover 53 of opening 55 prior to removal from the incubator, thereby trapping the desired level of $CO_2$ in gas space 50. Preferably, the volume of gas in gas space 50 is enough to support the oxygen demand of the culture during the time period that gas access cover 55 is closed. Therefore, the number of cells or tissue present in the device, in addition to the oxygen demand, is a consideration for optimal volume determination.

Figure 15:
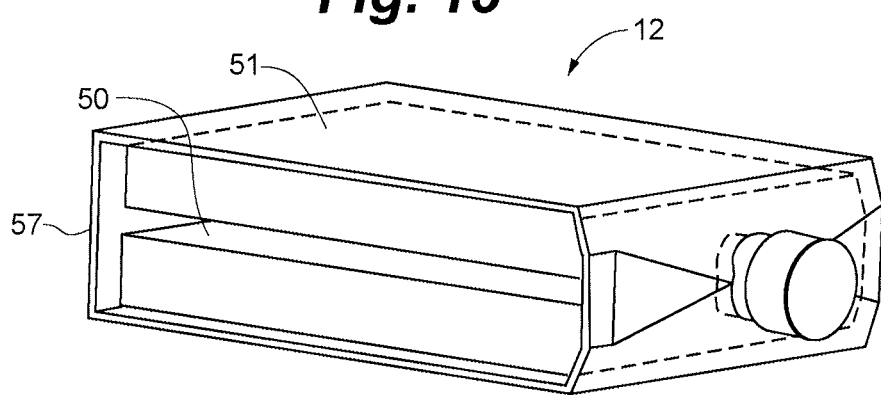
FIG. 15 shows another embodiment of a gas permeable multi-shelf device that is configured to control ambient gas access to the gas space.

FIG. 15 shows another embodiment of the gas permeable multi-shelf device configured to limit the rate of pH change when the device is removed from a standard tissue culture incubator for liquid handling in a flow hood. In this case, gas space 50 is open to ambient gas along one side of the gas permeable multi-shelf device. Gas exchange control rim 57 extends from that side of gas permeable multi-shelf device 12, in this illustration as a feature of gas space housing 51. When gas permeable multi-shelf device 12 is oriented such that gas exchange control rim 57 is flush to a flat surface, such as the floor of a laminar flow hood, gas exchange between gas space 50 and ambient gas is terminated or substantially restricted, thereby reducing the rate of pH shift. Another simple method of minimizing the rate of pH shift when the gas permeable multi-shelf device does not have features to control the shift of pH and it is removed from the incubator is to place it in an enclosure such as a box with a lid. The lid need not be gas tight to provide an advantage. So long as the cross-sectional opening of gas access between the lid and the box is less than the cross-sectional opening between the gas space and the ambient gas, a restriction in the rate of gas exchange, and a delay in pH shift will occur. The gas volume in the box when the gas permeable multi-shelf device resides within it should be minimized. Furthermore, the box can be preconditioned to contain the gas composition of the incubator prior to placing the gas permeable multi-shelf device within it.

Figure 16A:
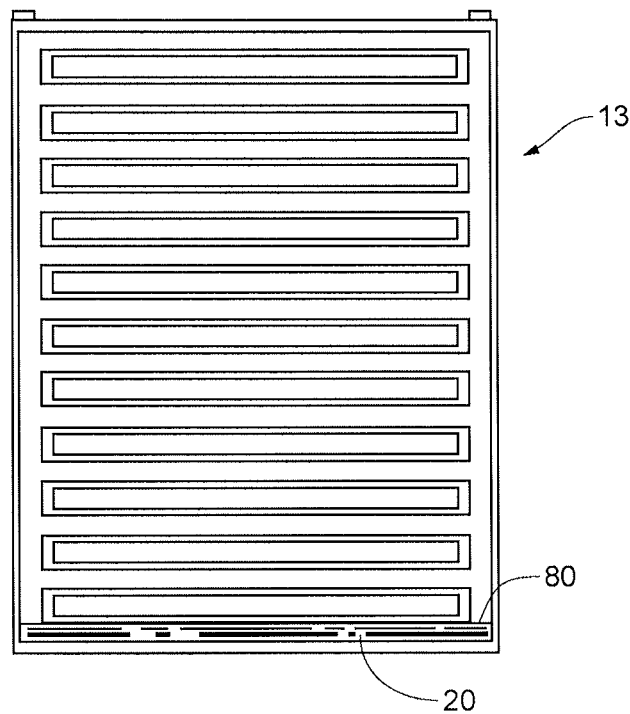
FIG. 16A and FIG. 16B show a method of using a gas permeable multi-shelf device to expand cells from one culture compartment to multiple culture compartments.
Figure 16B:
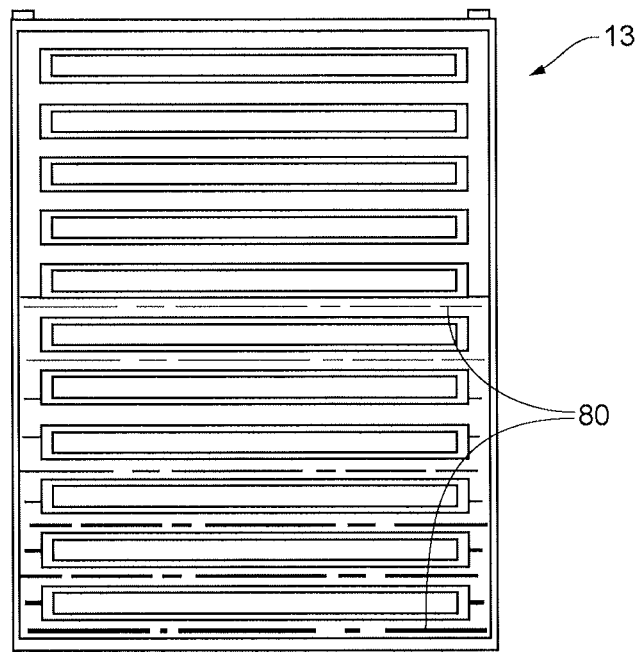

The novel gas permeable multi-shelf device allows protocols not possible in traditional multiple shelf flasks. For example, cells can be expanded from one shelf to others. A cycle of inoculating, expanding, and harvesting an adherent cell population that is not adversely affected by residual trypsin provides one example of how the closed system process can function. FIG. 16A shows a cross-sectional view of gas permeable multi-shelf device 13 with medium 80 and cells residing in the lower culture compartment 20. To expand the adherent cells to the number of culture compartments shown in FIG. 16B, a straightforward sequence of events can take place. First, medium 80 is removed. PBS is then introduced into the lower culture compartment to flush residual medium. Subsequently PBS is removed. Trypsin, or any other detachment material, is then introduced into the lower culture compartment to release cells from the attachment surface. Cells can then be redistributed to upper culture compartments by the addition of medium 80, which dilutes trypsin to a level that does not affect cell attachment. If cells are affected by any residual trypsin, the cells can be removed and it can be centrifuged out using conventional means. Then the cells can be reintroduced in an appropriate volume of medium such that they come to reside in the desired number of culture compartments. With suspension cells, the expansion to additional culture compartments can be as easy as simply adding an appropriate volume of medium. In this manner, the use of ancillary devices to create inoculum is minimized relative to traditional multiple shelf flasks, greatly simplifying the culture process. Since the gas permeable multi-shelf device can be configured for closed system access, the probability of contamination is also reduced.

The ability for cells to reside on sidewall surfaces also creates advantages that include the ability to expand cells from a surface area of one size to surfaces of increased size. For example, when by orienting the gas permeable multi-shelf device in the position shown in FIG. 5C, the culture can be initiated using a small quantity of inoculum, which will reside in proximity of walls 126. Then, when the population of the culture has expanded, more surface area can be made available by reorienting the device to the position of FIG. 5B. If needed, cells can be trypsinized from walls 126 prior to reorienting for increased surface area. If more expansion is needed, the device can then be reoriented again to the position of FIG. 5A. Subsequently, further expansion is possible by the methods described in the previous paragraph.

Any material normally associated with cell culture devices or medical devices can be used throughout the gas permeable multi-shelf device. Preferably, material that is selected meets the USP VI and/or ISO 10993 standard for compatibility. Also, optical transparency is desirable as it allows visual detection of contamination and pH. When creating surfaces that are to be observed via inverted microscope, a SPE 2 surface or better is preferred.

The gas permeable material used to allow gas transfer into and out of the gas permeable multi-shelved device can be comprised of any membrane, film, material, or combination of materials used, or previously described for use, in gas permeable cell culture devices, such as silicone, flouroethylenepolypropylene, polyolefin, polystyrene film, and ethylene vinyl acetate copolymer. Many sources for learning about gas permeable materials and their use in cell culture are available for guidance, including but not limited to U.S. Pat. Nos. 5,693,537, 6,455,310, 6,297,046, International Publication Number WO 01/92462, and co-pending U.S. patent application Ser. No. 10/961,814. An additional source of information can be found in the Plastic Design Library, William Andrew Publishing, "Permeability and Other Film Properties of Plastics and Elastomers", 1995. The use of the word silicone throughout this specification includes the formulations described in U.S. Pat. No. 6,045,877.

As described in Wilson et al. U.S. Pat. No. 5,693,537, the gas permeable material may be a liquid permeable material. Those materials include membranes that are hydrophilic throughout the cross-section, such as those comprised of cellulose, cellulose acetate, and regenerated cellulose. However, in experiments that evaluated the use of such material, it was discovered that measures for the prevention of contamination, not anticipated in Wilson et al. '537 are preferred. Care should be taken to ensure that the material selected has a low enough liquid permeability to retain a desired volume of medium within the culture compartments. Moreover, liquid loss can increase osmolarity to a detrimental level. Preferably, a material that is selected will have the ability to retain over about 90% of the medium volume in the culture compartment for the interval between feeding, at the given static pressure of the medium. During feeding, osmolarity can be restored. In the case of two-day feeding intervals, liquid loss due to static pressure should therefore preferably be limited to a ratio less than about 5% per day of medium volume within the culture device. For example, it has been discovered that 10,000 molecular weight cutoff, 80M CUPRAPHAN® membrane is an acceptable material at medium volumes of at least 10.16 ml of medium per $cm^2$ of membrane. The material is also thin, and capable of providing adequate gas transfer. In an experiment conducted in CELLine CL1000 product fabricated by Wilson Wolf Manufacturing with the lower gas permeable material composed of 80M CUPRAPHAN®, the ability to culture at least $400 \times 10^6$ murine hybridoma cells upon was demonstrated. Other than using 80M CUPRAPHAN® as the lower gas permeable membrane, all other aspects of the device were the same as the commercially available product, which integrates a non-liquid permeable, gas permeable membrane. In this experiment, the surface density was at least $4 \times 10^6$ cells/$cm^2$ of gas permeable membrane. However, although no contamination was detected within the culture compartment, the outside of the membrane became contaminated. Thus, constructing the gas permeable multi-shelf device with gas permeable, liquid permeable material should preferably restrict access to the gas space by the use of gas space access openings to the gas space that are covered with a sterile filter. Any gas permeable filtration material typically used to prevent contamination such as microporous membranes can be used. To best prevent contamination, pore size can range from 0.45 µm down, and is preferably at 0.2 However, the use of gas permeable liquid impermeable material is not limited to just the gas permeable multi-shelf device embodiments. Other gas permeable configurations, including those as simple, for example as the OPTICELL product (partially described in U.S. Pat. No. 6,821,772) could integrate at least one gas permeable, liquid permeable membrane such as CUPRAPHAN®. As another example, the Slide-A-Lyzer Dialysis Cassettes (U.S. Pat. No. 5,503, 741), normally not associated with cell culture, could be used as a culture device with a preferred configuration that included a gas space in contact with either, or both, of the dialysis membranes, and by the use of gas space access openings to the gas space that are covered with a sterile filter.

When configuring the gas permeable multi-shelf device such that it can be oriented in a first position in which suspension cells are cultured, or oriented in an alternative position in which adherent cells are cultured, a preferred configuration of construction of the gas permeable multi-shelf device should be such that one culture surface of the cell compartments is hydrophobic and a different surface is hydrophilic. An example can be illustrated by any of the cross-sectional drawing. For instance, referring to FIG. 4, first wall 110 could be gas permeable and its inner surface could be tissue culture treated to create one culture surface, while the inner surface of second wall 120 could be hydrophobic to create another culture surface. Thus, to culture adherent cells, the gas permeable multi-shelf device would be operated with first wall 110 residing below second wall 120. Thus, to culture suspension cells, the gas permeable multi-shelf device would be operated with second wall 120 residing below first wall 110. Co-culture could be conducted when adherent cells attached to first wall 110, and then the device is reoriented to allow suspension cells to reside upon second wall 120. A useful material to culture suspension cells upon is silicone, and a typical material to culture adherent cells upon tissue treated polystyrene. Therefore, in this example, a preferred embodiment would be where second wall 120 is comprised of silicone, and the culture surface of first wall 110 is comprised of tissue culture treated polystyrene. However, it was discovered that if silicone is used, it can migrate during gamma irradiation or e-beam sterilization and coat tissue treated surface within the culture compartments. This renders the tissue treated surfaces suboptimal for adherent cells. Thus, popular methods of sterilization are not practical when the most useful materials are present. Other methods of sterilization are problematic. For example, ETO will be retained in the silicone, and without a very extensive flush of the toxins, an unhealthy environment for cells will exist. Chemical means of sterilization are also require a flush. Attempts to correct the problem through the addition of colorant to the silicone, and/or variations in cure temperature and time, and/or pre-exposing the silicone to gamma irradiation at high doses, and/or changing the distance from the silicone to the polystyrene did not eliminate the problem. However, it was discovered that plasma charging the silicone prior to submitting the device to gamma irradiation showed the ability to minimize or eliminate the migration of silicone onto the polystyrene surfaces. Therefore, a preferred process of using silicone in the presence of tissue culture treated surfaces, preferably polystyrene, is to ensure that the silicone is plasma charged prior to gamma irradiation. This approach to the formation of a cell culture device is not limited to the gas permeable multi-shelf device. This approach allows any gas permeable culture device to integrate plasma charged silicone in the presence of tissue treated surfaces, with the benefit of preventing migration of silicone during traditional sterilization methods such as gamma irradiation or e-beam. For example, the devices described by Wilson et al. '814 or in U.S. Pat. No. 6,821,772 would benefit by the use of plasma charged silicone in the presence of treated surfaces. For example, the commercially available OPTICELL™ product could integrate one gas permeable tissue culture treated polystyrene surface and an opposing gas permeable surface comprised of plasma charged silicone. In this manner, when sterilized by standard methods, suspension cells could be cultured upon the surface comprised of silicone and/or adherent cells could be cultured upon the surface comprised of polystyrene. The product could integrate traditional distances between membranes, as currently is the case, or increased distances as described in Wilson et al. '814.

Figure 17A:
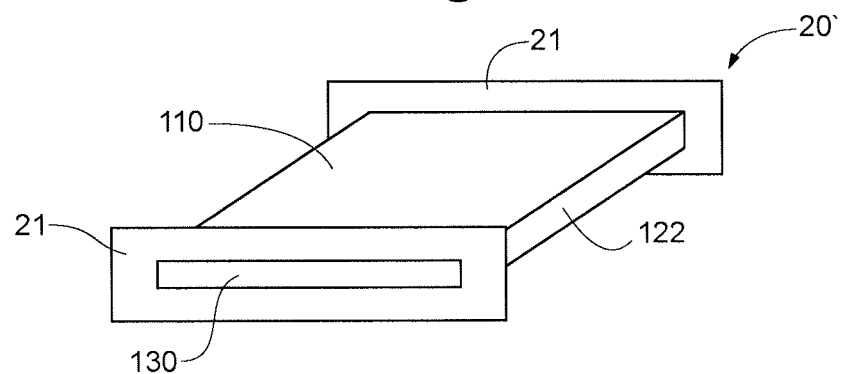
FIG. 17A shows a view of an integral culture compartment molded of silicone that minimizes the number of joints for leakage.

FIG. 17A shows a view of a culture compartment molded of silicone that minimizes the number of joints for leakage. The use of dimethyl silicone is advantageous, as it can be molded in complex geometric patterns and it is beneficial in many suspension cell culture applications. Culture compartment 20' includes flange 21. In this configuration, it is possible to eliminate joints at the intersection of the walls. Thus, it is an integral culture compartment that allows modular device design. Flange 21 can be glued to another silicone surface, or secured to any surface, such that a series of culture compartments are ready for attachment to manifold walls. Alternatively, a series of culture compartments can be prepared for assembly to a manifold wall by placing a rigid plate in front of the flanges, a rigid plate behind the flanges, attaching the rigid plates together, and then mating the subassembly to the manifold wall. Any alternative culture surfaces can be placed into the culture compartments prior to assembly. The integral culture compartment need not be limited to just one culture compartment. More than one culture compartment can be molded as an integral piece to form integral culture compartments that can also allow modular assembly. Although thickness in the areas where gas transmission is desired is preferably less than or equal to about 0.022 inches, and more preferably 0.010 inches, and most preferably less than about 0.008 inches for highly demanding cultures, greater thickness can also be useful when cells do not exhibit high oxygen demand. Thicker cross-sections of silicone can be helpful in fabrication. In general, the thicker the silicone, the easier it is to fabricate. However, the ability to fabricate an integral culture compartment of dimethyl silicone, with upper and lower walls at about 0.007 inches thick, was established. The ability to fabricate an integral culture compartment of dimethyl silicone, with sidewalls at about 0.004 inches thick was also established. Although depicted with more than one flange, the integral culture compartments need not have more than one flange. Thus, the can be dead-ended when only one manifold is desired.

Figure 17B:
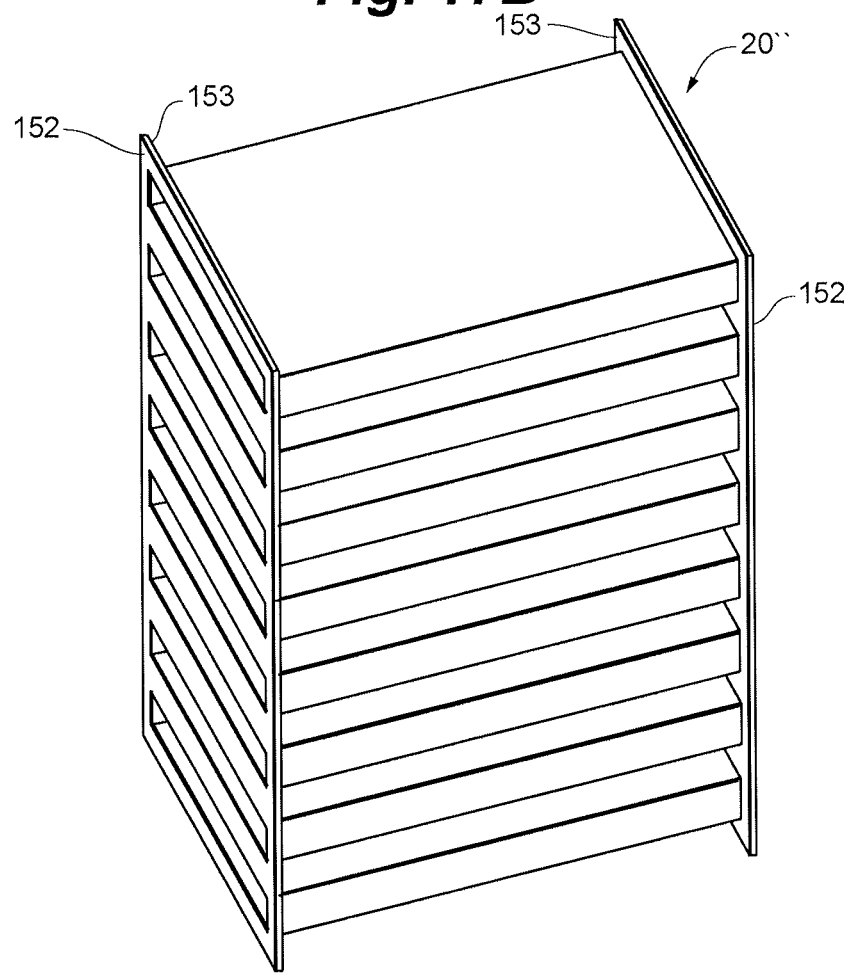
FIG. 17B shows an integral group of culture compartments fabricated as a single piece.
Figure 17C:
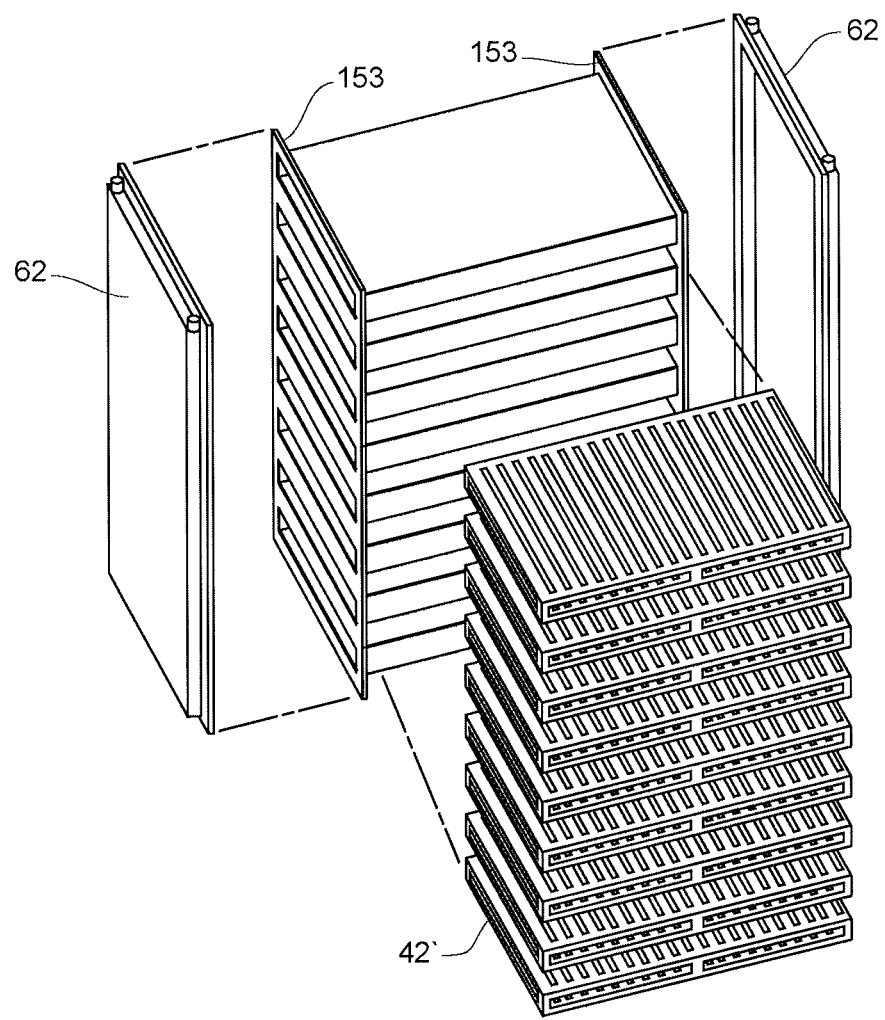
FIG. 17C shows an exploded view of a gas permeable multi-shelf device that includes integral culture compartment, overmolded flanges, and two manifolds, and culture compartment supports.

In a preferred approach, all culture compartments are molded as an integral piece with a common flange that can be secured to a manifold wall. FIG. 17B shows integral culture compartments 20", which are a series of molded gas permeable material compartments, preferably dimethyl silicone, including a flange 152. A rigid piece of plastic acting as a flange support, such as polycarbonate, can be molded directly (i.e. over-molded) onto the flange to act as a backing for subsequent further assembly. In this depiction, a flange support 153 is over-molded onto each flange 152. As shown in the exploded assembly view of FIG. 17C, flange support 153 mates to manifold wall 62 in a liquid tight manner to form a manifold on each end of the culture compartments. When evaluating the capacity to bond dimethly silicone to a rigid plastic, a liquid tight bond was obtained between dimethyl silicone and biocompatible polycarbonate. The polycarbonate material was placed in a mold and silicone was mated directly to the polycarbonate in a liquid injection molding process. Culture compartment supports can be added, such as any the range of configurations described herein and/or shown in FIG. 10 and FIG. 11. If created as described in FIG. 11, the projections can be ribs extended across the entire culture compartment. In the illustration of FIG. 17C, a series of culture compartment supports 42' are present. Even without need of further modification by introduction of a culture surface, this is a useful configuration for a wide variety of suspension cells. However, the addition of culture surfaces remains optional. When the intended application may include the use of adherent cells, it is preferred that the inner surface of the silicone by covered with a typical adherent surface appropriate for the type of cells being cultured. For a wide variety of adherent cells, inserting a layer of tissue treated polystyrene as a culture surface can be useful. That allows a wider variety of culture protocols. For example, to culture both adherent and suspension cells, the device would be oriented to allow adherent cells to gravitate to the tissue treated culture surface, and post attachment, rotated one-hundred-eighty degrees to allow suspension cells to reside upon the opposing silicone wall.

If the configurations of FIG. 17 are created with the intent of including a tissue treated culture surface other than silicone, plasma charging the silicone to prevent migration during e-beam or gamma sterilization can be avoided by covering all the inner silicone surfaces with a different culture surface. For example, thin tissue treated polystyrene can be inserted in a manner that covers all of the silicone. When manifold wall is not a material that migrates, the treated polystyrene surfaces will remain suitable for adherent culture. Although the culture surface, in this example polystyrene, provides a surface for cells to attach to, it impedes gas transfer into the cell culture compartment relative to what it would be if it were just silicone. Thus, the culture surface (or surfaces) that cells are intended to reside upon should be thin so that gas transfer can still be adequate. Preferably, the thickness in the area of the polystyrene that cells reside upon is about 0.003 inches or less. This approach reduces the number of joints and the potential for leakage, while providing culture surfaces that are suitable for any given application.

Figure 18A:
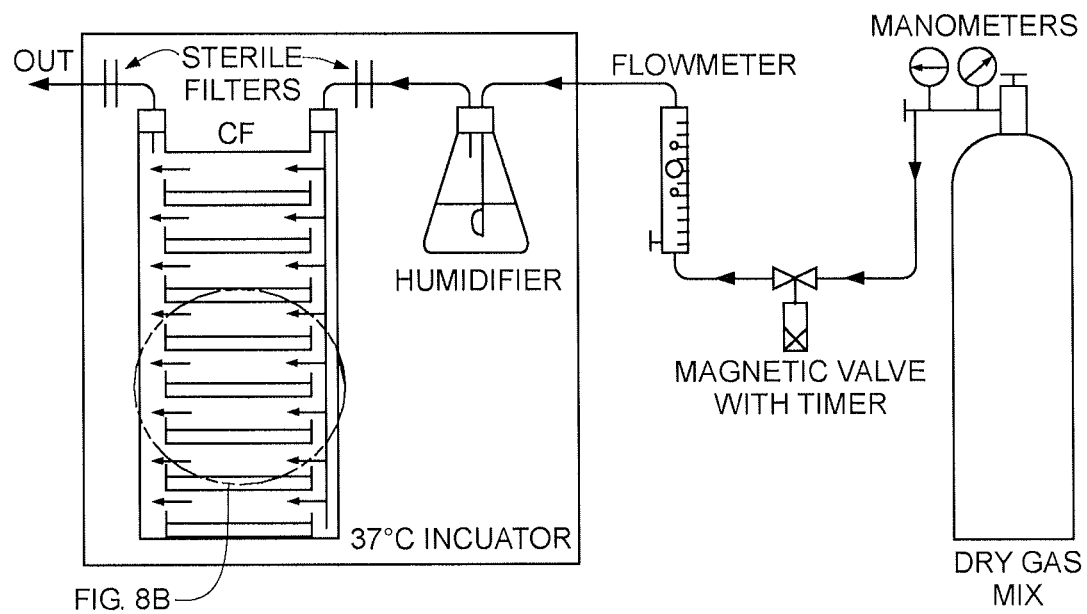
FIG. 18A shows a traditional multiple shelf flask manufacturers recommended approach to solving the problem of non-uniform culture conditions.
Figure 18B:
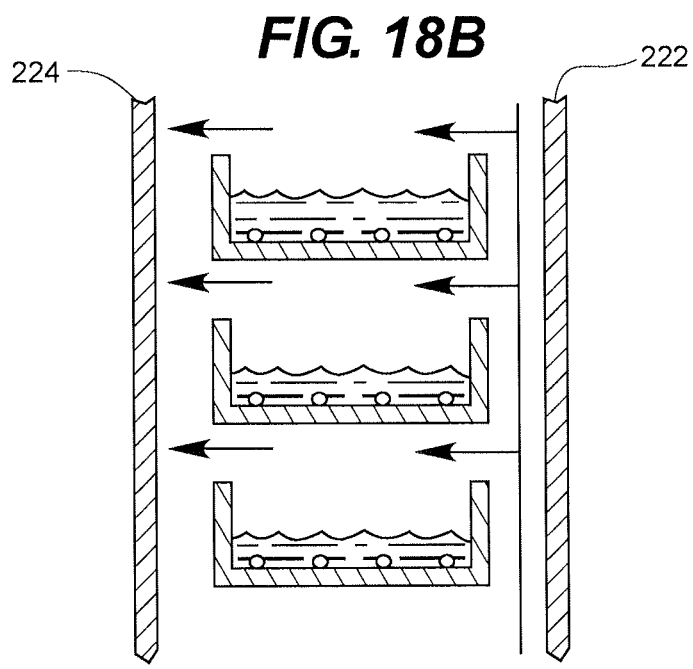
FIG. 18B shows a magnified view of that approach.
Figure 18D:
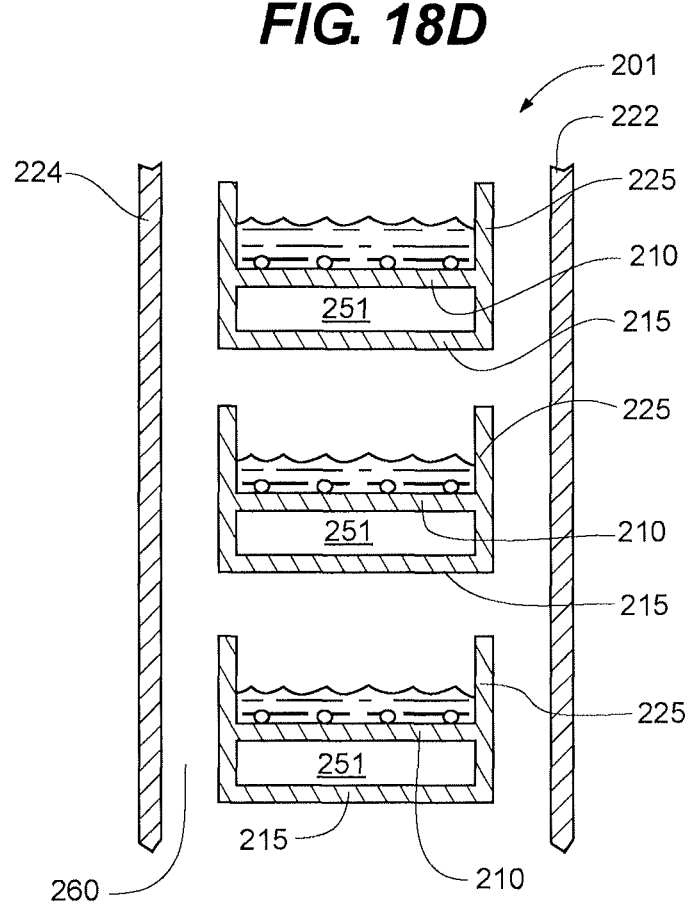

FIG. 18C FIG. 18D, and FIG. 18E illustrate the advantages of another embodiment that allows culture compartments to be partially filled with medium, and/or minimizes the volume of trypsin, PBS, or any other liquid that is involved in removing cells from the cell compartments. In this embodiment, the advantages of the present invention are integrated directly into the format of the traditional multiple shelf culture flasks such as the NUNC Cell Factory, NUNC Triple Flask, and CORNING® CELLSTACK®. FIG. 18A is a drawing provided on the website of NUNC, depicting the operation of their Cell Factory for Active Gassing, which is intended to overcome the problems of non-uniform gas composition. The gassing system complicates the process, requiring tubing connections, sterile filters, a separate gas supply, and an option for humidification since a continuous flow of dry gas mix can quickly evaporate medium and increase osmolarity to levels that affect cell growth and function. FIG. 18B is a magnified view of the NUNC approach of FIG. 18A, with arrows indicating forced gas flow and walls 224 and 222 identified for reference. The gas permeable multi-shelf flask can address the problem of non-uniform gas composition without the need for the ancillary equipment or forced gas flow required for traditional multiple shelf flasks. An advantage of the embodiments described in FIG. 18C, FIG. 18D, and FIG. 18E is that they can integrate the features present in traditional multiple shelf flasks, such as those commercially available and such as those described in U.S. Pat. Nos. 5,310,676, 6,569,675, and UK Patent Specification GB 1539263A, including any or all features that allow medium to be distributed equally to each shelf. FIG. 18C shows an embodiment of gas permeable multi-shelf flask 200 in which uniform culture conditions are attained without need of ancillary equipment or forced gas flow required for traditional multiple shelf flasks. At least a portion of wall 224 and/or wall 222 is gas permeable, allowing gas communication between gas space 250 and ambient gas. Traditional culture compartments can reside in the device, preferably with shelf 220 structured of polystyrene. Culture compartment walls 220 are structured at a traditional height to retain medium and cells such that cells 90 receive oxygen as a result of gas transfer at the interface between medium 80 and gas space 250. Manifold 260 can be structured as in that of the traditional flask. Dimethyl silicone is a good choice for gas permeable material because is can be liquid injection molded as a housing, or it can be over-molded onto rigid walls such as polycarbonate. However, as described previously, the silicone should be plasma charged in the event that gamma irradiation is anticipated. Preferably, the gas permeable area of the walls is distributed in an equal geometric relationship to each culture compartment, thereby allowing each culture compartment equivalent access to gas transfer. Stated differently, each culture compartment should reside an equal distance from gas permeable material. In the area of gas permeable material, protection from damage and structural support can be provided so long as the component providing those attributes allows gas access to the gas space. Thus, optional sidewall support 240 performs that function. It is comprised of gas access openings 242 and/or projections 241. Preferably, sidewall support is a rigid, clear material.

FIG. 18D shows another approach that eliminates the need for forced gassing as an approach to providing uniform culture conditions in traditional multiple shelved devices. This configuration integrates gas permeable materials within the body of the device. Gas space 251 is an opening through at least a portion of the body of gas permeable multi-shelf device 201. Thus, gas space 251 is bounded by upper gas space wall 210 and lower gas space wall 215. It can be an opening throughout the entire body, similar to the illustration shown in FIG. 8A and FIG. 8B. It need not pass entirely through the device, and can terminate within the device. Any of its walls can be gas permeable. However, upper gas space wall 210 need not be gas permeable to overcome the non-uniform culture conditions in the traditional multi-shelf flask. That can be achieved when any of the other walls of gas space 251 are comprised of gas permeable material. For example, upper gas space wall 210 can be polystyrene, and of a thickness that does not provide adequate gas transfer so long as at least another wall(s) of gas space 251 is comprised of material that does provide adequate gas transfer. Gas transfer at uniform locations within the body of the device affords traditional cell culture using a gas-liquid interface for gas exchange with a more uniform gas environment than that of traditional multiple shelf flasks. The gas permeable multi-shelf device need not only be operated in a manner of the traditional multiple shelf flask. Gas transfer can take place independent of a gas-liquid interface if upper gas space wall 210 is comprised of gas permeable material. Upper gas space wall 210 can mate with sidewall 225 to form a cell culture compartment. Then, for example, if there is a desire to increase medium height to minimize feeding frequency or delay a shift in osmolarity due to evaporation, medium can be added to any height desired so long as the height of culture compartment sidewalls 225 is increased accordingly as described in Wilson et al. '314.

FIG. 18E shows an illustration of an adaptation of a traditional multiple shelf flask to create a gas permeable multi-shelf flask that is configured with gas permeable wall for cells to reside upon when gas transfer through the sidewall of the device occurs. This provides more options for culture methods and addresses the issue of non-uniform culture conditions when compared to the traditional multiple shelf flask. Gas permeable multi-shelf flask 202 is configured with at least a portion of its walls, such as sidewall 224 and 222, comprised of gas permeable material. If needed, areas that are gas permeable should be supported as described in FIG. 18C. Referring again to FIG. 18E, culture compartment bottom 245 is comprised of gas permeable material and preferably is supported by culture compartment support 243, which may include projections 241 and/or gas access openings 242. Culture compartment walls 225 can be at whatever height is needed to allow medium 80 to reside at the desired height. Manifold 260 can be structured as that of the traditional flask.

EXAMPLES

Example 1 and Example 2 assessed alternate geometry of the culture compartment support in order to demonstrate quantitatively how the gas permeable multi-shelf flask has the capacity to resolve the traditional flasks excessive use of shipping, sterilization, storage, incubator, and disposal space while simultaneously minimizing the potential for non-uniform culture conditions to exist.

Example 3 describes how plasma charging silicone prior to gamma irradiation can limit or prevent its migration onto tissue culture treated polystyrene surfaces, thereby allowing silicone and tissue culture treated plastics to co-exist in the same culture compartment without need to deviate from standard sterilization processes.

Example 1

Culture Compartment Support Structures for Cultures with Very High Oxygen Demand The physical structure of a culture compartment support that would allow an improvement in islet culture, known to be one of the highest types of cultures for oxygen demand, was demonstrated by constructing a test fixture that had its lower wall comprised of a molded dimethyl silicone sheet with an average thickness measured at about 0.0072 inches thick and a surface area of 98 cm$^2$. Gas transmission of the dimethyl silicone rubber was determined by MOCON (Minneapolis, MN) using their Oxtran 2/21 Instrument in accordance with ASTM-1927 to be about 14,300 ml$_{O2}$/100 in$^2$/24 hours at 37° C. The culture compartment that supported the dimethyl silicone consisted of a 0.048 cm thick, 46% open, mesh in direct contact with the silicone. The open mesh was comprised of a series of polypropylene strands, each with a diameter of between 0.018-0.020 inches thick, arranged vertically and horizontally such that 16 strands were present per inch of horizontal distance and per inch of vertical distance. The mesh was held in place by a molded polycarbonate plastic sheet of a thickness of 0.19 cm, with uniformly distributed projections that elevated the mesh above the sheet so that a gas space resided below the membrane. Each projection was a uniformly shaped "Y", while each leg of the "Y" oriented 120 degrees apart. The length of each leg was 0.45 cm and the width was 0.127 cm. Thus, the surface area of each projection available to support the mesh was about 0.175 cm$^2$. About 1.1 projections resided per cm$^2$. Thus, the cumulative surface area of the projections available to support the mesh was about 18.87 cm$^2$. The height of each projection was 0.127 cm from the plastic sheet. A gas space resided between the bottom of the silicone and the top of the plastic sheet. The cumulative volume of gas displaced by the projections was 2.4 cm$^3$. The cumulative volume of gas displaced by the mesh was 2.54 cm$^3$. Therefore, the gas residing underneath the silicone membrane and above the plastic sheet was about 17.2 ml. The ratio of the gas residing underneath the silicone membrane and above the plastic sheet to gas permeable membrane surface area was 17.6%. The plastic sheet included through holes, acting as gas access openings, the cross-section of each being oriented perpendicular to the plane of the plastic sheet, for the purpose of allowing ambient gas to communicate with the gas space by passive diffusion. Five uniformly spaced through holes resided below the 98 cm$^2$ surface area of the dimethyl silicone, each hole having a cross-sectional area of 0.29 cm2 and a length of 0.075 in, created a cumulative cross-sectional area of 1.45 cm$^2$. Thus, the ratio of the cross-sectional area of the through holes to the cross-sectional area of the silicone membrane was about 1.45 cm$^2$/98 cm$^2$, or about 1.48%. The ratio of the cross-sectional area of the through holes to the volume of gas residing between the silicone membrane and the upper surface of the plastic sheet was thus 1.45 cm²/1 7.2 ml, or about 8.4%. Feet elevated the bottom of the plastic sheet 0.51 cm. Thus, the total height of the culture compartment support residing below the silicone membrane was 0.87 cm.

The following definitions and abbreviations are useful for understanding islet assessment:

Flask Control . . . A device that relied on a gas-liquid interface for oxygenation, seeded at a maximum of 200 IE/cm² with an IE to medium ratio of 1000 IE/ml to yield a maximum medium depth of 0.2 cm. This control is used to compare the GP Device to standard islet culture methods in flasks.

GP device . . . Test device configured with a bottom of gas-permeable dimethyl silicone comprising a surface area of 98 cm² and supported by the structure described in Example 1 or Example 2.

IE (Islet Equivalent) . . . A measure of islet volume, equal to the volume of a 150 μm diameter islet. As the vasculature of a freshly isolated islet collapses, its volume decreases and its density increases. So an IE has the same volume but not the same mass on day 0 as on day 2.

IE by DNA or DNA IE . . . An indirect measure of islet mass, equal to 11.4 ng DNA.

IE by Manual Counts . . . IE numbers are traditionally measured by manual counts which ignore how flat or dense the islets are. Day 0 IE by DNA were 63±12% of IE by manual counts in 18 porcine islet isolations (range 49-93%). Numbers usually converge as islet volume drops in culture but this is not always the case as manual counts are prone to errors. Unless otherwise noted, IE refers to an IE measured traditionally by manual counts.

Islet Fractional Viability . . . The fraction of islet mass that is viable.

Islet Surface Density . . . The volume of islets cultured upon a given surface area, expressed as IE/cm². A confluent square array of 150 μm diameter islets has 4444 IE/cm².

Medium Dilution . . . The ratio of medium volume to number of islets residing in a device, expressed as μl/IE.

Non-GP device . . . A control device configured with identical geometry as the GP Device, but without a gas-permeable membrane (used as an experimental control with identical culture conditions as the GP Device to quantify the benefit of the gas permeable membrane feature).

Porcine Isolation . . . The process of obtaining islets from the pancreas of pigs using the Ricordi Method.

OCR . . . Oxygen Consumption Rate, expressed as nmol/min. A measure of viable islet mass.

OCR/DNA . . . OCR per DNA content, expressed as nmol/min·mg DNA.

p Value . . . Reported p values are for the two-tailed paired Student's t-Test.

Recovery . . . The fraction of an islet attribute (e.g., DNA, IE, OCR) remaining present at a later time.

An initial assessment was conducted using porcine islets to determine what the ratio of medium volume to IE would be needed. Porcine islets were cultured at 37° C. for 2 days in small GP devices with a dimethyl silicone surface area of 18 cm², at 200 IE/cm² and medium dilutions at 1 μl/IE and 4 μVIE showed no statistical difference in islet viability as assessed by OCR/DNA. For 5 porcine isolations, the OCR/DNA at 4 μl/IE ranged from 97.5% to 102.4% of that at 1 μl/IE, with the combined average at 101%. Based on this finding, a medium dilution ratio of 1 μl/IE was used for the bulk of the evaluations described in Example 1 and Example 2.

Islets from 10 porcine isolations were used in a series of experiments, with the primary objective of determining if surface density beyond conventional methods, ranging from about 1000 IE/cm² to 2551 IE/cm² by manual counts (490 IE/cm² to 2551 IE/cm² by DNA counts) in the GP devices could be achieved without loss in fractional viability relative to flask controls (i.e. gas-liquid interface) at conventional surface density less than about 200 IE/cm² by manual counts. Non-GP devices controls were present with the hypothesis that a compartment support structure that only rendered the surface that cells resided upon horizontal, and not providing gas delivery, would render poor islet viability. In question was the ability of the culture compartment support, structured as described above, to allow adequate oxygen delivery to the islets while managing to maintain islets in a uniform distribution absent the loss of health from aggregation. The GP devices were structured such that islets were uniformly distributed across the 98 cm² surface of dimethyl silicone. Average islet surface density in GP devices was 1526 IE/cm² by manual counts. Based upon the ratio of fractional viability of GP devices to that of representative flask controls, GP devices showed equal viability with a standard deviation of 9.4% and a p value of 0.9987. Thus, the ability for the culture compartment support to allow passive gas transfer into the culture compartment at a rate that allowed at least an average 7-fold increase in surface density relative to traditional methods without loss of islet viability as determined by OCR/DNA was demonstrated. This demonstrates that a culture compartment support can be structured to allow ambient gas to be present on the opposite side of a culture compartment support relative to the gas permeable surface in proximity of the culture compartment support, passively move along the culture compartment support, then perpendicular to the surface upon which cells reside, and then passively circulate below the gas permeable surface upon which cells reside while providing enough oxygen transfer to support islets at beyond seven times that allowed in traditional culture devices.

Example 2

A different physical structure of a culture compartment support than that of Example 1 was examined in another islet culture application. In this example, test fixtures included virtually identical gas permeable material as that of Example 1. The culture compartment that supported the dimethyl silicone consisted of an open mesh in direct contact with the silicone, and a machined polycarbonate plastic sheet supported the mesh in a generally horizontal position. Unlike the culture compartment support of Example 1, the mesh resided directly upon the upper surface of the plastic sheet. The mesh geometry and material composition was identical to that of Example 1. For each cm² of silicone membrane surface area, the volume of gas between the lower surface of the silicone and the upper surface of the plastic bottom, after displacement by the mesh, was 0.022 ml. Stated differently, the ratio of gas volume between the plastic sheet and the gas permeable membrane to the surface area of the gas permeable membrane was 2.2%. In order to allow ambient gas to communicate with the gas space by passive diffusion, through holes, acting as gas access openings, were present in the plastic bottom, the cross-section of each being oriented perpendicular to the plane of the mesh. Each through hole had a diameter of 0.125 inches. The through holes where uniformly spaced in a grid pattern below the dimethyl silicone, such that the distance between the center of each hole was 0.375 inches. Each through hole had a length of 0.13 inches. The ratio of the cross-sectional area of the through holes to the cross-sectional area of the silicone membrane was about 16% of the membrane surface area. The ratio of the cross-sectional area of the through holes to the gas volume between the plastic sheet and the gas permeable membrane was 273%. Since the mesh had a height of about 0.019 inches, the cumulative distance between the dimethyl silicone and the gas residing under the plastic bottom was about 0.15 inches. Eight uniformly distributed feet elevated portions of the perimeter of the plastic bottom 0.41 cm from the surface of the shelf upon which it resided. The perimeter of the bottom was 23.94 cm. The cross-sectional area between the underside of the plastic bottom and the surface upon which it resided that was thereby open to movement of ambient gas was 7.59 $cm^2$. Ignoring the feet as a restrictor to gas movement, the cross-sectional area about the perimeter open to gas movement to the location of the gas permeable dimethyl silicone was 9.85 $cm^2$. Thus, the height of the culture compartment support was about 0.5 inches.

Islets from 5 porcine isolations were used in a series of experiments, with the primary objective of determining if surface density beyond conventional, averaging an estimated 1628 IE/$cm^2$ by manual counts (927 IE/$cm^2$ by DNA counts) in GP devices could be achieved without loss in fractional viability relative to flask controls and non-GP devices. In question was the ability of the culture compartment support, structured as described above, to allow adequate oxygen delivery to the islets while managing to maintain islets in a uniform distribution absent the loss of health from aggregation. If islets were to demonstrate similar viability relative to control as shown in Example 1, the ability to create alternative geometry for culture compartment supports would be demonstrated. A primary difference in geometry is that Example 1 utilized projections, whereas Example 2 allowed the mesh to reside directly upon a flat plastic bottom. To compensate for the lack of projections, the geometry of Example 2 had about an 8-fold increase in the ratio of gas access opening cross-sectional area to gas permeable material surface area relative to that of Example 1. Islets were deposited into the GP devices such that islets were uniformly distributed across the surface of dimethyl silicone. Based upon the ratio of fractional viability of GP devices to that of controls representative of flasks, GP devices showed identical viability with a standard deviation of 13.8% and a p value of 0.9681. Thus, the ability for the alternative geometry of the culture compartment support to allow passive gas transfer into the culture compartment at a rate that allowed at least an average 8-fold increase in surface density relative to traditional methods without loss of islet viability as determined by OCR/DNA was demonstrated.

The gas permeable test device configuration was also challenged with very high increases in surface density relative to control, ranging from about 7 to 41 times beyond the conventional 200 IE/$cm^2$ surface densities of flasks. A total of 20 porcine isolations were evaluated at a surface density averaging roughly 18 times greater than the traditional surface density of flasks. There was a greater degree of variability in the data, with GP devices exhibiting an average viability of 96.0% of that of controls representative of flasks, with a standard deviation of 21.9% and a p value of 0.43.

Figure 19:
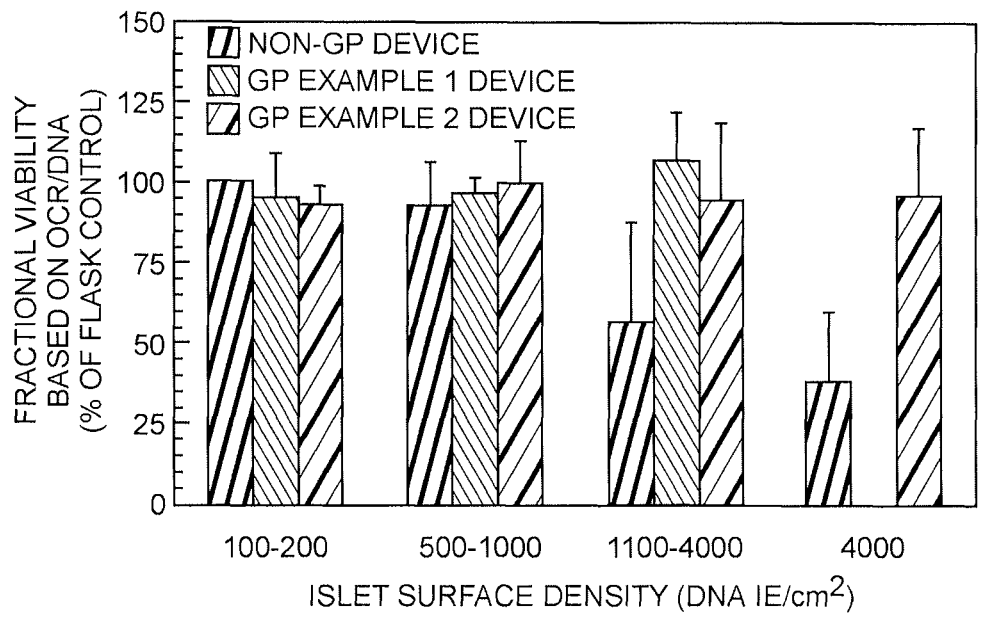
FIG. 19 shows a histogram of data collected from islet culture, a very challenging type of culture due to the high oxygen demand of islets. The superior results demonstrate the unique capacity of the gas permeable multi-shelf device to save space and provide uniform culture conditions when including beneficial geometry into its culture compartment supports.

FIG. 19 summarizes the results relative to the non-GP devices and as a percentage of flask control. Clearly, a culture compartment horizontal support that merely holds the culture compartment horizontal such that islets are uniformly distributed must include the capacity to provide adequate gas exchange, as demonstrated by the loss of islet health with increasing surface density in the non-GP device. Examples 1 and Example 2 describe how at least two distinct culture compartment supports can allow unique advantages in the efficient use of space when integrated into the gas permeable multi-shelf device design.

This information is useful in demonstrating the space advantage of the gas permeable multi-shelf device relative to the traditional multiple shelf devices. For example, in the field of islet transplants to cure type 1 diabetes, a goal is to culture up to 800,000 IE as determined by manual counts. Current flask methods at 200 IE/$cm^2$ surface densities would require 4000 cm' of culture surface area. If using a commercially available traditional multiple shelf flask, such as the NUNC Cell Factory, creating 4000 $cm^2$ of culture surface area would require about six of its 632 $cm^2$ shelves. A NUNC Cell Factor so structured would occupy roughly 416 cubic inches of space and expose islets to potentially non-uniform growth conditions. However, considering the above examples, a gas permeable multi-shelf device can culture 800,000 IE in much less space. For instance, its ability to culture islets at an average surface density of about 1526 IE/$cm^2$ to 1628 IE/$cm^2$, allows it to only require a culture surface area of about 500 $cm^2$ to successfully culture 800,000 IE. If six shelves were used in the gas permeable multi-shelf device, as required by the NUNC Cell Factory, each shelf would only need 83 $cm^2$ of surface area. If medium resided directly above islets, each culture compartment would be at a height of about 1.6 cm (0.63 in) in order to allow the same feeding frequency as the Cell Factory (i.e. 1 µL/IE). The height of the culture compartment supports (i.e. the vertical distance between culture compartments) need not exceed that of the examples. The Examples above demonstrated that each culture compartment support could be 0.344 in high. Dimensionally, the gas permeable multi-shelf device could be about 5.8 in tall, 3.6 in wide, and 3.6 in long, occupying about 76 $in^3$ of space. That is well over a 500% reduction in shipping, sterilization, storage, incubator, and disposal space when compared to the 416 $in^3$ of space occupied by traditional multiple shelf flasks. Furthermore, the non-uniform culture conditions of the traditional flask are overcome. Note that using a configuration such as that shown in FIG. 10 could further reduce the distance between the culture compartments as demonstrated by the low foot distance of the culture compartments of the above examples.

Example 3

Figure 20:
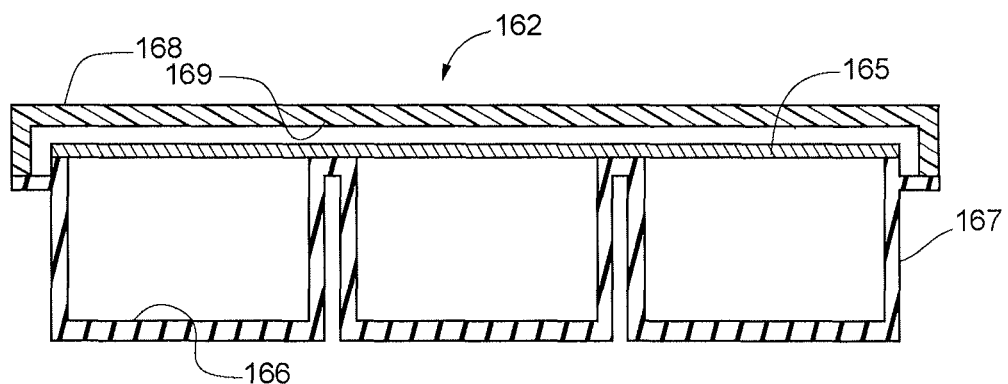
FIG. 20 shows a cross-sectional view of a test fixture used to demonstrate the usefulness of plasma charging materials comprised of silicone prior to exposing the gas permeable multi-shelf device to typical sterilization processes such as gamma irradiation in order to minimize the migration of silicone to other surfaces.

Minimizing the migration of silicone during gamma irradiation Test fixture 162 was constructed as shown in the cross-sectional view of FIG. 20. Test sample 165 was fabricated of dimethyl silicone and placed onto the top of the body of a commercially available polystyrene tissue treated six-well plate, shown as item 167 (COSTAR® 3516). The polystyrene lid 168 was then placed onto six-well plate 167. The ability to minimize migration of silicone onto inner lid surface 169 and onto tissue culture treated surface 166 by plasma charging test sample 165 prior to gamma irradiation was evaluated. Test sample 165 resided at a distance of about 1.78 cm from tissue culture treated surface 166, and less than 2 mm from inner lid surface 169. In one evaluation, test sample 165 was subjected to plasma charging prior to placing it within test fixture 162 and the presence of the plasma charge was confirmed by a water drop contact angle of ninety-six degrees and a surface energy of less than thirty dynes. In another evaluation, test sample 165 was not subjected to plasma charging prior to placing it within test fixture 162. In both evaluations, the assemblies were subsequently subjected to gamma irradiation. Thereafter, electron spectroscopy for chemical analysis (ESCA) was undertaken to quantify the elemental compositions of various surfaces. Tissue culture treated surfaces 166 were assessed for the presence of silicone, oxygen, and carbon relative to tissue culture treated surfaces of a control 6-well plate that was gamma irradiated absent silicone test sample 165. Inner lid surfaces 169 were assessed for the presence of silicone. TABLE 1 summarizes the results.

TABLE 1

| Test Condition | % Silicone | % Oxygen | % Carbon |
|---|---|---|---|
| Tissue culture treated surface 166 of control | 2.309 | 20.182 | 77.508 |
| Tissue culture treated surface 166 in the presence of plasma charged silicone test sample 165 | 2.688 | 19.549 | 77.783 |
| Inner lid surface 169 in the presence of plasma charged silicone test sample 165 | 2.324 | 6.902 | 90.049 |
| Tissue culture treated surface 166 in the presence of non-plasma charged silicone sample 165 | 24.116 | 50.65 | 25.243 |
| Inner lid surface 169 in the presence of non-plasma charged silicone test sample 165 | 16.307 | 59.511 | 24.183 |

These results show that applying a plasma charge to silicone prior to gamma irradiation prevents unwanted silicone migration and surfaces treated for cell culture remain virtually unaltered. The CORNING® six-well plate, gamma irradiated in the absence of silicone (i.e. the control), exhibited the presence of about 20% oxygen on its tissue culture treated surface, as did the CORNING® six-well plate that integrated plasma charged silicone. To the contrary, the CORNING® six-well plate that integrated un-plasma charged silicone exhibited a greatly altered oxygen composition, at 51%. Silicone that was not plasma charged migrated to all surfaces. Silicone that was plasma charged did not, independent of the proximity of the surface to the silicone.

This opens the door to new configurations of cell culture devices. In general, a simplified method of fabricating cell culture devices is possible, including, but not limited to, those described in FIG. 17A and FIG. 17B. A culture device that includes a silicone surface and a tissue treated surface can be gamma irradiated, with the tissue treated surface virtually unaltered post gamma irradiation independent of its distance from the silicone, by plasma charging at least the surfaces of the silicone that are in gas communication with the tissue treated surfaces. Surfaces of silicone that cannot migrate to the tissue treated surfaces need not be plasma irradiated, such the outside surface of culture compartments comprised of silicone. Note that surfaces that are only partially comprised of silicone should be plasma charged as described, as the silicone portion will migrate during irradiation. In general, a simplified method of fabricating cell culture devices is possible. For example, a single compartment device such as a basic flask, or the OPTICELL gas permeable cartridge, can be fabricated by molding a silicone outer housing and inserting a treated polystyrene sheet for cells to reside upon. The unique elongation capabilities of silicone allow the opening through which the culture surface is added to be smaller than the inserted part, snapping back to a port shape post insertion. Septum can be present in molded silicone, or other styles of access ports can be present. In the case of the basic flask, the height of the flask can be substantially reduced as the gas-liquid interface approach to oxygenation is eliminated by the use of gas permeable silicone. Referring to FIG. 17A, added versatility is obtained when first wall 110 is gas permeable silicone, and culture surface 130 is an adherent surface such as tissue culture treated polystyrene. In this case, the device can be oriented first wall 110 down to culture suspension cells, culture surface 130 down to culture adherent cells, or to culture adherent and suspension cells as previously described. If co-culture of adherent cells is desired, an additional culture surface such as very thin, gas permeable polystyrene, can be inserted adjacent to first wall 110. The height of the device can be increased to allow various medium volumes to surface area ratios as needed to optimize culture. Fabrication of the device with pleated sidewalls allows volume to change as needed by the user. The gas permeable multi-shelf flask can integrate these benefits also.

Those skilled in the art will appreciate that numerous modifications can be made thereof without departing from the spirit. Therefore, it is not intended to limit the breadth of the invention to the embodiments illustrated and described. Rather, the scope of the invention is to be determined by the appended claims and their equivalents.

The invention claimed is:

1. A cell growth apparatus, comprising:
an enclosure that does not include equipment for pumping gas or medium through the enclosure, the enclosure bounded by a liquid impermeable and gas permeable wall defining an interior volume capable of being filled with liquid and an exterior surface configured for contact with incubator gas, the wall forming more than one shelf with an interior surface for cells to reside upon, the interior surface of each shelf having and an opposing parallel surface located a distance away from it, each shelf being gas permeable, the shelves being located one above the other when the shelves are in a horizontal position, and the enclosure geometry having a space for incubator gas to exist below each shelf, and each shelf having an exterior surface in contact with projections that define a space for incubator gas to make contact with the exterior surface, wherein the projections are arranged in a bed of nails pattern and maintain each shelf in a horizontal position during cell culture, the enclosure is capable of being completely filled with media for optimal cell-nutrient exchange while still allowing ambient gas to make contact with a portion of the outside surface of each shelf.

2. The cell growth apparatus of claim 1, wherein the distance from each shelf and its opposing parallel surface is equal for every shelf.

* * * * *